United States Patent [19]

Ashida

[11] Patent Number: 4,906,094
[45] Date of Patent: Mar. 6, 1990

[54] FINE PARTICLE MEASURING METHOD AND SYSTEM AND A FLOW CELL FOR USE IN THE SYSTEM

[75] Inventor: Keiji Ashida, Ichihara, Japan

[73] Assignee: Sumitomo Chemical Co. Ltd., Chiba, Japan

[21] Appl. No.: 185,135

[22] Filed: Apr. 22, 1988

[30] Foreign Application Priority Data

| Apr. 23, 1987 | [JP] | Japan | 62-101013 |
| Mar. 11, 1988 | [JP] | Japan | 63-59118 |
| Apr. 5, 1988 | [JP] | Japan | 63-83659 |
| Apr. 11, 1988 | [JP] | Japan | 63-88761 |
| Apr. 15, 1988 | [JP] | Japan | 63-92964 |

[51] Int. Cl.$^4$ ............................................. G01N 15/02
[52] U.S. Cl. .................................. 356/336; 356/246; 356/339
[58] Field of Search ............... 356/336, 338, 339, 343, 356/246

[56] References Cited

U.S. PATENT DOCUMENTS

| 4,140,395 | 2/1979 | Kreikebaum | 356/336 |
| 4,276,475 | 6/1981 | Nelson | 356/336 X |
| 4,355,897 | 10/1982 | Kaye | 356/338 |
| 4,547,075 | 10/1985 | Fei | 356/246 X |
| 4,636,075 | 1/1987 | Knollenberg | |
| 4,781,459 | 11/1988 | Suzuki | 356/339 X |

FOREIGN PATENT DOCUMENTS 61-262633 11/1986 Japan .

Primary Examiner—Davis L. Willis
Assistant Examiner—Matthew W. Koren
Attorney, Agent, or Firm—Birch, Stewart, Kolasch & Birch

[57] ABSTRACT

A fine particle measuring method of this invertion is characterized in that the laser beams for forming the scattered lights comprises the following features. That is, the method comprises a first step of splitting laser beam having an intensity increasing gradually inward from its peripheral portion and the portion inner of and near to the peripheral portion into at least two parallel beams which have respective given intensity distributions, deviating from each other orthogonally to the flow direction of the laser beams in a range in which the beam spots thereof overlap each other in the flow direction, and deviating from each other by a given distance in the flow direction a second step of detecting at least two scattered light formed continuously by one of fine particles passing subsequently the parallel laser beams of the scattered lights formed by the fine particles passing the parallel laser beams; a third step of selecting an area of a scattering region to be detected; and a fourth step of computing the particle diameters of the fine particles.

94 Claims, 45 Drawing Sheets

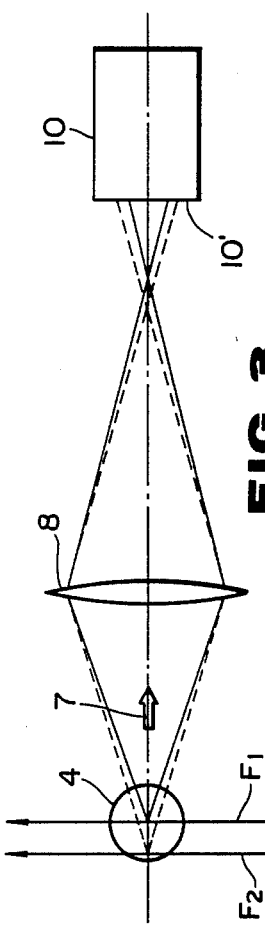
FIG. 3 *(PRIOR ART)*
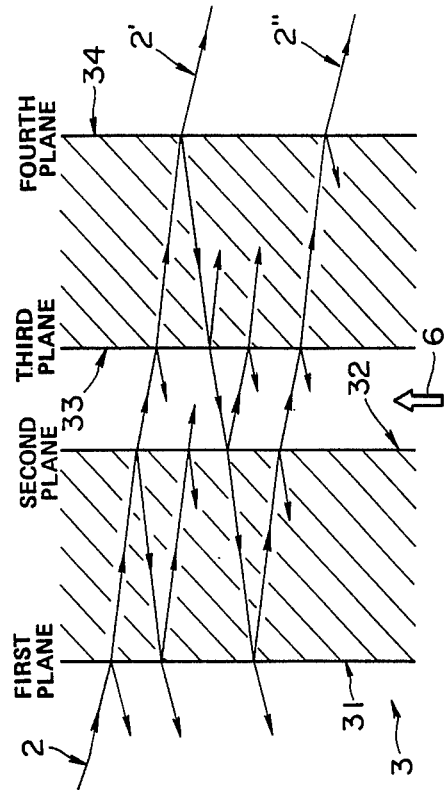
FIG. 5 *(PRIOR ART)*
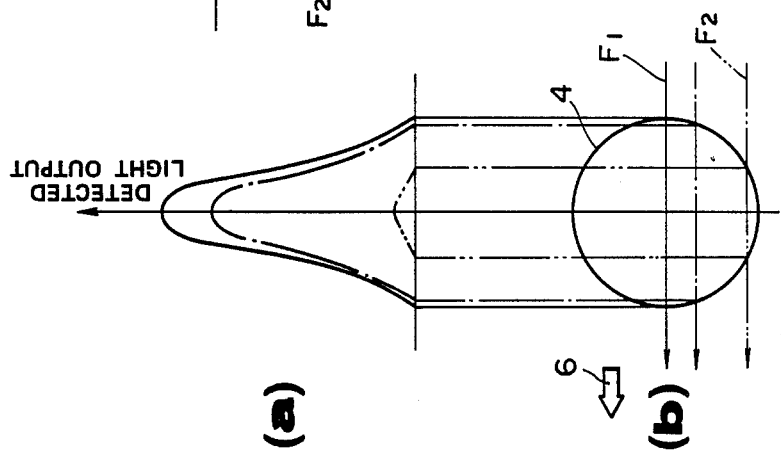
FIG. 4 *(PRIOR ART)*

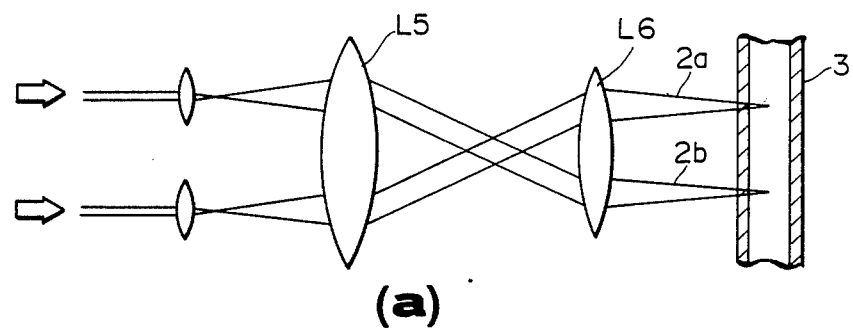
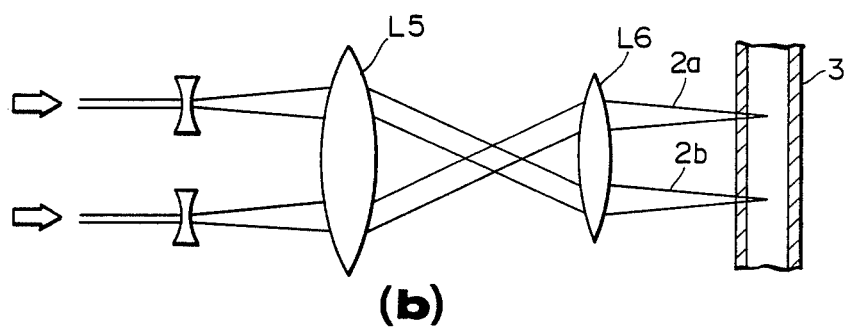
FIG.19

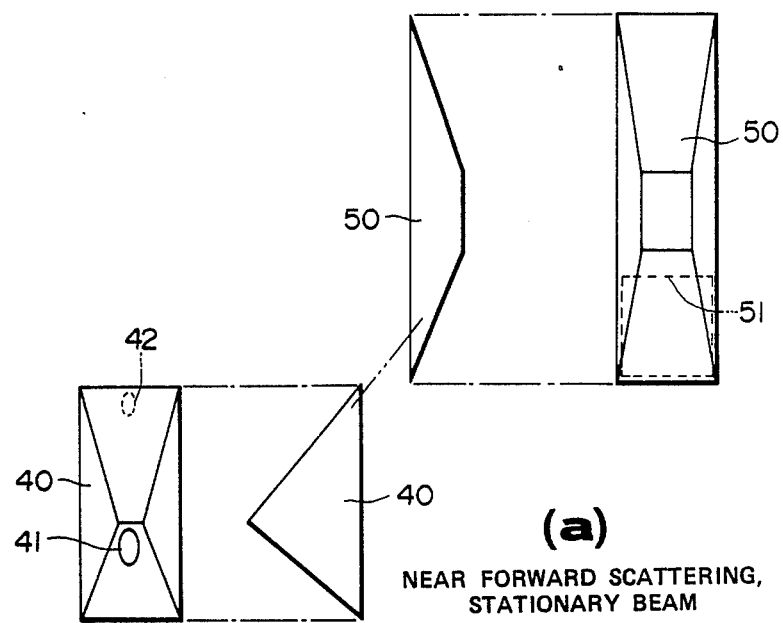
(a)
NEAR FORWARD SCATTERING, STATIONARY BEAM
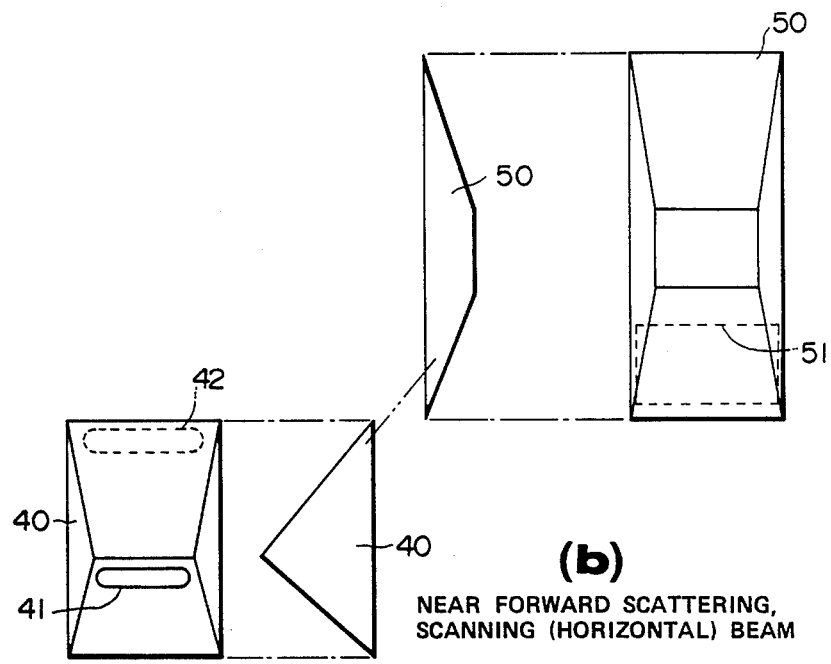
(b)
NEAR FORWARD SCATTERING, SCANNING (HORIZONTAL) BEAM
FIG.50

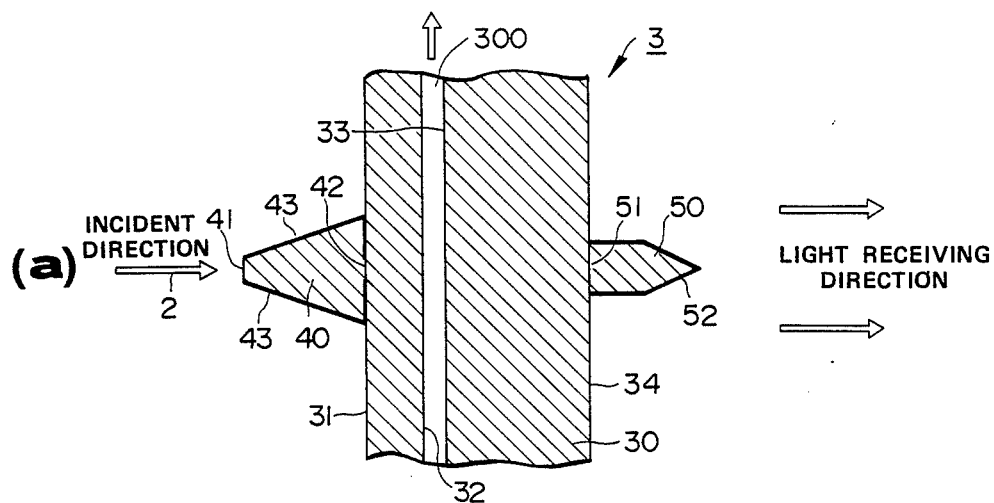
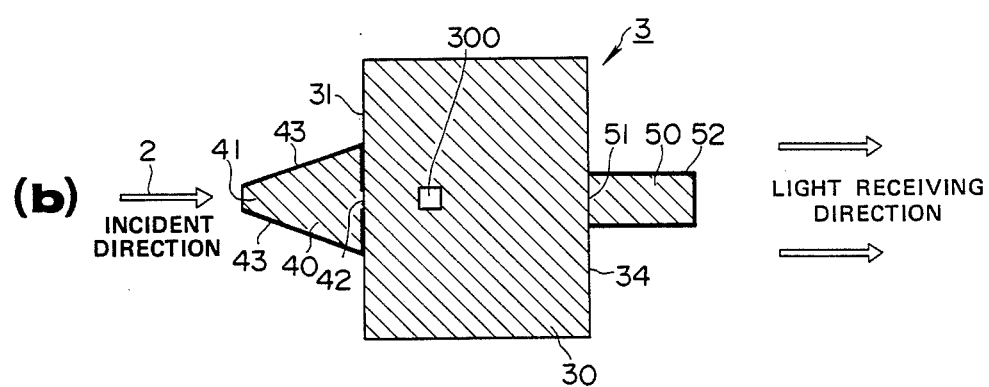
FIG. 45

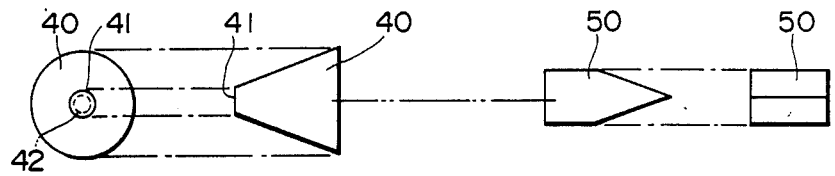
(a) FORWARD SCATTERING, STATIONARY BEAM
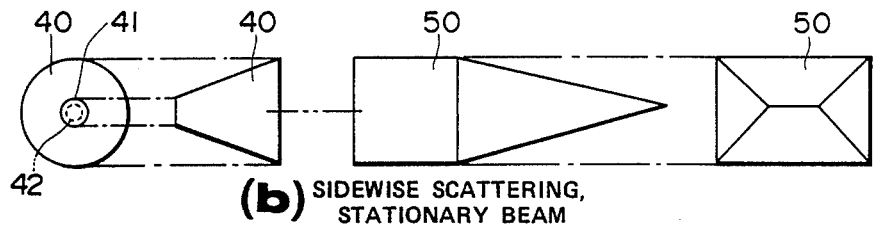
(b) SIDEWISE SCATTERING, STATIONARY BEAM
FIG. 48
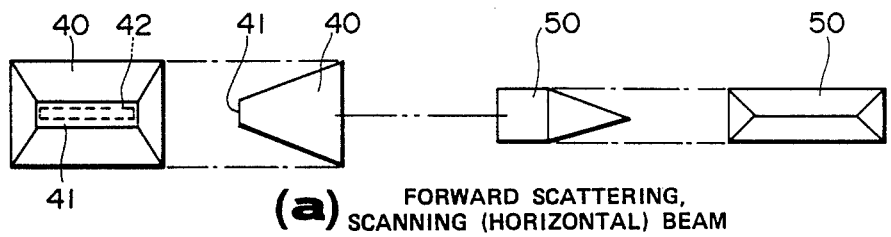
(a) FORWARD SCATTERING, SCANNING (HORIZONTAL) BEAM
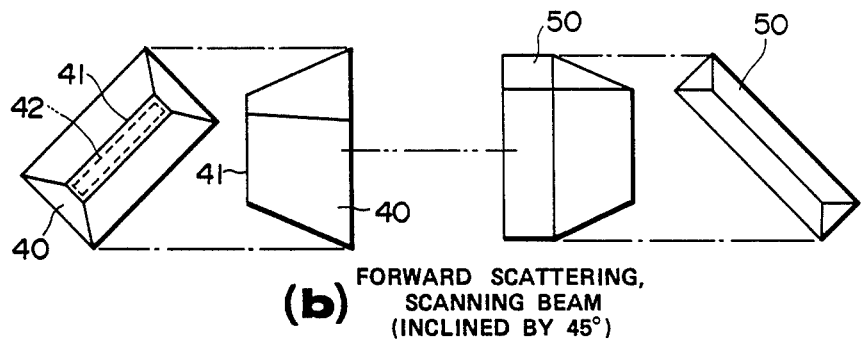
(b) FORWARD SCATTERING, SCANNING BEAM (INCLINED BY 45°)
FIG. 49

FINE PARTICLE MEASURING METHOD AND SYSTEM AND A FLOW CELL FOR USE IN THE SYSTEM

FIELD OF THE INVENTION

This invention relates to a fine particle measuring method and system, and a flow cell for use in the system, specifically for use in measuring by use of laser beam stationary fine particles or fine particles flowing at a constant flow direction through a flow cell.

BACKGROUND OF THE INVENTION

Conventionally the fine particle measuring system of this type measures, based on a ball shaped reference particle having a constant refractive index, such as a polystyrene ball or others, a particle diameter corresponding to that of the reference particle using light scattering of laser beam. In measuring particle diameters of fine particles by using light scattering, since the measured values vary depending on refractive indexes of the fine particles, a particle of a constant refractive index, such as a polystyrene ball, is used as a reference. In the following description Particle diameter means a particle diameter corresponding to that of a reference particle.

Fine particles to be measured by using light scattering of laser beam is contained in a sample fluid which flows in a given direction. The sample fluid is in the liquid phase or gaseous phase. In the case the sample fluid is in the liquid phase, it is usual to provide a flow passage by a passage member. In the case where the sample liquid is in the gaseous phase, a passage is not necessarily provided by a flow passage member. The following description is made of a case where the sample fluid is in the liquid phase, and the flow passage is provided by a flow passage member termed flow cell.

To give an example of the conventional fine particle measuring systems, FIG. 1 shows the block diagram of the system of Japanese Patent Laid Open Publication No. 265550/1986.

One laser beam 2 emitted from a laser beam source 1 is so converged by a condenser lens L that it has a given intensity distribution in a scattering region 4. The scattering region 4 is contained in the interior (not shown) of a flow cell which has a transparent portion for the transmission of the laser beam 2. A flow passage 300 defined by the flow cell is usually orthogonal to the laser beam 2. The fine particles contained in a liquid phase sample fluid flow through the flow passage 300 in the flow direction of the sample fluid indicated by the arrow 6.

The fine particles contained in the sample fluid are exposed to the laser beam 2 while passing through the scattering region 4, and disperse in every direction scattered lights in accordance with an intensity of the radiated beam. A part of the scattered lights in a partial region around a light receiving direction 7 are converged on a diaphragm 9 through a light receiving lens 8 and then pass through the aperture of the diaphragm 9 to be received by a light detector 10 disposed immediately behind the diaphragm 9. There the received scattered lights (hereinafter called scattered light outputs) are converted into an electric signal outputs in proportion with an intensities thereof, and their noise components are removed from the electric signal outputs. Then detected light outputs are obtained.

In many cases, the light receiving direction 7 is orthogonal to the direction of the laser beam in the scattering region 4 and to the flow direction 6. The system of FIG. 1 is of the sidewise scattering type. The diaphragm 9 is for defining an area of the light scattering region 4 in which a real image 14 is effectively detected, and the aperture of the diaphragm 9 defines an area of the scattering region 4 in relationship with the direction of the laser beam 2. The scattering region 4 means a region where the scattered lights dispersed by the fine particles which flow thereinto can be effectively received by the light detector 10.

In the conventional system, particle diameters are measured by the magnitude of the above described detected outputs, and based on numbers of measured diameter number of particles are counted. On the other hand, a separate flow meter (not shown), is attached to the flow passage member for measuring a total volume of the sample fluid which flows through a measuring region thereof for a measuring unit time. Using the measured values thus obtained, for example, particle diameter distributions, i.e., densities of particle numbers according to particle diameters, are computed.

Japanese Patent Laid Open Publication No. 160744/1981, for example, describes a fine particle measuring system of the forward scattering type for measuring sizes and concentrations of the fine particles in a fluid (liquid) using light scattering. FIG. 2 shows a section of the optical system of the conventional fine particle measuring system of the forward scattering type with the sample fluid in the liquid phase. A laser beam (measuring light beam) 2 emitted from a laser beam source 1 is adapted to locate its beam spot at the center of a flow passage 300 at the measuring portion of a flow cell 3 and is absorbed by a beam trap 5 disposed behind the flow cell 3. When fine particles contained in a sample liquid flows through the flow passage 300 in the flow cell 3 in a flow direction indicated by the arrow 6 passes the laser beam 2, scattered light are formed in accordance with the known Mie's light scattering theory, and parts of the scattered lights ($M_1$, $M_2$ in FIG. 2) are guided to a light receiving window 10' of a light detector 10 by a light receiving lens 8.

The above described conventional art have the following four problems to be solved. A first problem is poor precision of measured particle diameters of fine particles. A second problem is inaccurate measurement of volumes of the measured sample fluids. A third problem is low effective usage of sample fluids. A fourth problem is that the detected scattered lights include noises. These four problems will be explained one by one.

Initially a first problem to be solved by this invention will be explained.

As seen from the known Mie's light scattering theory, the intensity of the scattered light output termed above not only varies with particle diameters, refractive indexes, etc. of fine particles, but also varies in proportion with the intensities of the light beam radiated to the fine particles. In the case where a photomultiplier is used as the light detector 10, the detected light output described above is in proportion with the scattered light output. Accordingly it is necessary in measuring particle diameters based on the magnitudes of the detected light outputs that the intensity distribution of the laser beam 2 is uniform in the scattering region 4. Generally, however, the intensity distribution of the laser beam 2 is not uniform, and in the scattering region 4 the intensity of the laser beam 2 so much decreases especially in the peripheral portion of the laser beam 2 compared with the central portion thereof that in fact particle diameters cannot be measured accurately.

This problem will be elaborated with reference to FIG. 3.

FIG. 3 is a sectional view of FIG. 1 vertical to the scattering region 4 and including the flow direction 6, and shows the optical system for receiving the scattered lights formed by the fine particles passing through the scattering region 4. In FIG. 3, reference letter $F_1$ represents the flow line of the sample fluid passing the center of the laser beam 2 in the scattering region 4, reference letter $F_2$ denotes the flow line of the sample fluid passing the periphery of the laser beam 2.

Usually, the distance between the scattering region 4 and the light receiving lens 8 is about 10-20 mm, the numerical aperture of the light receiving lens 8 is about 0.4-0.5, and the spot size of the laser beam 2 in the scattering region 4 is as tiny as about 20 $\mu$m. Accordingly the corresponding numerical aperture of the light receiving lens 8 does not substantially differ between the case that fine particles pass along the flow line $F_1$ and the case that the fine particles pass along the flow line $F_2$. It may well be considered that the condensing efficiency of the light receiving lens 8 for converging the scattered lights formed by fine particles onto the window 10' of the light detector 10 is substantially equal between the two cases. Thus, a difference in the magnitudes of the outputs from the light detector 10 of fine particles of the same diameter passing the flow lines $F_1$ and $F_2$ are substantially in proportion with the intensity of the laser beam 2 on the flow line of fine particles passing the scattering region 4.

FIG. 4 shows the relationships between the positions of the flow lines and the intensity of the scattered light substituted with the relationships between the positions of the flow lines and the magnitude of the detected light output described above. In FIG. 4($a$), the detected light outputs along the solid flow line, one dot flow line and two dot flow line correspond respectively to the solid line, one dot line and two dot line outputs in FIG. 4($b$). As shown in FIG. 2, in the case that the intensity distribution of the laser beam 2 has the so called Gaussian distribution, the detected light output is the highest when fine particles pass the center of the laser beam 2 (flow line $F_1$), and lowers toward the peripheral portion thereof (flow line $F_2$). As described above, the intensity of the laser beam 2 is much lower in the peripheral portion thereof than the center thereof. Naturally this causes the conventional systems to make large measurement errors of particle diameters.

Next a second problem to be solved by this invention will be explained.

In the conventional art, there is provided a flow meter (not shown) in the flow passage member (flow cell) for measuring the total volume of a sample fluid which has flowed through a given measuring region for a measuring time, and based on the thus given measured value, the volume of the sample fluid which has passed the scattered region 4 is estimated. But this measurement needs a separate flow meter, which makes the system larger and expensive. Besides, the volume which has passed the scattering region 4 is estimated indirectly, which makes the resultant value inaccurate. U.S. Pat. No. 4636075 describes that a flow speed of a sample fluid can be determined, based on an interval between the times of measuring fine particles by two separate parallel beams. This is all the U.S. patent describes, and it includes neither the correction of the magnitude of the detected light output nor the measurement of a volume passing the scattering region.

Next a third problem to be solved by this invention will be explained.

In order to measure finer particles it is necessary to contract the spot diameter of the laser beam thereby to obtain a higher intensity of the laser beam. Specifically, when a minimum particle diameter to be detected is set at about 0.2 $\mu$m with a spot diameter of about 20 $\mu$m, the effective area of the scattering region is about $4.7 \times 10^{-2}$ mm$^2$. When the spot diameter is set about 12 $\mu$ms and the intensity of the laser beam is 10 times, the effective area of the scattering region is smaller than about $3.0 \times 10^{-3}$ mm$^2$. The sectional area of the flow passage 300 of the flow cell 3 cannot be made so small in view of its structure and pressure losses. Specifically the sectional area is about $0.8 \times 0.8 = 0.64$ mm$^2$. Thus, the effective area of the scattering region is less than 1/10 a sectional area of the flow passage 300. Consequently the effective usage of a sample fluid becomes so low that the fully effective use cannot be made of the sample fluid.

Next a fourth problem to be solved by this invention will be explained.

Recently the integrity of the semiconductor has become higher and higher. Accompanying the higher integrity, stricter quality conditions are demanded on the pure water and chemical liquids of high purity which are used in the processing of the semiconductor, and it is required to lower a critical particle diameter to be detected by the fine particle measuring system with a liquid phase sample fluid for measuring fine particles contained in a liquid. The fine particle measuring system with a liquid phase sample fluid measures particles based on the scattered light received by the light detector. The scattered output is proportional to, e.g., about 5th power of a particle diameter in the range of 0.1-0.2 micron meters, and thus as a particle diameter decreases, the scattered light output rapidly becomes so lower to be substantially equal to the noise level that it is impossible to detect fine particles.

The noises are made by various causes. To give an example, in the case where a light detector of high sensitivity, such as a photomultiplier, or other, is used, a maximum noise is caused by stray light (the light other than the scattered light) received together with the scattered light. The stray light mainly includes the transparent surface scattered light formed against surfaces 31,32,33,34 of the flow cell 3 in FIG. 2 (the scattered light $SC_1$ against the surface 31; $SC_4$, the surface 34, etc.) and the part of the laser beam 2 reflects reciprocally against the surfaces 31-34 of the flow cell 3, then goes out thereof and is not captured by the beam trap 5, when the laser beam 2 passes therethrough.

Then, the former trasparent surface scattered light will be elaborated.

The explanation will be made on the case that the laser beam source 1 is provided by, e.g., a He-Ne laser beam source, the surfaces 31-34 are made of quartz (refractive index: about 1.46), and a sample fluid is super pure water (refractive index: 1.33). A ratio of refractive indexes, i.e., a relative refractive index obtained when the laser beam 2 passes through a first surface 31 and a fourth surface 34 is about 1.46 (=1.46/1) since the outsides of the surfaces 31 and 34 are in contact with the air (refractive index: 1), but the refractive indexes to a second surface 32 and a third surface 33 is about 1.10 (=1.46/1.33).

The intensity of the surface scattered light formed when the laser beam 2 passes through the surfaces 31-34 much depends on the smoothness of the surfaces, but the surfaces at the laser beam transmitting portion of the flow cell 3 of the fine particle measuring system with a liquid phase sample fluid are polished as the usual optical planes to have substantially the same smoothness. Accordingly the intensities of the surface scattered light against the respective surfaces much depend on the relative refractive indexes, and thus the intensity $SC_1$ and $SC_4$ of the surface scattered lights against the first and the fourth planes 31 and 34, which have a higher relative refractive indexes, are much higher than those for the second and the third planes 32 and 33. That is, the noise is attributed to the stray light $SC_1$ and $SC_4$ formed against the first and the fourth planes.

Next, the latter reflected light reciprocally against the surfaces 31-34 of the flow cell 3 will be elaborated.

In the case where the laser beam source 1 is used, when the surfaces of the flow cell 3 is arranged exactly orthogonal to the laser beam 2, the light reflected against the surfaces 31-34 reverses through a laser beam emitting window and into a laser resonator 1 thereby to disturb the stability of the laser oscillation. In order to preclude this, it is usual to arrange the surfaces of the flow cell 3 not orthogonal to but inclined by some degrees to the laser beam 2.

In the case where the surfaces of the flow cell 3 in FIG. 2 are orthogonal to the flow cell 3, the reciprocally reflected light is included in the plane including the orthogonal direction and the direction of incidence of the laser beams 2. This state is shown in FIG. 5. Unless the surfaces 31-34 of the flow cell 3 are parallel to one another, the reciprocally reflected light is not in the same plane, but since it is possible to prepare a flow cell with the walls thereof arranged substantially parallel to one another, the optical path of the reciprocally reflected light is substantially in the same plane. When the light beam 2" of the reciprocally reflected light deviating much from the right optical paths 2,2' goes outside through the fourth plane 34, the beam 2" becomes a stray light without being captured by the beam trap 5. The stray light is one cause for the noise.

A first object of this invention is to provide a fine particle measuring method and system which enable precise measurement of particle diameters using light scattering of laser beam.

A second object of this invention is to provide a fine particle measuring method and system using light scattering of laser beam which enable precise measurement of particle diameters and direct measurement of a volume of a sample fluid passing a scattering region, even particle diameter distributions, e.g. densities of numbers of particles according to diameters of particles.

A third object of this invention is to provide a fine particle measuring method and system which improve effective usage of a sample fluid in measuring fine particle diameter using light scattering of laser beam.

A fourth object of this invention is to provide a flow cell for use in fine particle measuring systems which enables great reduction of the stray lights generated from the above described surface scattered lights, especially from the scattered lights on the plane of incidence of a laser beam (a first plane), preferably great reduction of the stray lights generated from the scattered lights against the transmitting surface of a laser beam (a fourth plane), and besides prevention of the generation of the stray lights from the reciprocally reflected lights between the surfaces.

DISCLOSURE OF THE INVENTION

The first three aspects of this invention are for attaining the above described first and second objects of this invention and are characterized in that the laser beams for forming the scattered lights comprise at least two parallel beams and that they comprise the following features.

That is, a fine particle measuring method according to the first aspect of this invention comprises a first step of splitting laser beam having an intensity increasing gradually from at least its peripheral portion and the portion inner of and near to the peripheral portion into at least two parallel beams which have respective given intensity distributions (e.g., substantially the same intensity distribution), deviating from each other orthogonally to the flow direction of a sample fluid and the direction of travel of the laser beams in a range in which the beam spots thereof overlap each other in the flow direction of the sample fluid, and deviating from each other by a given distance in the flow direction of the sample fluid; a second step of detecting at least two scattered lights formed continuously by one of fine particles passing subsequently the parallel laser beams of the scattered lights formed by the fine particles passing the parallel laser beams, based on a relationship between a known flow speed of the sample fluid (given by e.g., a quantitative sample feed pump or a flow meter) and an interval between the parallel laser beams; a third step of selecting an area of a scattering region to be detected, based on a ratio between the values of at least two detection ouputs of the second step (e.g., a maximum values of the above described detected light outputs or integrated values thereof); and a fourth step of computing the particle diameters of the fine particles, based on the values of at least two detected outputs obtained in the area selected by the third step.

The first step of the method according to the first aspect may be for splitting the above described laser beam into at least two laser beams which have differnt intensity distributions, the beam spots of which substantially overlap each other in the flow direction of the sample fluid and which deviate from each other by a given interval in the flow direction of the sample fluid. It is usually necessary that the two parallel laser beams are spaced from each other by a distance which precludes physical optical interferences in the scattering region. But in the case that the two laser beams are linear polarized beams, and their polarization planes are orthogonal to each other, no physical optical interference occurs, and it is not necessary to space the two beams by the above described distance.

A fine particle measuring method according to the second aspect of this invention is characterized by the first step of the method according to the first aspect, a second step, which is different from the second step of the method according to the first aspect, of merely detecting scattered lights against fine particles in a sample fluid having an unknown flow speed; a third step of measuring a time interval between, e.g., maximum values of at least two successive detected outputs (e.g., the above described detected light outputs) given by the second step; a fourth step of extracting a pair of detected outputs from one fine particle, based on, e.g., a peak of the occurrences of the time interval measured by the step 3; and steps 5 and 6, which are the same as the steps 3 and 4 of the method according to the first aspect, of measuring the particle diameters of the fine particles.

In addition to the first to the sixth steps, the method according to the second aspect may include a seventh step of computing a volume of the sample fluid passing the area of the scattering region selected by the fifth step; an eighth step of computing a particle diameter distribution, e.g., a density of particle numbers according to particle diameters, based on the particle diameters given by the sixth step and the volume of the sample fluid given by the seventh step.

A fine particle measuring system according to the third aspect of this invention comprises a laser beam source (e.g., a He-Ne laser beam source); a first optical system for splitting the laser beam from the laser beam source into at least two parallel beams having respective given intensity distributions and a given positional relationships to each other; a flow passage arranged to cross the parallel laser beams and through which a sample fluid containing fine particles to be measured flows in a given direction; a second optical system for forming scattered lights of the parallel laser beams against fine particles into an image on a given image point; light detecting means for detecting as, e.g. the above described scattered lights, the scattered lights formed in an image by the second optical system and giving forth an detected output; and measuring means for inputting the detected output, the measuring means extracting the scattered lights against one fine particle from, e.g. a time interval between maximum values of at least two detected outputs (e.g., the above described detected light outputs) successively generated, selecting an area of a scattering region to be detected based on a ratio of values of the detected light outputs (e.g., maximum values of the detected light outputs or integrated values thereof) and measuring particle diameters of the fine articles based on the values thus extracted and selected.

The measuring means of the system according to the third aspect may be for measuring a volume of the sample fluid passing the selected area of the scattering region based on, e.g., an time interval between maximum values of at least two detected outputs successively generated and measuring a particle distribution, e.g., a density of particle numbers according to particle diameters.

The fourth to the seventh aspect of this invention are for attaining the first and the second objects of this invention and are characterized in that laser beams for forming scattered lights comprise two parallel linear polarized beams and by the following features.

A fine particle measuring method according to the fourth aspect of this invention comprises a first step of splitting laser beam having an intensity increasing gradually inward from at least its peripheral portion and the portion inner of and near to the peripheral portion into at least two parallel linear polarized beams which have respective given intensity distributions (e.g., substantially the same intensity distribution), deviating from each other orthogonally to the flow direction of a sample fluid and the direction of travel of the laser beams in a range in which the beam spots thereof overlap each other; a second step of detecting for each of the linear polarized beams (each polarization plane) two scattered lights disposed simultaneously by fine particles passing the linear polarized beams; a third step of selecting an area of a scattering region to be detected, based on a ratio between values (e.g., maximum values of the above described detection outputs or integrated values thereof) of the two detection outputs of the second step; and a fourth step of correcting the values of the two detected outputs obtained in the area selected by the third step in preset procedures and measuring particle diameters based on the correction results.

The first step of the method according to the fourth aspect may be for splitting the above described laser into two parallel linear polarized beams having different intensity distributions from each other, having their beam spots substantially overlapped, and having polarization planes substantially orthogonal to each other.

A fine particle measuring method according to a fifth aspect of this invention comprises a first step of splitting laser beam into a first and a second linear polarized beams, and a third parallel beam, the beam spots of the first and the second linear polarized beams partially overlapping each other, the third linear polarized beam deviating from the first and the second linear polarized beams in the flow direction of a sample fluid; a second step of detecting merely scattered light against fine particles in the sample fluid having an unknown flow speed; a third step of measuring a maximum time interval between, e.g., a mixture values of two successive detected outputs given by the second step; a fourth step of extracting a pair of detected outputs for one fine particle based on, e.g., a peak of occurrences of the time interval measured by the third step; a fifth and a sixth steps of measuring particle diameters of fine particles in the same way as the third and the fourth steps of the method according to the fourth aspect; a seventh step of measuring a volume of a sample fluid passing the selected area of the scattering region by the fifth step; and an eighth step of measuring a particle diameter distribution, e.g., a density of particle numbers according to particle diameters, based on the particle diameters measured by the sixth step and the volume of the sample fluid measured by the seventh step.

A fine particle measuring system according to a sixth aspect of this invention comprises a laser beam source (e.g., a He-Ne laser beam source); a first optical system for polarizing laser beam into two parallel polarized beams having respective given intensity distributions and a given positional relationship with each other; a flow passage arranged orthogonal to the linear polarized beams and through which a sample fluid containing fine particles to be measured flow in a given direction; a second optical system for forming scattered lights of the linear polarized beams against fine particles into an image on an image point; light detecting means for detecting the scattered lights formed in the image as the above described scattered lights for each polarized plane and giving forth detection outputs; and measuring means for receiving the detected outputs, the measuring means selecting an area of a scattering region to be detected, based on a ratio between values of two of the detected outputs substantially simultaneously generated, (e.g., maximum values of the detected light outputs or integrated values thereof) and correcting the thus extracted and selected detected outputs by preset procedures and measuring particle diameters of fine particles based on a correction result.

A fine particle measuring system according to a seventh aspect of this invention comprises a first optical system for splitting laser beam into a first and a second linear polarized beams, and a third parallel beams, the third parallel beam deviating from the first and the second linear polarized beams in the flow direction of a sample fluid; extracting means for extracting a pair of detected outputs from one fine particle, based on, e.g., a peak of occurrences of a time interval between detection outputs of one of the first and the second linear polarized beams, and the third parallel beam; measuring means for measuring a volume of a sample fluid passing a selected area of a scattering region, based on a time interval between, e.g., maximum values of at least two detected outputs successively generated, and measuring a particle diameter distribution of, e.g., a density of numbers of particles according to particle diameters, based on particle diameters and the volume of the sample fluid.

The methods and systems according to an eighth to a twelfth aspects of this invention are for attaining the third object and preferably the first and the second objects as well, and are characterized by causing a laser beam to scan to form scattered lights and comprises the following features.

A fine particle measuring method according to the eighth aspect of this invention comprises a first step of causing a laser beam to scan having an intensity gradually increasing inward from at least the peripheral portion thereof and a portion inner of and near to the peripheral portion in the flow direction to intersect of a sample fluid; a second step of restricting a radiation area of the laser beam to fine particles in the sample fluid by the scanning direction of the laser beam; a third step of detecting scattered light against he fine particles passing the laser beam; a fourth step of measuring particle diameters of the fine particles based on the detected output given by the third step; and a fifth step of measuring a particle diameter density of the fine particles, based on a relative flow speed of the sample fluid given as a vector sum of a scanning speed of the laser beam and a flow speed of the sample fluid, and particle diameters of the fine particles given by the fourth step.

A fine particle measuring method according to the ninth aspect of this invention comprises a first and a second steps of causing two parallel laser beams; a third step of detecting scattered lights; a fourth step of selecting an area of a scattering region to be detected, based on a ratio between values of two detected outputs of two scattered lights against one fine particle detected by the third step; and a fifth step of measuring particle diameters of the fine particles based on the two detected outputs. In this method the sample fluid containing fine particles may be stationary, and the laser beam may be two linear polarized beams having their polarization planes orthogonal to each other or may be three parallel beams.

A fine particle measuring method according to a tenth aspect of this invention comprises substantially the same first and second steps as those of the method according to the ninth aspect; a third step of merely detecting scattered lights; and a fourth step of measuring time intervals of the detected outputs given by the third step. The method according to the tenth aspect is characterized by a fifth step of extracting a pair of detected outputs of one fine particle, based on the time interval between two detected outputs, and thus a sample fluid may flow at an unknown flow speed. A sixth and seventh steps are the same as the fourth and fifth steps of the method according to the ninth aspect. An eighth step of measuring a volume of a sample fluid based on a time interval between detected outputs of one fine particle, and a ninth step of measuring a distribution of particle diameters of fine particles based on particles diameters of the fine particles and the volume of the sample fluid may be included.

A fine particle measuring system according to an eleventh aspect of this invention corresponds to the method according to the eighth aspect and comprises a laser beam source; a first optical system for forming the laser beam from a laser source into a laser beam having an intensity increasing gradually inward from at least the peripheral portion and a portion inner of and near to the peripheral portion; a flow passage arranged to intersect the laser beam and through which a sample fluid containing fine particles to be detected flows in a given direction at a given flow speed; scanning means for causing the laser beam to scan at a given speed and in a given direction to intersect the flow direction of a sample fluid and orthogonal to the direction thereof; radiation range restricting means for restricting a radiation range of the laser beam to fine particles in the sample fluid by scanning direction of the laser beam; light detecting means for detecting scattered lights of the laser beam passing fine particles; and measuring means for measuring particle diameters of fine particles based on values of the detected outputs given by the light detecting means and measuring a particle diameter distribution based on a relative flow speed of the sample fluid given as a vector sum of a scanning speed of the laser beam and a flow speed of the sample fluid, and a measured result of particle diameters of fine particles.

A fine particle measuring system according to a twelfth aspect of this invention corresponds to the methods according to the ninth and tenth aspects and comprises at least one laser beam source; a first optical system for splitting laser beam from a laser beam source into two parallel laser beams having respective intensity distributions and deviating by a given distance in the direction orthogonal to the direction of the laser beam; a sample fluid reservoir for containing a sample fluid containing fine particles to be measured in its stationary condition or flowing condition; scanning means for causing at least two parallel laser beams to scan so that their beam spots may overlap each other at least partially, in the direction of relative flow determined by a vector sum of the flow direction of the sample fluid and the scanning direction of the laser beams when the sample fluid flows at a given speed in a constant direction, and in the direction of relative flow determined by the direction scanning of the laser beams when the sample fluid does not flow, a second optical system for forming scattered lights of at least two parallel laser beams against fine particles into an image on a image point; light detecting means for detecting the scattered lights formed in the image by the second optical system and giving forth detected outputs; and measuring means for extracting scattered lights against one fine particle, based on a time interval between two successively generated detected outputs, selecting an area of a scattering region to be detected, based on a ratio between at least two detected outputs, and measuring particle diameters of fine particles, based on values of the thus extracted and selected at least two outputs. The measuring means may compute a volume of the sample fluid passing the selected area of the scattering region based on a time interval between successively generated at least two detected outputs and measure a particle diameter distribution based on particle diameters and the volume of the sample fluid.

Flow cells according to a thirteenth and a fourteenth aspects of this invention are for attaining mainly the fourth object and comprise the following features.

A flow cell according to the thirteenth aspect is used in fine particle measuring systems which measure fine particles in a fluid by radiating measuring laser beam to the fluid to form scattered lights and observing the scattered lights, and is so arranged that the fluid flowing through a flow passage therein passes the measuring laser beams. The flow cell comprises a flat region over a given area, which is transparent to the measuring laser beam provided on the exterior on the side of observing scattered lights; a tubular member through the interior of which the fluid flows; and an incidence block secured to a position of incidence of the measuring laser beam of the tubular member and the surface of which except for the plane of incidence of the measuring laser beam and a beam transmitting area opposite to the plane of incidence is made light absorptive.

A flow cell according to a fourteenth aspect of this invention comprises the incidence block included in the flow cell according to the thirteenth aspect; and a beam trap having an area for receiving the measuring laser beam which has passed through a tubular member made fully light absorptive, the trap member being secured to the tubular member at a beam emitting position of the tubular member.

BRIEF DESCRIPTIONN OF THE DRAWINGS

FIG. 3 is an explanatory view of the operation of the conventional system of FIG. 1;

FIG. 4 is an explanatory view of the detected outputs for the purpose of explaining the drawbacks of the conventional system;

FIG. 5 is an explanatory view of the reciprocal reflection in the conventional flow cell of FIG. 2;

FIG. 19 is side views of the optical system for forming two pairs of parallel beams;

FIG. 45 is sectional views of the main part of the flow cell according to the first embodiment of FIGS. 43 and 44;

FIGS. 48 to 50 are views showing the structures of the incidence block and the beam trap adaptable to the flow cells according to the thirteenth and the fourteenth aspects.

DETAILED DESCRIPTION OF THE INVENTION

First Aspect of the Invention

First, a fine particle measuring method according to the first aspect of this invention will be explained in good detail.

Figure 6:
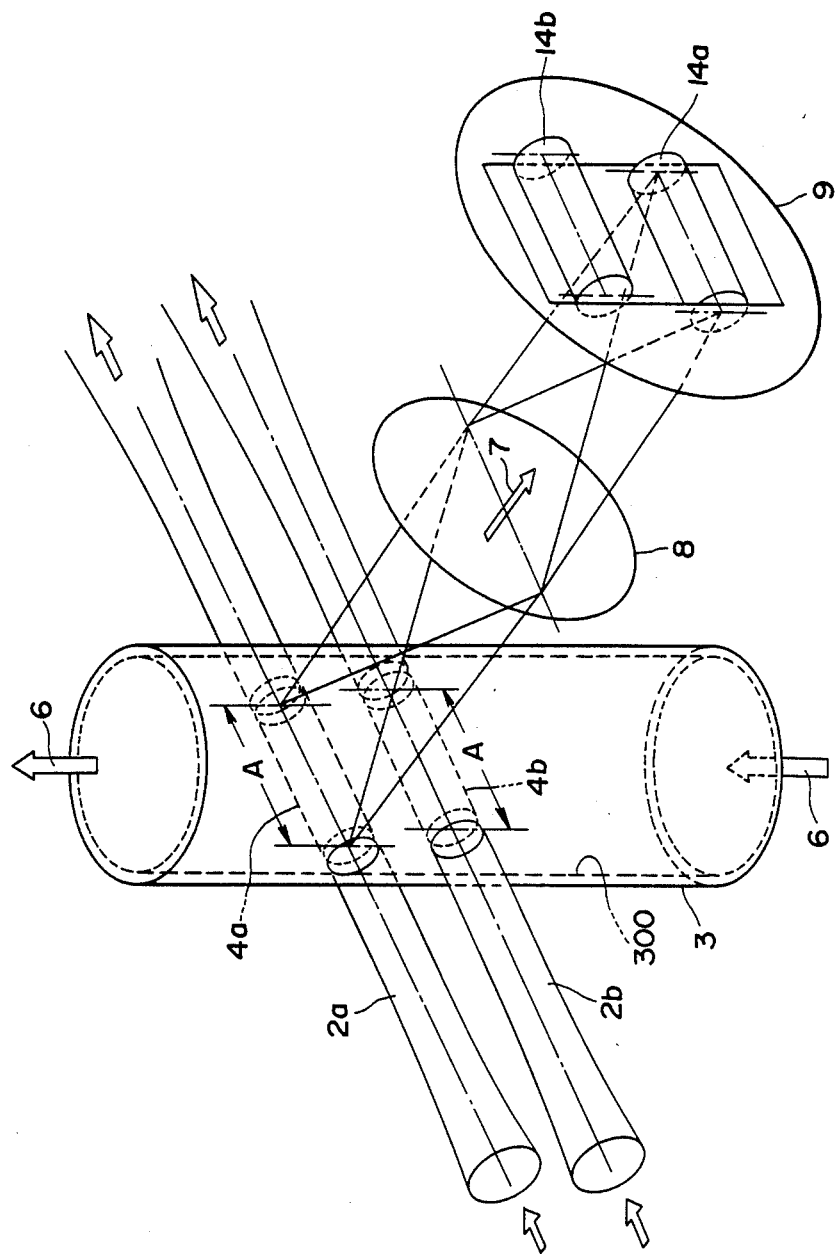
FIG. 6 is a perspective view of the main part of an optical system adaptable to the methods according to the first to the third aspects of this invention.

As shown in FIG. 6, the laser beam used in the method according to the first aspect of the invention is made of two laser beams $2a, 2b$ parallel to each other. The two parallel laser beams are spaced from each other by a given distance so that no physical optical interference may not occur between the two (only in the case they are not linear polarized beams having their planes of polarization orthogonal to each other). The intensity distributions of the two beams $2a, 2b$ are substantially the same (preferably completely the same), and their beam spot diameters are substantially the same (preferably completely the same). A cylindrical flow passage member (flow cell) 3 is disposed at the positions of the beam spots of the laser beams $2a, 2b$ orthogonally thereto. A sample fluid flows through the flow passage member 3 in the flow direction indicated by the arrow 6. The sample fluid contains fine particles to be measured.

In the case where the laser beams $2a, 2b$ are linear polarized beams having planes of polarization orthogonal to each other, no physical optical interferences takes place between them, and it suffices to space the laser beams $2a, 2b$ by a distance which allows detected light outputs to be described below to be identified. It is necessary that the flow passage is transparent at the portion where the laser beams $2a, 2b$ intersect the flow passage and also at the portion which confronts the direction of receipt of scattered lights to be described below. In FIG. 6 the sample fluid is in the liquid phase, but, needless to say, it may be in the gaseous phase, and if the sample fluid is in the gaseous phase, the flow passage member 3 is not essential. As will be described below, the first aspect is based on the assumption that the flow speed of the sample fluid is known, and a flow meter or a quantitative sample feed pump, for example, is provided in the flow passage member 3.

When fine particles in the sample fluid are radiated with the laser beams $2a, 2b$, the particles disperse the laser beams into scattered lights in every direction in accordance with the Mie's scattering theory referred to above (but, the laser beams are linear polarized beams, the scattered lights concentrate in the direction orthogonal to their electric fieled oscillating planes and their vicinities). A part of the sidewise ones of the scattered lights (the scattered lights dispered in the direction of receipt of light 7) are formed into images at a given image point as real images $14a, 14b$ in light scattering regions $4a, 4b$ through a light receiving lens 8. A diaphragm 9 is disposed near the image point, and the aperture of the diaphragm 9 (a light receiving window) restricts the lengths of the real images $14a, 14b$ in the light scattering region $4a, 4b$ to be measured. Accordingly the lengths of the light scattering regions $4a, 4b$ in the sample fluid are limited as indicated by A in FIG. 6. The limitation of the lengths of the scattering regions $4a, 4b$ is very significant in measuring particle diameters of the fine particles. This is because when the diaphragm 9 is restricting the lengths of the scattering regions $4a, 4b$ sufficiently short, the intensity distributions of the laser beams $2a, 2b$ in the light scattering regions $4a, 4b$ are substantially the same, and the beam diameters can be seen substantially the same as the beam spot diameters (minimum beam diameters), and when the diaphragm 9 is large or is absent, the intensity distributions and the beam diameters of the laser beams $2a, 2b$ differ between the central portions and both end portions of the light scattering regions $4a, 4b$. This point will be explained later in good detail.

The real images $14a, 14b$ the lengths of which are restricted by the diaphragm 9 are detected by a light detector (e.g., a photomultiplier) not shown in FIG. 6 and are converted into electric signals there. The electric signals contain noise components, and it is preferable for subsequent signal processing that the noise components are removed at a given threshold level to make the electric signals the detected light signals describe above. Then the detected light outputs (electric signals) are subjected to a given A/d conversion, etc. and are sent to computers, etc. not shown for the computation of particle diameters, etc.

The process and operation of a first embodiment of the method according to the first aspect will be explained.

Figure 7:
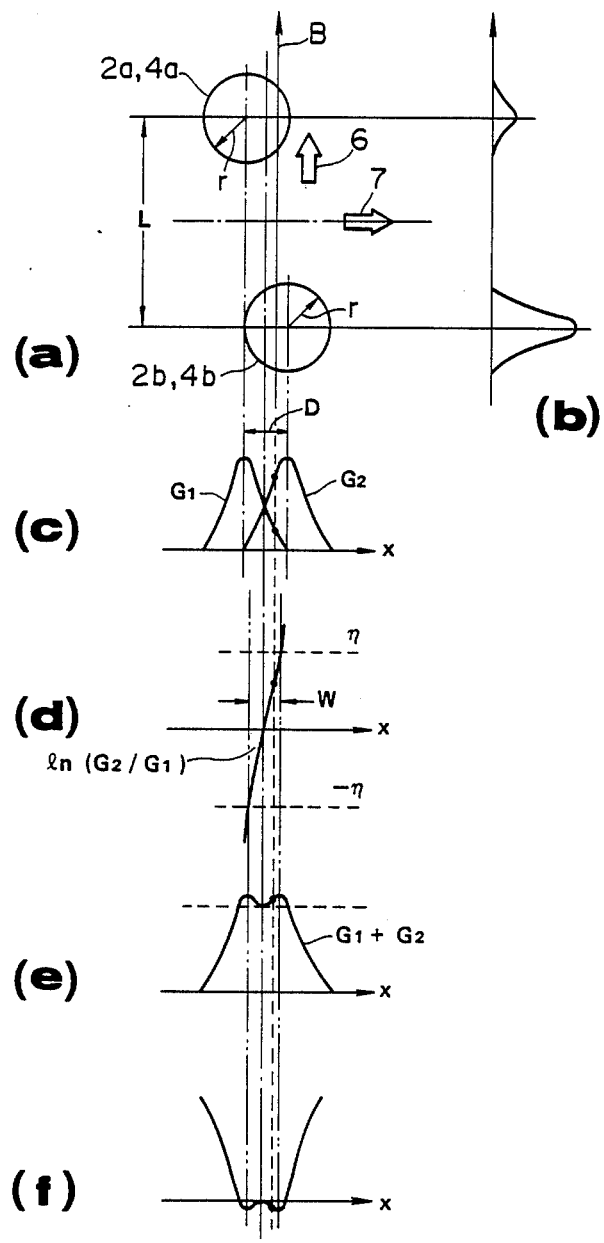
FIGS. 7 and 8 are explanatory view of the operation of an embodiment the method according to the first aspect of this invention.
Figure 8:
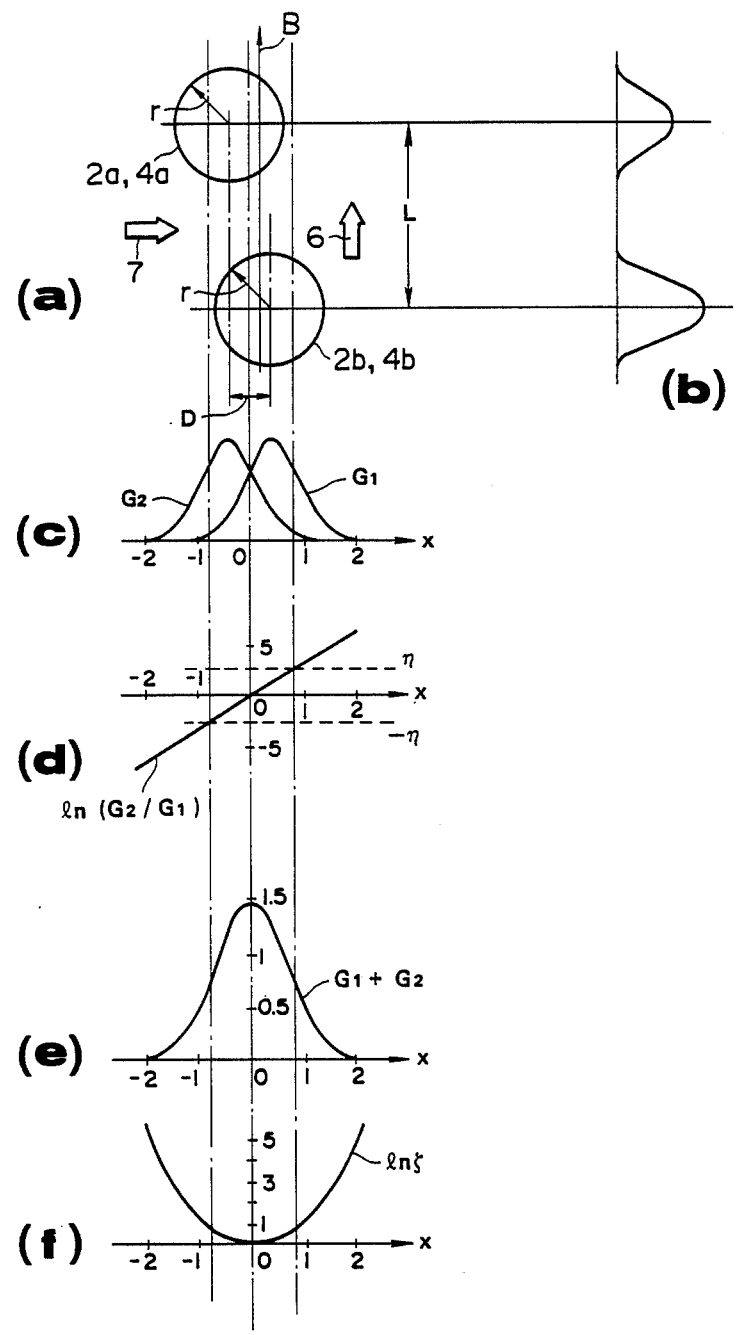

FIG. 7 includes explanatory views of the first embodiment. FIG. 7(a) shows the positional relationships between the beam spots and flow lines of fine particles. FIG. 7(b) shows detected light outputs of the scattered lights. FIG. 7(c) shows respective measured outputs of the two parallel beams. FIG. 7(d) shows a ratio between the measured outputs of the two parallel beams. FIG. 7(e) shows a sum of the measured outputs of the two parallel beams. FIG. 7(f) shows a correction coefficient of the sum of te measured outputs. FIG. 7 shows the case that a deviation amount (D) between the centers of the beam spots is substantially the same as the radius of the beam spots. FIG. 8, which will be described below shows the case that a deviation amount (D) is smaller than the radius of the beam spots.

In FIG. 7(a), (r) represents a spot radius of the laser beams $2a, 2b$, and (D) and (L) represent projection distances between the centers of the spots respectively in the direction orthogonal to the flow direction 6 and in the direction parallel to the flow direction 6. In FIG. 7(a), it is necessary that the two parallel beams $2a, 2b$ are sufficiently converged thin, and their spot diameters $2r$ is, e.g., $2r = 20$ μm. But this value is not decisive and is variable depending on required fine particle measuring sensitivities, laser beam sources, etc.

The projection distance (D) is $D \approx r$ in FIG. 7, but it is not preferable that the projection distance (D) is too large for a spot radius (r), because the probability of one fine particle intersecting both laser beams 2a,2b becomes low. To the contrary, when the projection distance (D) is too small for a spot radius (r), an area of the scattering region to be detected and measurement errors of particle diameters become large, which destroys the effect produced by using two laser beams. Then it is necessary to determine experimentally a suitable value of the projection distance (D) in the range of $0 < D < 2r$ (preferably $0 < D < r$). It is necessary to set the projection distance (L) at a suitable value so that an accurate passage time of one fine particle (a period of time from the time when one fine particle passes the laser beams 2a to the time when the fine particle passes the laser beam 2b can be obtained.

In the case that the laser beams 2a,2b are not linear polarized beams having their planes of polarization orthogonal to each other but usual laser beams (e.g., random polarized beams), it is necessary to set the distances between the centers of their spots $(D^2+L^2)^{\frac{1}{2}}$ at a value which precludes at least the physical optical interference between the two beams. Accordingly, when the spot diameter of the laser beams 2a,2b is $2r=20$ μm, and the flow speed (U) of fine particles through the scattering region is 50 cm/sec., it is preferably that the projection distances (D) and (L) are 20 μm, and 100 μm, respectively. In this case the passage time $\Delta T_L$ is about 200 μs.

When fine particles pass the spots of these laser beams 2a,2b as indicated by the arrow B in FIG. 7(a), the intensities of the scattered lights are as shown in FIG. 7(b). The detector of the scattered lights are always generating noises, and it is necessary to remove the noise components by setting a threshold value higher than the noise components thereby to detect only the portions of the outputs (portions of the detected light outputs) higher than the threshold value. The circles of the scattering regions 4a,4b shown in FIG. 7(a) indicate the ranges in which the detected light outputs exceed the threshold value for a minimum measurable particle diameter. FIG. 7(b) shows the detected light outputs higher than the threshold value by measuring time on the vertical axis, and measuring values of the detected light outputs on the horizontal axis on the right of the vertical axis.

The output value (G) used for the computation of particle diameters must be a maximum value of the detected light outputs or an integrated value of the detected light outputs in terms of time. The output value (G) varies with positions where fine particles pass, i.e., the flow passage (flow line) of fine particles and the positions where the flow line intersect the axes (x axis) orthogonal to both laser beams. It is apparent that the output value (G) is maximum when fine particles pass the center of the laser beams 2a,2b and becomes smaller when they pass the peripheral portions of the laser beams 2a,2b. FIG. 7(c) diagrammatically shows how the position (x) of passage of the fine particles varies the output value ($G_1$) generated by the laser beam 2a passing the scattering region 4a, and the output value ($G_2$) generated by the laser beam 2b passing the scattering region 4b.

When fine particles pass the midpoint between the laser beams 2a,2b (x=0), as shown in FIG. 7(c), since the radiation amount of the two laser beams 2a,2b are equal, the output values are $G_2/G_1=1$, are shown in FIG. 7(d). When fine particles deviate from the midpoint to the right (x>0), since a radiation amount is larger from the laser beam 2b than from the laser beam 2a, the output value is $G_2/G_1>1$, as shown in FIG. 7(d). Accordingly, by using laser beams having suitable intensity distributions, e.g. of Gaussin beam, $G_2/G_1$ can be made larger with increases of the rightward deviation amount. Reversely, when fine particle deviate from the midpoint to the left (x<0), as shown in FIG. 7(c), a radiation amount is smaller from the laser beam 2a than from the laser beam 2b. Similarly to the rightward deviation, $G_2/G_1$ can be made smaller than 1 by using laser beams of suitable intensity distributions.

The sum of the output value $G_1$ of the laser beam 2a and that $G_2$ of the laser beam 2b is as shown in FIG. 7(e). The sum is corrected with a correction coefficient ζ as shown in FIG. 7(f). The coefficient is derived from the sum of the output values $G_1+G_2$ at the midpoint between the laser beams 2a,2b (x=0), and the sums of the output values $G_1+G_2$ at the other points by the following equation $$\zeta = ([G_1+G_2] \text{ at } x=0)/(G_1+G_2)$$

The correction precludes the occurrence of measurement errors of particle diameters resulting from disuniform intensity distributions of the laser beams, which is a drawback of the conventional art. Besides the correction makes it possible to sufficiently enlarge the effective areas of the scattering regions 4a,4b for the measurement compared with the conventional art in which only the central portion of one laser beam having a uniform intensity distribution.

Next, the steps of measuring particle diameters of the method according to the first aspect will be explained.

The method according to the first aspect does not carry out the direct measurement of the passing speed (passage time) of fine particles, as the method according to the second aspect of this invention to be described below does. In this method, accordingly the flow speed of the sample fluid is measured by a separate flow meter or others, or the sample fluid must be so fed at a constant flow speed by a feed pump (not shown) that it flows at a flow speed in a given range. If the sample fluid flows at a known speed, with the projection distance (L) between the centers of the spots of the laser beams 2a,2b determined, the passage time of the sample fluid can be predicted by the two values.

When fine particles in the sample fluid under these conditions intersect the laser beams 2a,2b formed by a first step of the method according to the first aspect, scattered lights are dispersed in every direction around the laser beams 2a,2b, e.g., sidewise of the laser beams, forward thereof, etc. Scattered lights are detected as scattered light outputs by a light detector (not shown) and converted into electric signals to be applied to a measuring unit (not shown), where a second step of the method according to the first step starts.

Unless one fine particle intersects both of the laser beams 2a,2b, it is impossible that two detected light outputs are successively obtained at a known time interval (passage time $\Delta T_L$), which is given by a flow speed of the sample fluid and a projection distance (L). But, such detected outputs can be omitted as those not to be measured by providing an extracting circuit for extracting a pair of detected outputs (or detected light outputs having their noise components removed therefrom) at a given time interval.

The extracting circuit can be constituted with, e.g., a clock oscillator, a counter circuit for counting a clock output in response to a detected output and outputting a pulse of a certain time width (a little longer than a known passage time $\Delta T_L$), a gate circuit which gives a logical product of the counter output and a detected output and operates only when detected outputs are successive, a flip flop circuit operates at an output of the gate circuit, etc. By making the width of the output pulse of the counter circuit variable, in accordance with changes of the flow speed of the sample fluid, the extracting circuit is usable in measuring fine particles flowing different velocities if the speeds are known. The counter circuit of the extracting circuit may be a delay circuit which outputs a pulse of a given time width in response to a detected output, or may be substituted with software of microprocessors, or others.

Next, pairs of detected outputs thus extracted in the second step are examined in terms of a ratio $G_2/G_1$ in a third step. That is, only those of the pairs have a ratio $G_2/G_1$ between their respective detected outputs indicated by the natural logarithm in FIG. 7(d), that have the following relationship with respect to an allowance value $$-\eta < \ln(G_2/G_1) < \eta$$

are selected to selected an area of the scattering region $4a, 4b$ to be detected. that is, pairs having output ratios which are out of the above described range (one fine particle which has passed the periphery of one of the spots of the laser beams) are omitted from the measurement, and only pairs of detected outputs within an effective width (W) around the centers of the respective two laser beams $2a, 2b$ (suitable for the precise measurement) are left. An effective scattering areas (S) of the scattering regions $4a, 4b$ can be given from the above. That is, the length (A) of the scattering regions $4a, 4b$ are determined by the width of the diaphragm 9 as described above, and the effective width (W) of the scattering regions $4a, 4b$ are determined by the allowable value $\eta$, as described above. With the width of the diaphragm 9 made constant, the effective scattering area (S) can be expressed in a function of $\eta$.

The allowance value $\eta$ is given, e.g., by the following. That is, if a measured number of particles is (N) when a sample fluid containing suitable standard particles in a particle number density (C) is measured at a given flow speed and for a measuring time (T), a volume (V) of the sample fluid which has passed a scattering area (S) with respect to a set allowance value for a measuring time (T) is given by $V = N/C$. The volume (V), the scattering area (S), the flow speed (U), and the measuring time (T) have a relationship $$V = S \cdot U \cdot T.$$

From the equation, for a set allowance value $\eta$, a scattering area (S) or an effective width (W) of the scattering area (S) can be determined. With reference to their relationship, a suitable allowance value can be set.

Next, a particle diameter $D_p$ is measured in a fourth step of the method according to the first aspect of this invention. The particle diameter measurement is based on the output values $G_1, G_2$ of a pair left for the measurement in the second and the third steps. That is, a particle diameter $D_p$ of one fine particle is measured using a pair of outputs $G_1, G_2$ thus extracted and selected with respect to each fine particle. When the effective width (W) of the scattering regions are restricted narrower (approximating the allowance value $\eta$ to 1), the radiation amount to fine particles becomes constant. In this case, when $G_1 + G_2$ is $H_o$, a particle diameter $D_p$ is expressed in a function of $H_o$ by $$D_p = F(H_o).$$

In this case, however, the scattering area (S) is so small that a required measuring time becomes too long. Then, by making the effective width (W) a little large (making the allowance value $\Theta$ larger than 1) and multiplying the value of $G_1 + G_2$ with a correction value $\zeta(G_2/G_1)$ given in a function of $G_2/G_1$, $G_1 + G_2$ is converted into $H_o$, and then the above described function $$D_p = F(H_o)$$

is substituted with the $H_o$, and a particle diameter $D_p$ is given.

For this computation, it is necessary that the two relationships, $(G_2/G_1)$, and $F(H_o)$ are known, but they can be given experimentally. That is, for some different particle diameters, by using a sample fluid containing standard particles of given diameters for the respective different particle diameters, a number of values of $G_1$ and $G_2$ are measured to obtain $G_2/G_1$ and $G_1 + G_2$, from which the relationships between the $G_2/G_1$ and $\zeta(G_2/G_1)$ are known. It it possible to store these relationships as empirical fomulas.

The operation and the measuring steps shown in FIG. 7 are for the case wherein the deviation amount (a projection distance) (D) between the centers of two laser beams is the same as a radius (r) of the beam spots or a little larger than them. In contrast thereto, FIG. 8 shows the case that a deviation amount between the centers of two laser beams is smaller than the radius (r) of the beam spots (specifically D=0.8r). The case of FIG. 8 has the advantage of making the effective width (W) of the scattering region larger as will be described below.

The process and operation of another embodiment of the method according to the first aspect of this invention will be explained with reference to FIG. 8.

FIGS. 8(a) to (f) correspond to FIGS. 7(a) to (f) respectively. As described above, the projection distance (D) between the centers of the beam spots is 0.8 times a radius of the beam spots. The laser beams $2a, 2b$ has the intensity distribution of the Gaussian beam. When the position (x) is measured by the unit of the radius (r) of the beam spots, and a maximum value of $G_1, G_2$ is 1, the output values $G_1, G_2$ as shown in FIG. 8(c) can be expressed respectively in $$G_1 = \exp[-2(x+0.4)^2]$$

$$G_2 = \exp[-2(x-0.4)^2].$$

Accordingly, the output ratio $G_2/G_1$ is $$\exp\{-2[(x-0.4)^2 - (x+0.4)^2]\}$$

and is expressed in natural logarithm $$\ln(G_2/G_1) = 3.2x.$$

The sum $G_1+G_2$ of the outputs shown in FIG. 8(e) is $$G_1 + G_2 = \exp[-2(x + 0.4)^2] + \exp[-2(x - 0.4)^2],$$

and specifically, when $x = 0$, $G_1 + G_2 = 1.452$, when $x = 0.5$, $G_1 + G_2 = 1.178$, and when $x = 1.0$, $G_1 + G_2 = 0.507$.

The correction coefficient $\zeta$ shown in FIG. 8(f) is given by the same expression for FIG. 7(f).
$\zeta = ([G_1+G_2] \text{ at } x=0)/(G_1+G_2)$, specifically, when $x = 0$, $\zeta = 1$, $\ln \zeta = 0$,
when $x = 0.5$, $\zeta = 1.233$, $\ln \zeta = 0.209$, and when $x = 1.0$, $\zeta = 2.864$, $\ln \zeta = 1.052$.

This embodiment shown in FIG. 8 can measure particle diameters of fine particles precisely through the first to the fourth steps of the embodiment of FIG. 7.

Figure 9:
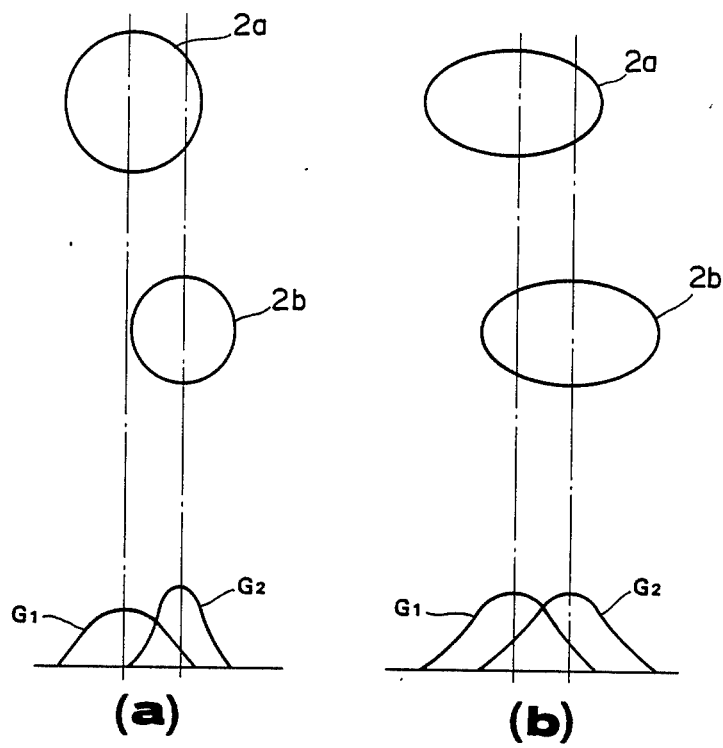
FIG. 9 is an explanatory view of intensity distributions and positional relationships of parallel beams adaptable to the method according to the first aspect.
Figure 10:
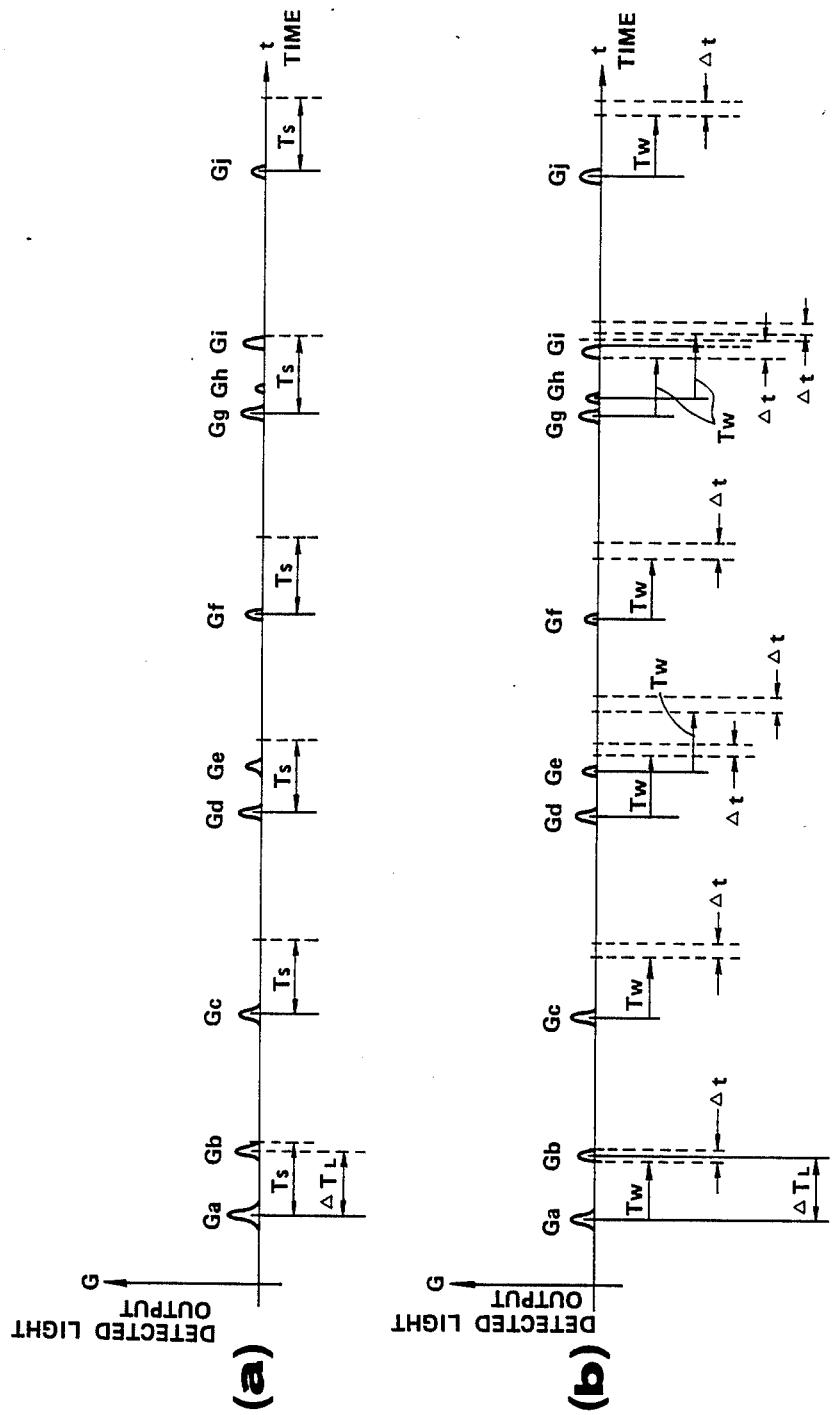
FIG. 10 is explanatory views of extraction of pairs of detected light outputs for the purpose of explaining a first modification of the method according to the first aspect.

The laser beams 2a,2b used in FIGS. 7 and 8 have the Gaussian intensity distribution and have an equal intensity distribution. The fine particle measuring method according to this invention is not limited to those described above. FIG. 9 shows another example of the intensity distribution and the positional relationship of two parallel beams 2a,2b. As shown in FIG. 9(a), the laser beam 2b may be more convergent than the laser beams 2a. As shown in FIG. 9(b), the laser beams 2a,2b may be elliptical. Anyway, the two parallel beams 2a,2b may have any distribution as long as they have intensity distribution gradually increasing over at least the peripheral portion and a portion inner of and near to the peripheral portion inward from the peripheral portions and a suitable correction coefficient $\zeta$ can be set. In the case of uses of such laser beams, correction coefficients are set in accordance with their intensity distributions and positional relationships. Next, a first modification of the system according to the first aspect of this invention will be explained with reference to FIG. 10.

As described above, the system according to the first aspect is based on that the flow speed of a sample fluid is known, and in the second step thereof, a pair of scattered light outputs detected successively at a known time interval are taken as those of one fine particle. This will be explained with reference of FIG. 10(a). When a detected light output $G_a$ is obtained, a next detected light output is monitored before a little longer time interval $T_s$ than a known time interval $\Delta T_L$ has passed, and when a next detected light output $G_b$ is obtained, both outputs are taken as those of one and the same fine particle.

With the methods according to the above described embodiments there is a possibility that two detected light outputs of different fine particles are taken mistakenly for those of one and the same fine particle. Specifically, according to the methods according to the above described embodiments, in FIG. 10(a), a pair of detected light outputs $G_d$ and $G_e$ is taken as those of one and the same fine particle, and in a set of detected light outputs $G_g$, $G_h$ and $G_i$, $G_h$ cannot be identified as that of another fine particle. Accordingly it cannot be denied that errors to some extent occur in the measuring results of the methods according to the above described embodiments, and errors are remarkable especially with samples containing a large number of fine particles.

But the errors are remarkably reduced when the projection distance (L) between two parallel laser beams is as short as about 100 µm. The errors are not substantive and do not destory the value and usefulness of this invention. But when fine particle measurement of very high precision is necessary, the errors will not be ignorable. The first modification of the method according to the first aspect realizes the reduction of the errors.

The method according to the first modification is characterized in that in the second step of the method according to the first aspect, at a given time interval after a predetermined time interval has passed from the time of the detection of a scattered light output, a next scattered light output is monitored. FIG. 10(b) is explanatory of the characteristic process of the method of the modification. The times of generating detected light outputs are identical with those of FIG. 10(a). The time interval for monitoring a next detected light output following one detected light output is indicated by $\Delta t$.

As shown in FIG. 10(b), the monitor is not carried out for a next detected light output until a predetermined time interval $T_w$ has passed from the time of detection of one detected light output $G_a$, and only in the time interval $\Delta t$ following the time interval $T_w$ the monitor is carried out. The time interval $T_w$ is a little shorter than the known time interval $\Delta T_L$, and $T_w+\Delta t$ is a little longer than the known time interval $\Delta T_L$. This arrangement makes it possible to identify one detected light output $G_a$ and a next detected light output $G_b$ as those of one and the same fine particle.

This arrangement prevents mistaking $G_d$ and $G_e$ for those of one and the same fine particle. Besides, when detected light outputs $G_g$ and $G_i$ of one and the same fine particle is followed by a detected light output $G_h$, these three outputs are never mistaken for those of one and the same fine particle. Thus the first modification can greatly reduce measuring errors.

This time interval for the monitor can be set readily by changing a part of the extracting circuit of the embodiments of the method according to the first aspect. That is, the above described extracting circuit, which comprises the clock oscillator, the counter circuit, etc., may include two counter circuits having different pulse widths from each other, and, e.g., an OR gate for giving an OR of the outputs of the two counter circuits. In this case, the pulse width of one of the counter circuits is $T_w$, and that of the other counter circuit is $T_w+\Delta t$. Instead, two kinds of delay circuits may be used, or software of the microprocessor may be used.

Next a second modification of the method according to the first aspect of this invention will be explained.

Figure 11:
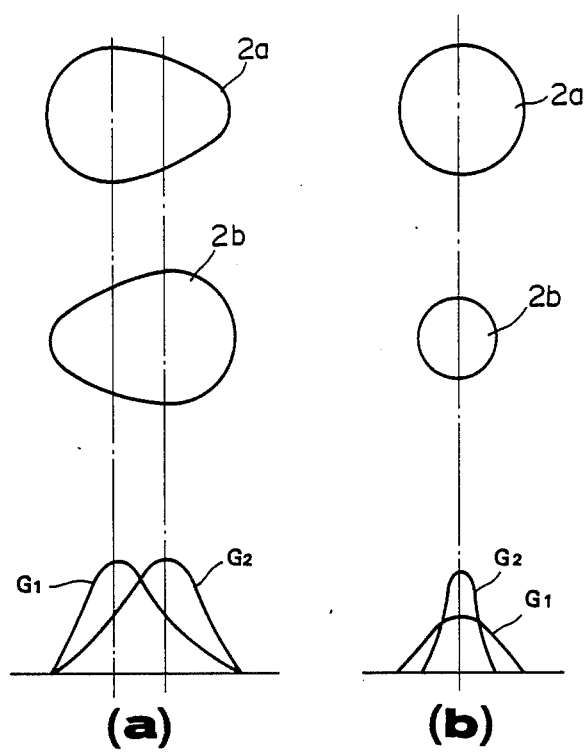
FIG. 11 is explanatory views of intensity distributions and positional relationships of parallel beams of a second modification of the method according to the first aspect.

The main two differences of the second modification from the embodiments are at least two parallel laser beams overlap each other in the flow direction of a sample fluid, and the two laser beams have different intensity distributions. FIG. 11 shows the intensity distributions of the two parallel beams, and their positional relationships. In FIG. 11(a), the laser beams 2a,2b have respectively asymmetrical intensity distributions, and the profiles of their intensity distributions are reverse to each other. In FIG. 11(b), the laser beams 2a,2b are of the Gaussian type but have different convergence from each other. For the beams 2a,2b having such intensity distributions and positional relationships, a ratio between the output values $G_1$, $G_2$ can be given, and the measurement of fine particles can be made in the same process of FIGS. 7 and 8.

Next a third modification of the method according to the first aspect of this invention will be explained.

In the above described embodiments the lengths of the scattering regions 4a,4b are restricted sufficiently small by the diaphragm 9, and the description so far is based on the assumption that the laser beams 2a,2b do not much differ in the intensity distributions and beam spots in their effective light scattering regions 4a,4b. That is, as shown in FIG. 12(a), effective light scattering regions 4a,4b (length $A_1$) has been a small area between $a_1$ and $a_2$ very near to the center $a_o$ of the beam spots, i.e., the area where the beam diameter and the intensities $G_{ao}$,$G_{a1}$ are substantially the same as shown in FIG. 11(b). But in the case the effective light scattering regions 4a,4b are long (length $A_2$ between $a_2$ and $a_2'$) as shown in FIG. 11(a) because of a large diaphragm 9 or the absence thereof, the intensities $G_{ao}$,$G_{a2}$ and beam diameters of the laser beams 2a,2b unignorably differ from each other.

When the effective light scattering regions 4a,4b are so elongated, particle diameters of fine particles cannot be measured based on a maximum value of a pair of detected light outputs or an integrated value (detected light outputs $G_1$, $G_2$). This is because it is considered that when the light scattering regions 4a,4b are restricted sufficiently small, the laser beams 2a,2b effectively scattered in the light scattering regions is identical in the direction of transmission of the laser beams in the light scattering regions. Accordingly the information of the scattering points includes only the directions of the laser beams 2a,2b, and the position of the flow direction of a sample fluid orthogonal to the laser beams 2a,2b (direction of x axis), and only the allowance value $\eta$ corresponding to the the position of the x axis. But when the length of the scattering regions 4a,4b are not restricted, the information of the scattering point has to include not only the postion of the direction of the x axis, but also the positions of the directions of the laser beams 2a,2b (direction (y)). Consequently when the length of the scattering regions 4a,4b in the direction of the laser beams (direction (y)) is not restricted small by the diaphragm 9, it is necessary to define as a new data another variable $\zeta'$ for measuring a width $G_T$ of the detected light output.

Figure 13:
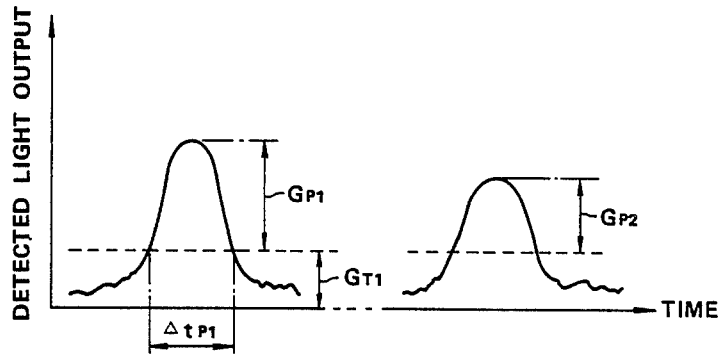
FIG. 13 is an explanatory view of output values and widths of detected outputs of a third modification of the method according to the first aspect.

It is assumed that when one fine particle passes the two laser beams 2a,2b, an detected light outputs as shown in FIG. 13 is obtained. As shown in FIG. 13, the detected light outputs are represented by $G_{p1}$ and $G_{p2}$, and the threshold value and time interval are represented by $G_{T1}$ and $\Delta t_{p1}$. The two variables $\eta,\zeta'$ are given by $$\eta \equiv G_{p2}/G_{p1}$$

$$\zeta' \equiv [\{(\Delta t_{p1}/\Delta T_L)^2 (L/r_{01})^2/(2\ln(G_{p1}/G_{T1}))\} - 1]^{\frac{1}{2}}.$$

The equi $\eta$ lines is substantially parallel with the y axis, and the equi $\zeta'$ line is substantially parallel with the x axis. The orthogonality is not poor. In the above described equations, $\Delta T_L$ represent the time interval between the detected light outputs of one pair, (L), the distance between the two laser beams 2a,2b in the flow direction, and $r_{01}$, the spots diameters of the laser beam generating the detected light output $G_{p1}$.

$G_{T1}$ can be preset, and $(L/r_{01})$ can be predetermined, and when $\Delta t_{p1}$, $G_{p1}$, $G_{p2}$ and $\Delta T_L$ are measured, the variables $\eta$, $\zeta'$ can be given. Then a correction function $F_\phi$ which has been experimentally given is substituted with the variables $\eta$ and $\zeta'$, and a correction coefficient $$\phi = F_\phi(\eta,\zeta')$$

is given. When the correction coefficient $\phi$ is within the allowance range ($\phi_{min} \leq \phi \leq \phi_{max}$), the fine particle is accepted as having passed the effective light scattering regions, and a standard output value $G_{ps}$ is computed based on the correction coefficient. In the case when $G_{p1} = G_{p2}$, $G_{ps} = G_{p1} + G_{p2}$, the standard output value ia $$G_{ps} = \phi \cdot (G_{p1} + G_{p2}).$$

When a maximum value is $G_{p1}$, the standard output value $G_{ps}$ is $$G_{ps} = \phi \cdot (G_{p1}).$$

Then a particle diameter $D_p$ is $$D_p = D_p(G_{ps}).$$

The time interval of a detected light output $\Delta t_{p1}$ may be $\Delta t_{p2}$ for the other detected light output.

Next a fourth modification of the method according to the first aspect will be explained.

In the third modification, in the case the length (A) of the light scattering regions 4a,4b in the direction of transmission of the laser beams (direction (y)) is not restricted by the diaphragm 9, the information of the position in the direction (indicated by (y)) of the laser beams 2a,2b are processed based on the three kinds of actually measured data including the time interval of one detected light output ($\Delta t_{p1}$ or $\Delta t_{p2}$). But in this fourth modification, three laser beams are used, and based on three kinds of actually measured data, the information of the position in the direction (y) is processed.

Figure 14:
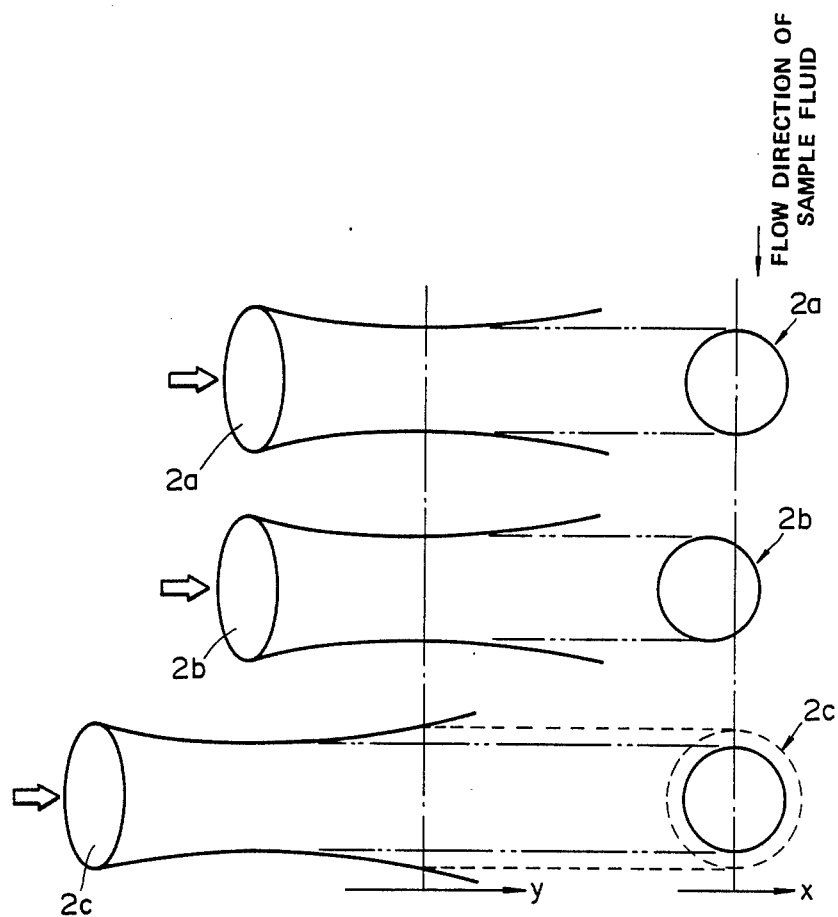
FIG. 14 is an explanatory view of the arrangement of three laser beams of a fourth modification of the method according to the first aspect.

FIG. 14 shows the arrangement of three laser beams 2a,2b,2c. Two laser beams 2a,2b of the three have the center of the beams spots aligned in the direction of transmittance of the laser beams (direction (y)). But the laser beam 2c has the center of the beam spot is not in alignment with those of the laser beams 2a,2b in the direction (y). This arrangement is intended for obtaining the data of the postion in the direction of the laser beam 2c by deflecting the laser beam 2c in the direction (y), because, when the length fo the scattering regions 4a,4b are not restricted by the diaphragm 9, as described in the third modification, the information of the position in the direction (y) is contained in the detected light outputs.

When fine particles pass successively the three laser beams 2a,2b,2c, three detected light outputs $G_{p1}$, $G_{p2}$, $G_{p3}$ are obtained. The detected light output G p3 by the laser beam 2c contains the information of the position in the direction (y).

Then, two variables $\eta$, $\zeta''$ are represented by $$\eta \equiv I\, G_{p2}/G_{p1} \text{ and}$$

$$\zeta'' \equiv G_{p3}/G_{p1}.$$

Then the process for the fourth modification will be explained. Here a standard output value $G_{ps}=[G_{p1}]_{max}$, and a correction coefficient $\phi = G_{ps}G_{p1}$.

First, the detected light outputs $G_{p1}$, $G_{p2}$, $G_{p3}$ are measured, and two variables $\eta$, $\zeta''$ are computed. Then using the correction function F $\phi$, which has been given, a correction coefficient $$\phi = F\phi(\eta, \zeta'') \text{ is given.}$$

Then when the correction coefficient is within the allowance range, ($\phi_{min} \leq \phi \leq \phi_{max}$), the fine particle is accepted as have passed the effective light scattering regions. The other detected light outputs are ignored. next, a standard output value $G_{ps}$ is given by $$G_{ps} = \phi \cdot G_{p1}.$$

Based on the $G_{ps}$, a fine particle diameter $D_p$ is given.

$$D_p = D_p(G_{ps}).$$

SECOND ASPECT OF THE INVENTION

Next, the second aspect of this invention will be explained. The explanation will be centered on the differences from the method according to the first aspect of this invention.

A characteristic of the second aspect of this invention is that the flow speed and flow volume of a sample fluid are also measured directly by laser beam. That is, the first aspect of this invention is based on the flow speed of a sample fluid measured separately by a separate flow meter or kept constant by suitable quantitative sample fluid feeding means (not shown). In the second aspect of this invention, the flow speed and the flow volume of a sample fluid may be unknown. In a first step of the method according to the second aspect, two parallel laser beams are formed similarly to the method according to the first step of the first aspect.

In a second step of the second aspect, fine particles pass the two parallel laser beams, and scattered lights are detected by a suitable light detector as scattered light outputs. The scattered lights are caused in a pair by one and the same fine particle having passed successively both of the two parallel beams $2a,2b$ or are caused singly by one and the same fine particle having passed one of the two parallel laser beams $2a,2b$. The second aspect is based on that the flow speed is unknown, and accordingly it is impossible which fine particle successive scattered light ouputs belong to. In order to identify the successive scattered light outputs a third and a fourth steps are executed.

Figure 15:
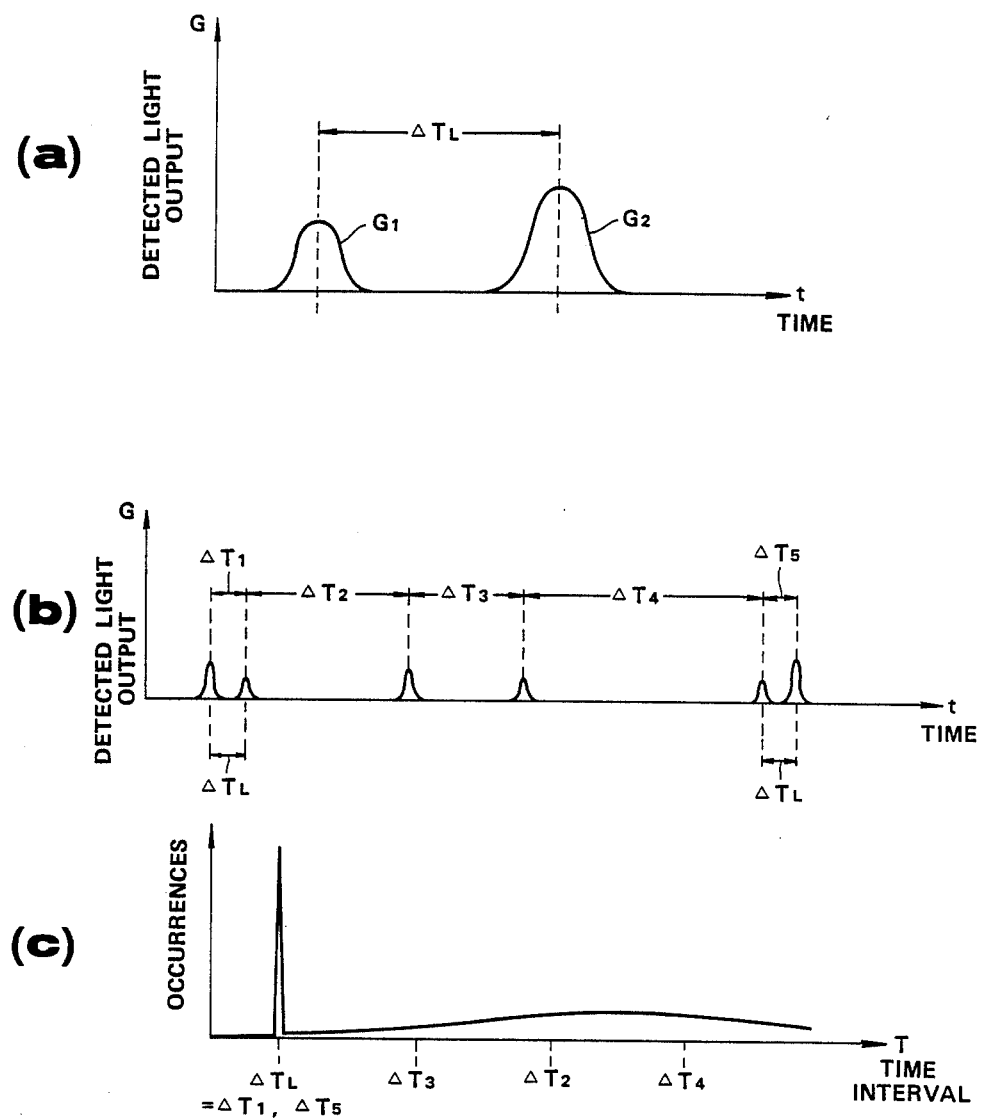
FIG. 15 is an explanatory view of extraction of pairs of detected light outputs of in the method according to the second aspect of this invention.

In the third step, e.g., a maximum time interval between two successive detected light outputs is examined, and based on the maximum time interval a pair of detected light outputs of one and the same fine particle is extracted. The extraction will be explained with reference to FIG. 15. FIG. 15($a$) shows detected light output values $G_1, G_2$ formed when one fine particle passes successively the two parallel laser beams $2a,2b$. A time interval $\Delta T_L$, as described above, is expressed in a function of a flow speed (U) of a sample fluid and a distance (L) between the centers of the laser beams $2a,2b$ as follows $$\Delta T_L = L/U.$$

When L = 100 $\mu$m, and U = 50 cm/sec., the time interval $\Delta T_L$ is about 200 $\mu$s.

FIG. 15($a$) is microscopically shown in FIG. 15($b$). As shown in FIG. 15($b$), a pair of detected light outputs (having noise components removed) generated at the time interval $\Delta T_L$, which are considered to belong to one and the same fine particle appears at two places. If it is assumed that the respective detected light output values $G_1, G_2$ cannot be identified by the light detector, it is impossible which ones of the six output values belong to the laser beams $2a$ or $2b$. But, when the occurrences of the output values $G_1, G_2$ are expressed in terms of the time interval $\Delta T$ as shown in FIG. 15($c$). In other words, when the outputs values $G_1, G_2$ are not discriminated, and the time interval $\Delta T$ between two successive outputs values (G) are processed statistically, a sharp peak appears corresponding to the time interval $\Delta T_L$ for one and the same fine particle. Thus, the time interval $\Delta T_L$ can be easily given by a computing means, e.g., a computer. Then a pair of output values of one and the same fine particle can be extracted.

This process will be explained in more detail.

A projection area of a portion in which effective detected light outputs to be used in the final measurement is represented by a light scattering area (S). For example, when the length of the section (the length in the direction of the laser beams) and the width thereof (the length orthogonal to the laser beams) are 500 $\mu$m and 10 $\mu$m, respectively, the above described light scattering area (S) is $5 \times 10^{-5}$ cm$^2$, and when the flow speed is U = 50 cm/sec., the average time interval for generating detected light outputs only for the laser beams $2a$ is 40 m sec. even when the density of numbers of fine particles in a sample fluid is very high. on the other, a described above, the time interval $\Delta T_L$ for generating detected light outputs for one and the same fine particle is merely about 200 $\mu$s (0.2 m sec). Thus, actually, however, even taking into account detected light outputs generated in an area wider than the light scattering area (S), there is little probability that between detected light outputs of one and the same fine particle, detected outputs of other fine particles are observed for a sample fluid having a usual density of a number of fine particles. Consequently, unless the flow speed (U) in the light scattering regions $4a, 4b$ abruptly changes, a value of the time interval $\Delta T_L$ at a seletived time can be known easily from the measured values of time intervals $\Delta T$ before and after the selected time. In the above described example, since about half of the measured values of the time interval $\Delta T$ are centered around 200 $\mu$s time interval $\Delta T_L$ can be easily given from about 20 measured values of the time interval $\Delta T$.

Besides, the flow speed (U) around the selected time can be easily given from the relationship, $U = L/\Delta T_L$. The value of the projection length (L) can be known or measured beforehand separately.

In a fifth and a sixth step, diameters of fine particles are given. The fifth and the six steps are the same of the third and the fourth steps of the first aspect, and the steps are not explained.

As described above, according to the second aspect of this invention, even when the flow speed of a sample fluid is unknown, the flow speed is given from a peak of the occurrences of the time intervals of the detected light output, and based on the flow speed a pair of detected light outputs of one and the same fine particle can be extracted. Then a fine particle diameter can be measured.

Next, a modification of the second aspect of this invention will be explained. This modification includes the following seventh and eighth steps in addition to the above described first to the sixth steps. In the seventh step, the volume (V) of a sample of fluid passing the effective area of the light scattering region. Here the light scattering area (S) is decided by the length (A) and the effective width (W) of the light scattering regions $4a,4b$ defined by the diaphragm 9 as described in the first aspect, and is expressed by $$S = A \cdot W.$$

On the other hand, the flow speed (U), as described above, is given by $$U = L/\Delta T_L.$$

Then the volume (V) of a sample of fluid passing through the effective area of the light scattering regions is given by $$V = S \cdot U \cdot \Delta T = A \cdot W \cdot L \cdot \Delta T / \Delta T_L.$$

Next, in the eighth step, as one of particle diameter distribution, a density of numbers of fine particles according to particle diameters is given, The density can be computed by particle diameters given by the sixth step, and the volume of a sample fluid given by the seventh step. For example, numbers of fine particles are counted according to particle diameters, and the numbers are divided by a volume (V), and a particle diameter distribution is given in a density of particle numbers according to particle diameters.

The computation of particle diameters is explained by means of the density of numbers of particles according to particle diameters but is not limited thereto. For example, a density may be shown in a frequency density distribution by taking particle diameters successively on the x axis.

THIRD ASPECT OF THE INVENTION

Next, a fine particle measuring system according to a third aspect of this invention will be explained in good detail. As shown in the perspective view of FIG. 16, a single laser beam 22 from a laser beam source 21, e.g., He-Ne laser beam is incident on a small sized rhombic prism PR1 having a half mirror surface 23 to be split into two parallel laser beams $22a,23a$ having the same intensity distribution. The two parallel laser beams $22a,22b$ are formed into images by a small convex lens L1,L2 and further formed into given laser beams $2a,2b$ through afocal optical disposed behind the convex lens L1,L2 and comprising two convex lens L3,L4.

The single laser beam 22 to be emitted from the laser source 21 is of Gaussian type so that the laser beams $2a,2b$ in the light scattering regions $4a,4b$ have an intensity distribution increasing gradually over at least the peripheral portion and a portion inner of and near to the peripheral portion inward from their peripheral portions.

Of the scattered lights formed in all directions from the light scattering regions $4a,4b$, a component headed in a light receiving direction 7 is formed into real images $14a,14b$ through a light receiving lens 8. The real images $14a,14b$ on the diaphragm 9 reach as the component of the scattered light a light detector 10 to be converted into electric signals. The electric signals are supplied to a measuring system, where after noise components are removed from the electric signals by a certain process, the electric signals are used as detected light outputs for fine particle measurement.

The structure and operation of the system according to the third aspect will be explained with reference to FIGS. 17 and 18.

Figure 16:
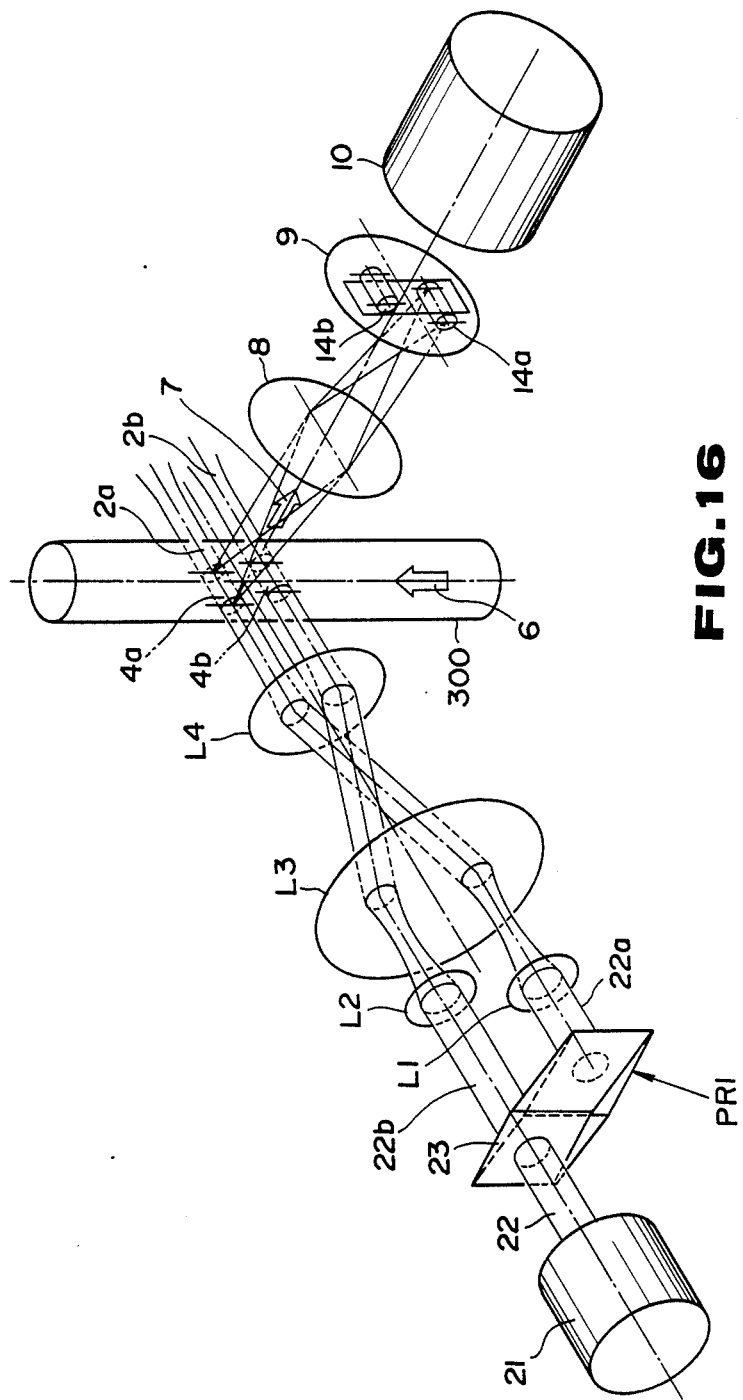
FIG. 16 is a perspective view of a main part of the fine particle measuring system according to the third aspect of this invention.
Figure 17:
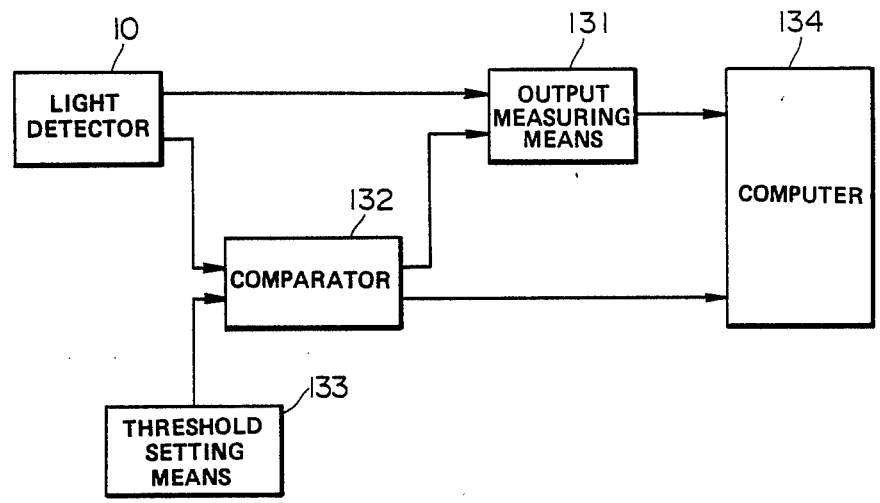
FIG. 17 is a block diagram of the measuring unit of the system according to the third aspect.
Figure 18:
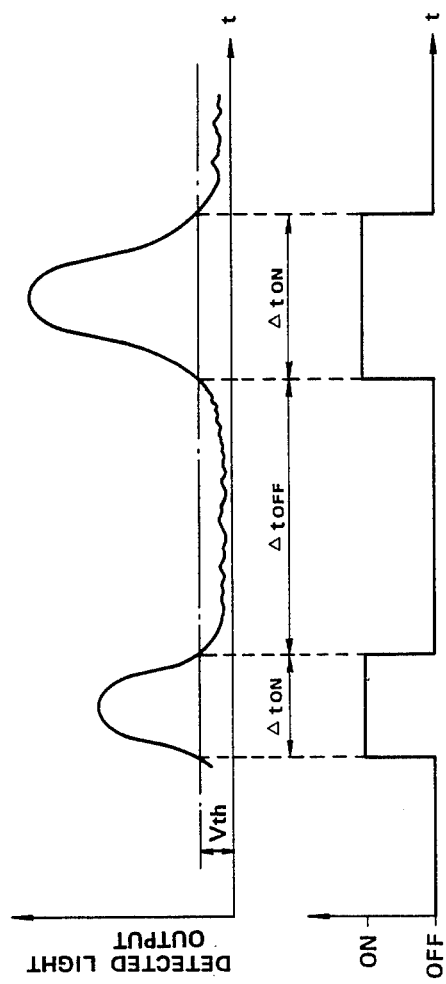
FIG. 18 is an explanatory view of the operation of the measuring unit of FIG. 17.

The output of the light detector 10 also shown in FIG. 16 is supplied to an output measuring means and to a comparator 132, shown in FIG. 17. The comparator 132 has been supplied with a threshold signal $V_{th}$ by a threshold setting means 133. The comparator 132 outputs an ON signal when the threshold signal $V_{th}$ is equal to or higher than an output value (G) of the light detector ($G \geq V_{th}$) and outputs an OFF signal when the former is smaller than the latter ($G < V_{th}$). The ON signal or the OFF signal is supplied to a computer 134 and to the output measuring means 131.

The output measuring means 131 measures the output from the light detector 10 only when it is supplied with an ON signal. Accordingly, the output measuring means 131 measures the outputs of only those (detected light outputs) of the outputs from the light detector 10 which have noise components removed by a threshold value signal $V_{th}$ from the threshold setting means 133. In the case the output measuring means 131 is provided by a peak value of detector, it supplies a maximum value of the detected light outputs (G) to the computer 134. The computer 134 measures and adds continuing times $\Delta t_{ON}$ of ON signals and continuing times $\Delta t_{OFF}$ of OFF signals by a built in clock (not shown). while adding the values of the outputs (detected light outputs) from the output measuring means 131.

Next the function and operation of the fine particle measuring system according to the third aspect.

First a sample fluid is caused to flow in a flow direction 6 in FIG. 16 by sample fluid feeding means. Then the laser beam source 21 is actuated to form two laser beams $2a,2b$. The two beams $2a,2b$ are radiated to fine particles in the sample fluid. At this time, of the scattered lights formed the component thereof headed in the light receiving direction indicated by the arrow 7 is received by the light detector 10 through the light receiving lens and the diaphragm 9 and converted into electric signals (detected light outputs). Then the detected light outputs are processed in the circuit of FIG. 17 and then supplied to the computer 134. Then the computer 134 computes a continuing time $\Delta t_{ON}$ of an ON signal for a detected light output and a continuing time $\Delta t_{OFF}$ of an OFF signal immediately preceeding thereto in response to an ON signal from the comparator 132 and stores the two times and an output value (G) as a set of three data, in a sequential order of their generations.

When the point where a maximum value of an output value (G) generates is a midpoint of the continuing time of an ON signal, a time interval $\Delta t$ from the generation of a current maximum detected output to the generation of an immediately preceding maximum detected output is given by $$\Delta t = \Delta t_{OFF} + (\Delta t_{ON} + \Delta t'_{ON})/2,$$

wherein $\Delta t'_{ON}$ is the continuing time of an immediately preceding ON signal. At the start and the end of a measuring operation, $G = \Delta t_{ON} = 0$.

After data concerning respective detected outputs are substituted with a set of G, $\Delta t_{ON}$ and $\Delta t_{OFF}$, computing operation is executed on them one by one in accordance with the methods according to the first and the second aspects, and various particle diameter distributions are given. Specifically, in the case where the flow speed of a sample fluid is known, when the time interval Δt is less than a given value or within a given range, two detected outputs can be accepted as those of one and the same fine particle, and thus measurement of particle diameters can be made based on two output values (G). Unless the length of the light scattering regions is sufficiently restricted, the measurement can be made based on two output values (G) and a continuing time $\Delta t_{ON}$ of a detected output. When the flow speed of a sample fluid is unknown, a peak of the occurrences of the time interval Δt is given by the computer 134 thereby to extract a pair of detected outputs for one and the same fine particle. Besides, based on computed particle diameters of fine particles and numbers of the fine particles, a density of numbers of fine particles according to particle diameters. In accordance with the method according to the second aspect, frequency density distribution can be given. The processes for these measurements are the same as those for the first and the second aspects, and they are not explained again.

The methods and the system according to the first, the second and the third aspects of this invention are not limited to the above described embodiments, and their various modifications are covered by the first, the second and the third aspects of this invention.

The laser beam source is not necessarily single and may be plural as long as they have the above described intensity distribution. The laser beam source is not necessarily a He-Ne laser beam and may be, e.g., Ar laser beam, semiconductor laser device or others. The laser beam source may be of the linear polarization type. If the laser beam source is of the type, a laser beam can be split in two linear polarized beams having their planes of polarization orthogonal to each other.

The optical system for forming two parallel laser beams may be as shown, e.g., in FIG. 19. The optical system of FIG. 19(a) is the same as that of FIG. 16, and the convex lenses L5 and L6 have the beam reducing arrangement.

Figure 20:
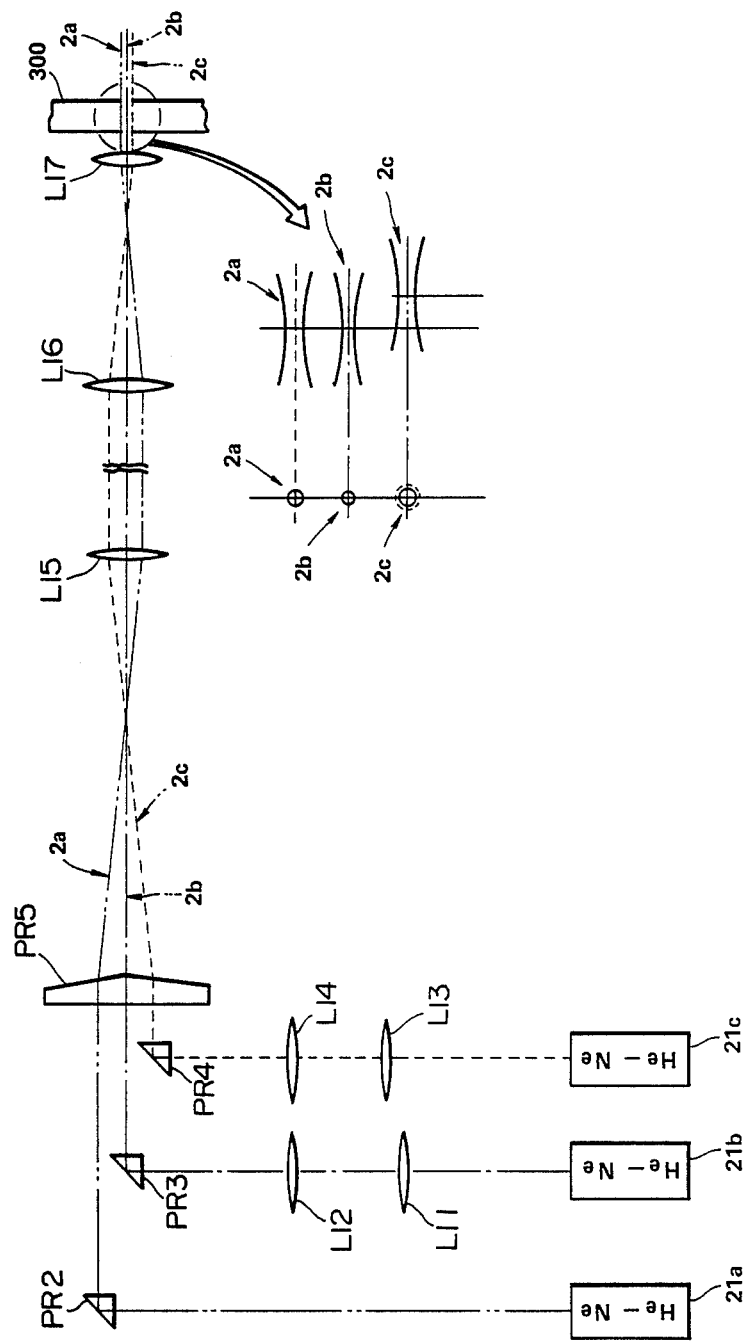
FIG. 20 is explanatory views of the optical system for forming three parallel laser beams.

Three parallel laser beams are formed by, e.g., the optical system of FIG. 20. In FIG. 20(a), the laser beam source has three He-Ne laser beam sources 21a,21b,21c. The laser beams 2a,2b,2c emitted from the respective sources 21a,21b,21c are reflected on their associated total reflecting prisms PR2,PR3,PR4, then have their optical paths adjusted by a optical path adjusting prism PR5, and then radiated onto a flow passage 300. Of the lenses L1 to L17, lenses L11, L12 are for reducing spot diameters, and accordingly the spot diameter of the laser beam 2b is made smaller than that of the laser beam 2a as shown in FIG. 20(b). The lenses L13,L14 are used for adjusting spot positions, and accordingly the position of the spot of the laser beam 2c differs from the positions of the spots of the laser beams 2a,2b. This invention may use any lens system as long as it can form parallel laser beams having equal intensity distributions described and may partially include reflecting mirrors or prisms, or optical transmission passages, such as optical fibers.

The structure of the measuring unit is not limited to that of FIG. 17 and has various modifications. When three laser beams are used, the measuring system may be used by changing the software of the computer. The time intervals between detected outputs (e.g., detected light outputs) is given by the time interval between maximum values of detected outputs but may be the time interval between the rise times of detected outputs.

The methods and system according to the first to the third aspects of this invention are characterized in that the spots of at least two parallel laser beams are spaced from each other by a certain distance in the flow direction of a sample fluid. In contrast to them, the methods and the systems according to the fourth to the seventh aspects of this invention are characterized in that two laser beams are linear polarized laser beams having their planes of polarization orthogonal to each other, and their beam spots at least partially overlap each other. But the selection of an effective area of the light scattering regions, and correction of detected outputs are substantially the same in the technical idea as those of the method and the system according to the first to the third aspects. The methods and the systems according to the fourth to the seventh aspects will be explained with respect to the points which are not common with those according to the first to the third aspects of this invention.

FOURTH ASPECT OF THE INVENTION

Next, the fine particle measuring method according to a fourth aspect of this invention will be explained.

Figure 21:
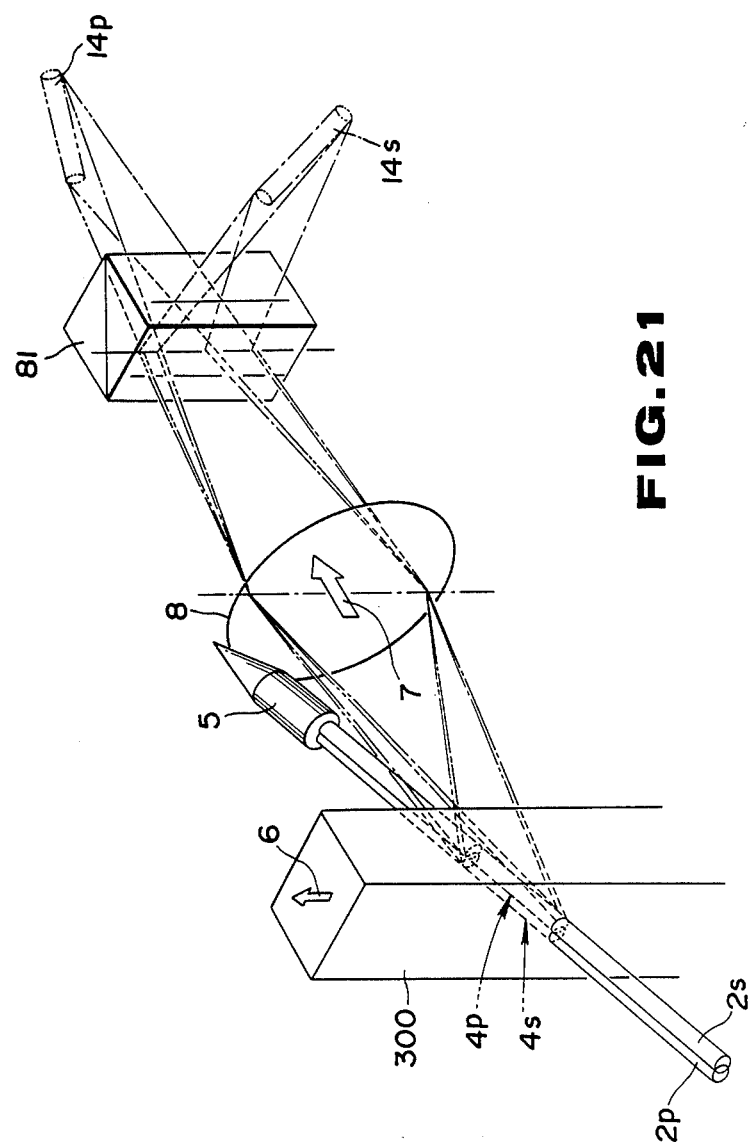
FIG. 21 is a perspective view of a main portion of the optical system in the method according to the fourth aspect of this invention.

As shown in FIG. 21, the laser beam used in the method according to the fourth aspect is provided by two parallel linear polarized laser beams 2p,2s. The electric field oscillation planes of the respective linear polarized laser beams 2p,2s are in the horizontal and the vertical directions. Their beam spots are polarized from each other by a given distance in the direction orthogonal to the flow direction of a sample fluid 6 and in the direction orthogonal to the direction of the laser beams 2p,2s. The two linear polarized laser beams 2p,2s have substantially the same intensity distribution (preferably completely the same), and their spot diameters are substantially the same (preferably completely the same). A flow passage member (flow cell) in the form of a column of rectangular section orthogonally to the linear polarized laser beams 2p,2s at a position where the beam spots of the two laser beams are the smaller (at a beam spot position). A sample fluid flows in the flow direction indicated by the arrow 6 through a flow passage 300 in the flow passage member.

Since the planes of polarization of the linear polarized beams 2p,2s are orthogonal to each other, the physical optical interference between the two beams is insignificant, and the overlapping of their beam spots is insignificant. This method is based on that the flow speed of a sample fluid is known as will be described below, and a flow meter or a quantitative sample fluid feed pump, for example, is provided to obtain a known flow speed. In FIG. 21, reference numeral 5 indicates a beam trap.

The fine particles in a sample fluid radiated by the linear polarized laser beams 2p,2s disperse the laser beams in accordance with the Mie's light scattering theory. The scattered lights are stronger in the direction orthogonal to the electric field oscillation plane of the beams and in the forward direction depending on particle diameters. A part of the near forward scattered lights (in the direction of a light receiving direction) are formed at given image points in real images 14p,14s of light scattering regions corresponding to the linear polarized laser beams through a linear polarized beam splitter 81 arranged with the right receiving surface orthogonal to a right receiving lens 8 and the right receiving direction 7. The split lights are called p and s polarized light components hereinafter. A suitable diaphragm (not shown) is provided near the image points or the linear polarized beam splitter 81, and the aperture (light receiving window) restricts the lengths of the real images 14p,14s of the light scattering regions to be measured. Accordingly the lengths of the light scattering regions 4p,4s are restricted. It is as described in the method according to the first aspect that the restriction of the lengths of the light scattering regions 4p,4s is very significant in measuring particle diameters.

The real images 14p,14s having the lengths restricted by the diaphragm are detected as scattered light outputs corresponding to the p and s polarized light components by two light detectors (e.g., a photomultiplier), where they are converted to electric signals. The electric signal are subjected to the same process described in the method according to the first aspect and sent to a computer or others not shown for the measurement of particle diameters or others.

Next, the process and function of embodiments of the method according to the fourth aspect of this invention.

Figure 22:
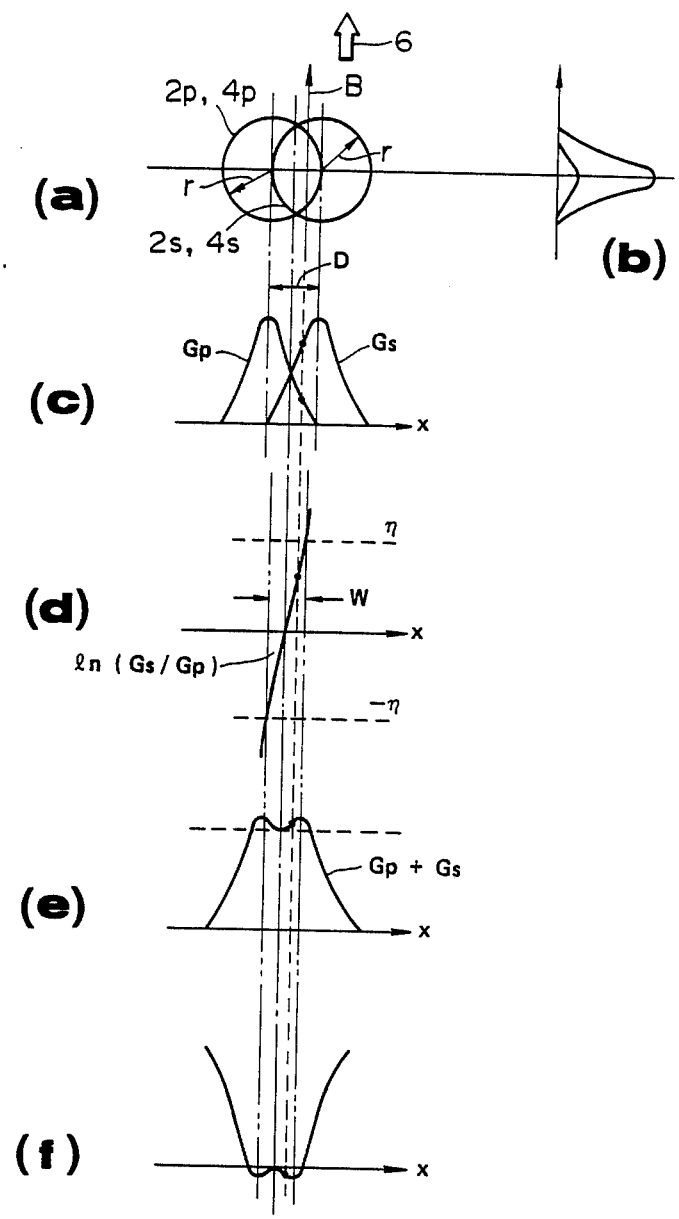
FIGS. 22 and 23 are explanatory views of the operation of an embodiment of the method according to the fourth aspect.

FIG. 22 shows an explanatory view of the embodiment. FIGS. 22(a) to (f) correspond to FIGS. 7(a) to (f).

In FIG. 22(a), (r) represents the radius of the spots of the linear polarized laser beams 2p,2s, and (D) denotes the projection distance in the orthogonal direction to the flow direction 6. When fine particles pass the spots of the linear polarized laser beams 2p,2s in the direction indicated by the arrow (B), the intensity distribution shown in FIG. 22(b) is obtained. The output value (G) to be used in computing particle diameters varies depending on the position where the fine particles pass, i.e., the position where the axis (x axis) orthogonal to the flow passage and the laser beams and flow line. FIG. 22(c) diagrammatically shows how the output value $G_p$ of the linear polarized laser beam 2p passing the light scattering region 4p and the output value $G_s$ of the linear polarized laser beam 2s vary, depending on the position of the passing position (x) of fine particles. When fine particles pass the midpoint between the linear polarized laser beams 2p and 2s (x=0), the output value is $G_s/G_p=1$ as shown in FIG. 22(d). When they pass the point deviating to the right from the midpoint (x>0), the output value is $G_s/G_p$ 1 as shown in FIG. 22(d). As described with reference to FIG. 7, $G_s/G_p$ can be made higher with the above described right deviation amount by using linear polarized laser beams, e.g., Gaussin type beam, having a suitable intensity distribution. When fine particles pass the point deviating to the left from the midpoint (x<0), $G_s/G_p$ can be made lower than 1 with the leftward deviation amount.

The sum of the output value $G_p$ of the linear polarized laser beams 2s, and that of the linear polarized laser beam 2p is as shown in FIG. 22(e). In the same way as described above with reference to FIG. 7, based on the sum of outputs values $G_p+G_s$ of the two linear polarized beams 2p,2s at the midpoint (x=0) therebetween, and output values $G_p+G_s$ at various points, a correction coefficient is given by $$\zeta=([G_p+G_s] \text{ at } x=0)/(G_p+G_s).$$

Corrections can be made using a correction coefficient thus given.

The process of measuring particle diameters of the method according to the fourth aspect described above.

In a second step, based on a coincidental occurrence of detected outputs of scattered outputs, a pair of detected outputs is extracted for one and the same fine particle. Since one particle passes the effective light scattering regions, two detected outputs are generated substantially coincidentally, a pair of detected outputs can be extracted on their coincidental occurrence. Accordingly it is not necessary to provide the extracting circuit used in the system according to the third aspect.

In a third step, a ratio between the values of a pair of detected outputs given in the second step are examined. That is, pairs of detected outputs having ratios between the detected output values of the respective pairs which are with respect to an allowance value $$-\eta<\ln(G_s/G_p)<\eta$$

are selected, and an area of the light scattering regions 4p,4s to be detected is selected. An allowance value $\eta$ and an effective length (W) of the light scattering regions are set in the same way as described above with reference to FIG. 7.

In a fourth step, a particle diameter $D_p$ is computed. The computation uses a pairs of outputs values $G_p,G_s$ selected in the second and the third steps. When the effective width (W) of the light scattering regions is restricted, the radiation amount to fine particles becomes constant, where, when $G_p+G_s=H_o'$, the particle diameter $D_p$ is expressed in a function of $H_o$ by $$D_p=F(H_o).$$

Then the same correction as described above in the method according to the first aspect is made, and the effective area (S) can be made, the required measuring time being made shorter.

Figure 23:
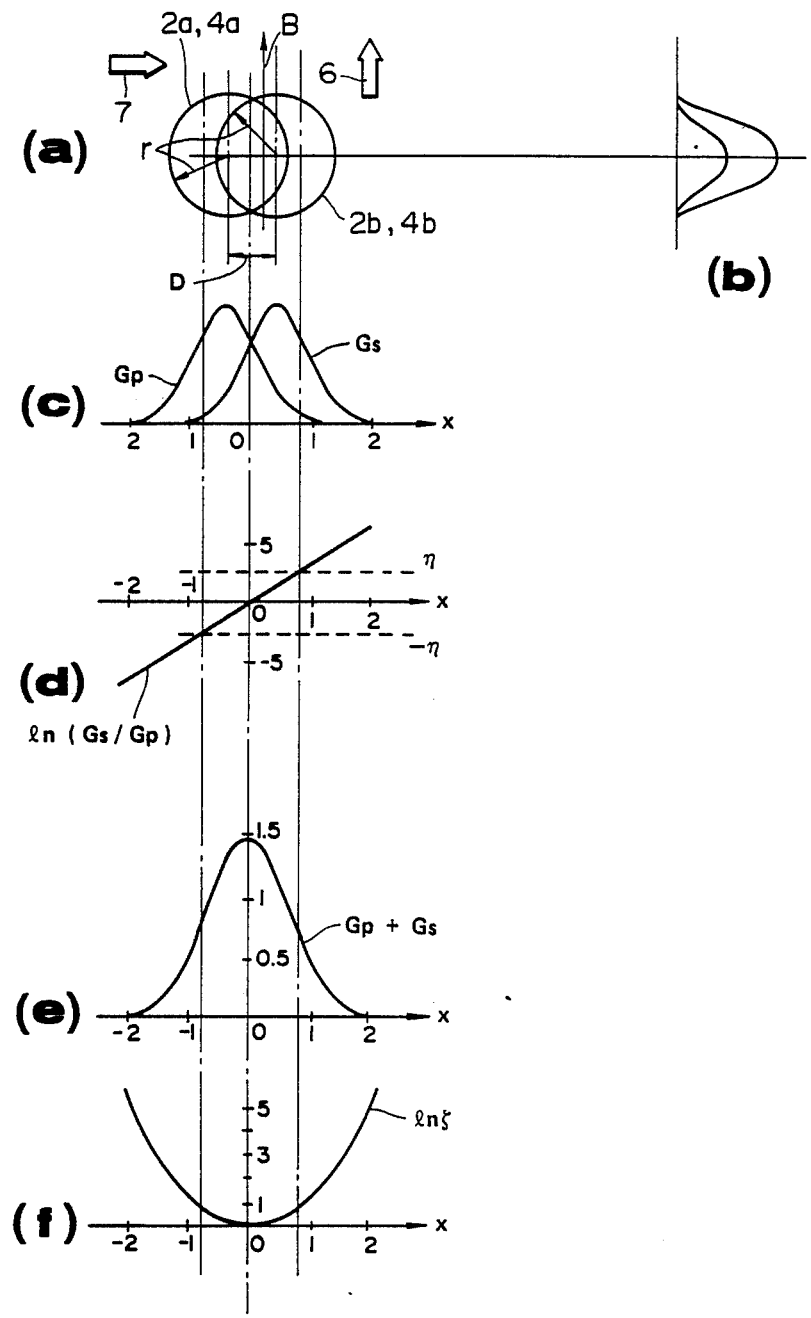

The function and the measuring method shown in FIG. 22 are for the case the deviation amount (projection distance (D)) between the centers of the two linear polarized laser beams 2p,2s is equal to or a little larger than the radius (r) of the beam spots. FIG. 23 shows the case the deviation amount (D) between the centers of the two laser beam 2p,2s is smaller than the radius (r) of the beam spots. FIG. 23 shows another embodiment in which the deviation amount (D) between the centers of the two laser beams 2p,2s is smaller than the radius (r) of the beam spots (specifically, D=0.8r). The embodiment of FIG. 23 has the advantage that the effective width (W) of the light scattering regions can be made larger.

Since FIGS. 23(a) to (f) corresponding to FIGS. 8(a) to (f) respectively, their detailed description is not made.

Figure 24:
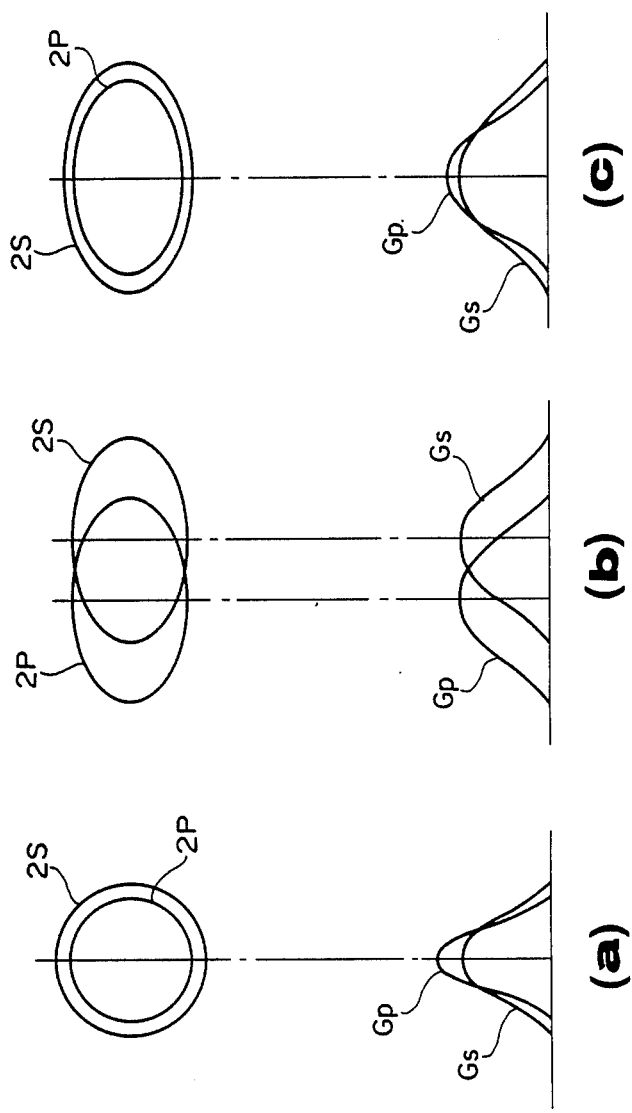
FIG. 24 is explanatory views of intensity distributions and positional relationships of linear polarized beams adaptable to the method according to the fourth aspect.

The linear polarized laser beams 2p,2s have Gaussian distribution and have substantially the same intensity distribution. The measuring process of the method according to the fourth aspect is not limited to the above. FIG. 24 shows a further another embodiment in which the intensity distribution and positional relationship of the two linear polarized laser beams 2p,2s. That is, as shown in FIG. 24(a), the linear polarized beam 2p may have a higher convergence than the linear polarized beam 2s. As shown in FIG. 23(b), the linear polarized laser beams 2p.2s may have an elliptical shape. As shown in FIG. 23(c), the linear polarized laser beams 2p,2s may be elliptical beams having different convergences and overlapped.

Figure 25:
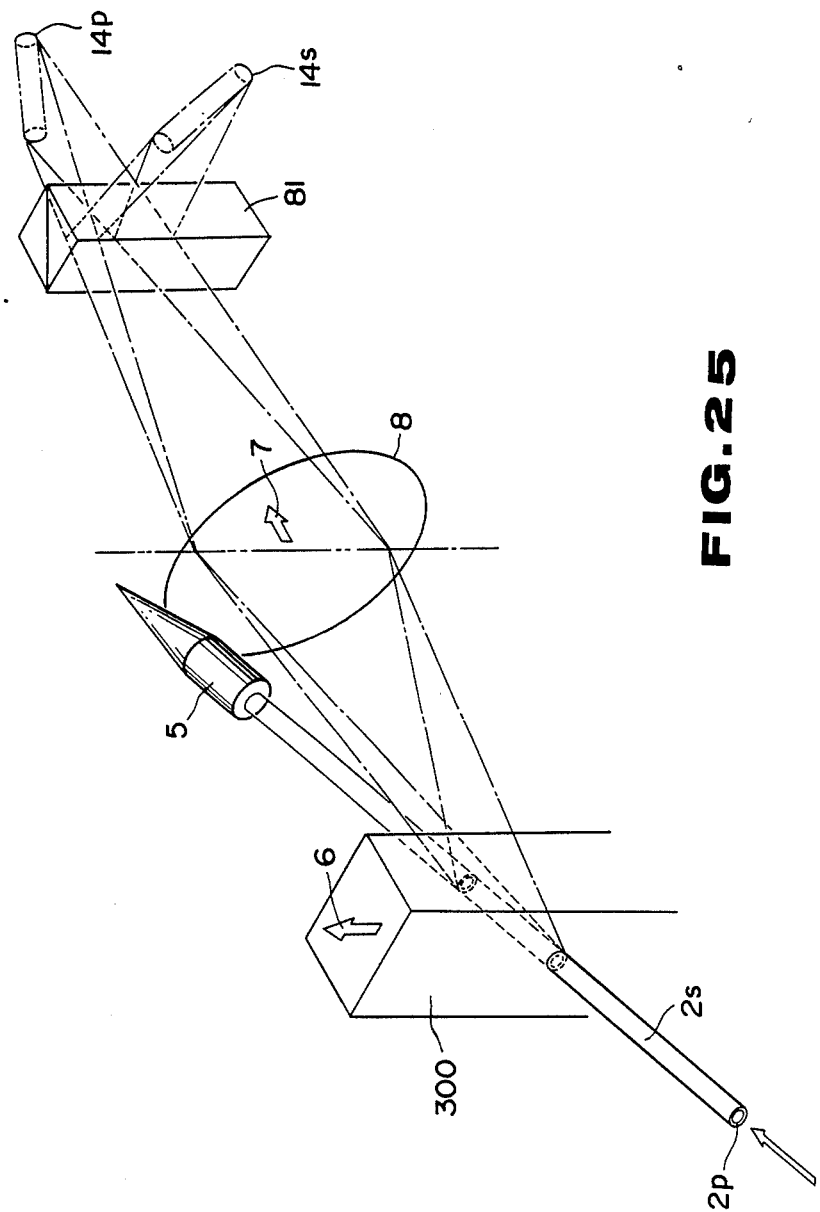
FIG. 25 is a perspective view of a main part of the optical system for the linear polarized beam of FIG. 24(b)

FIG. 25 shows the main part of an optical system for the linear polarized laser beams 2p,2s of FIG. 24(a). As shown in FIG. 25, detected outputs of one and the same fine particle are generated coincidentally, and the detected outputs are split into the p polarized component and the s polarized component to be detected separately. In FIG. 25, reference numeral 5 indicates a beam trap.

Next a first modification of the method according to the fourth aspect of this invention will be explained.

The above described embodiments are based on that the length of the light scattering regions $4p,4s$ are restricted so small by the diaphragm that the the linear polarized laser beams $2p,2s$ have no large differences in the intensity distribution and the beam as described above with reference to FIG. 12, in the case the effective areas of the light scattering regions $4p,4s$ are long because of a large diaphragm or the absence of the diaphragm, the intensity and beam diameter of the linear polarized beams $2p,2s$ is different between their central portions (spot positions) and their peripheral portions.

As described in the method according to the first aspect, unless the light scattering regions $4p,4s$ are restricted small by the diaphragm, another new variable is defined, and a time width $\Delta t_{pp}$ of a detected output is computed as a new data.

Figure 26:
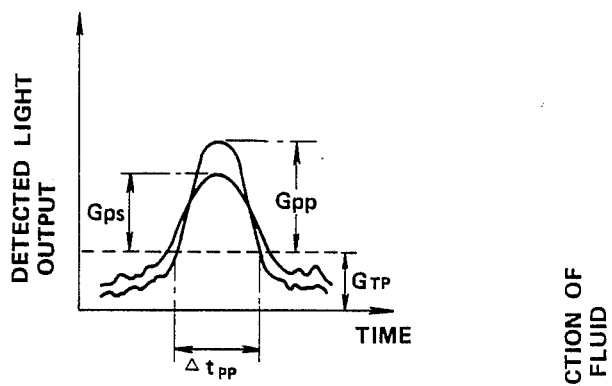
FIG. 26 is an explanatory view of output values and widths of detected outputs of a first modification of the method according to the fourth aspect.

It is assumed that when fine particles pass two linear polarized laser beams $2p,2s$, detected light outputs shown in FIG. 26 are obtained. As shown in FIG. 26, the detected light outputs are represented by $G_{pp}, G_{ps}$, and a threshold value and a time width are denoted by $G_{Tp}$, and $\Delta t_{pp}$. Two variables are given by $$\eta = G_{ps}/G_{pp}$$

$$\zeta' = [\{(\Delta t_{pp} \cdot U/r_{op})^2/(2\ln(G_{pp}/G_{Tp}))\} - 1]^{\frac{1}{2}}.$$

Then, this results in the same described in the method according to the first aspect. That is, when it is defined that when $G_{pp} = G_{ps}$, $G_{sT} = G_{pp} + G_{ps}$, the standard output value $G_{sT}$ is $G_{sT} = \phi \cdot (G_{pp} + G_{ps})$. When a maximum value of $G_{pp}$ is $G_{sT}$, the standard output value $G_{sT}$ is $G_{sT} = \phi \cdot G_{pp}$. Then the particle diameter $D_p$ is given by $$D_p = D_p(G_{sT}).$$

Instead of the time width $\Delta t_{pp}$ of the detected light output, $\Delta t_{ps}$ of the detected light output of the other linear polarized laser beam $2s$ may be used.

Next, a second modification of the method according to the fourth aspect of this invention will be explained.

In the first modification, in the case the length of the light scattering regions $4p,4s$ is not especially restricted by the diaphragm 9, the time interval ($\Delta t_{pp}$ or $\Delta t_{ps}$) of one of the detected light outputs is measured to prepare three actually measured data, and the information of the positions in the direction of the linear polarized beams $2p,2s$ (y direction) are processed. In the second modification, however, three laser beams are used to prepare three actually measured data, and the information of the position in the y direction is processed.

Figure 27:
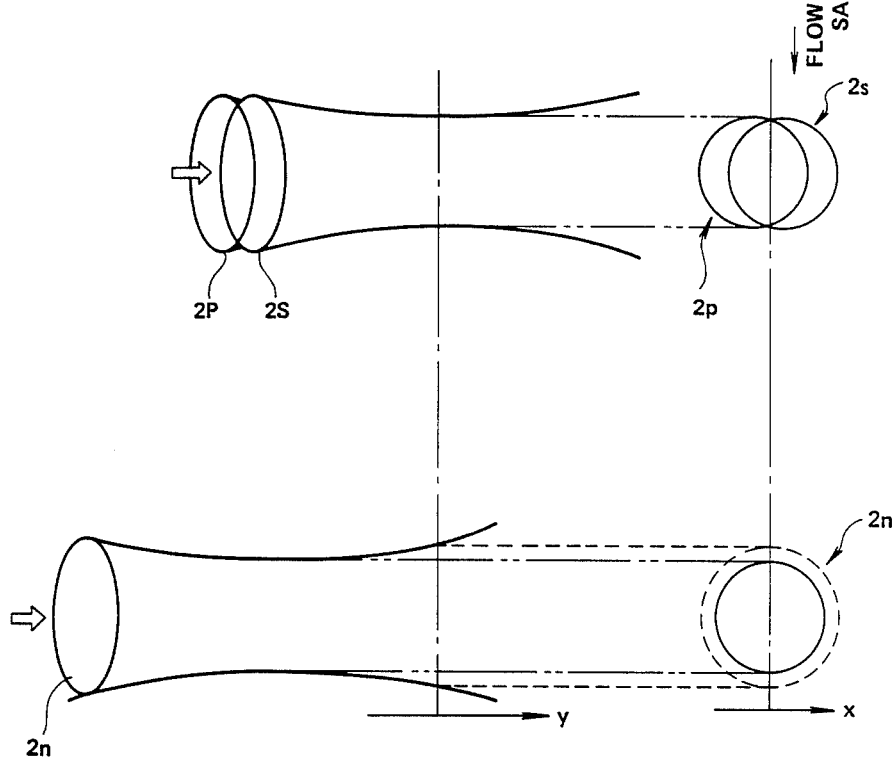
FIG. 27 is an explanatory view of the arrangement of three laser beams of a second modification of the method according to the fourth aspect.

FIG. 27 shows the arrangement of two linear polarized laser beams $2p,2s$, and an unpolarized random polarized beam $2n$. The centers of the beam spots of the two linear polarized beams $2p,2s$ coincide in the direction of the beams (y direction), but the center of the beam spot of the third random polarized beam $2n$ does not coincide with the centers of the beam spot of the linear polarized beams $2p,2s$.

When fine particles pass successively the three laser beams $2p$-$2n$, three detected outputs $G_p, G_s$ and $G_n$ are obtained. The detected light output $G_n$ of the random polarized laser beam $2n$ contains the information of the positions in the y direction.

When two variables $\eta, \zeta''$ are defined as follows:

$$\eta = G_s/G_p$$

$$\zeta'' = G_n/G_p,$$

what is described in the method according to the first aspect of this invention with reference to FIG. 14 takes place.

In the second modification, three detected outputs have to be identified for one and the same fine particle. To this end, the flow speed of a sample fluid has to be measured separately by a flow meter or others, the sample fluid has to be caused to flow at a constant speed by a sample fluid feed pump (not shown), or a passing speed of fine particles (passage time) has to be measured directly (by a laser beam).

Next a method of identifying a pair of detected outputs when the flow speed of a sample fluid is known will be explained.

When the flow speed of a sample fluid is known, since the projection distance (L) between the centers of the linear polarized beams $2p,2s$ and the center of the random polarized laser beam $2n$ is decided, the value of the time interval between the passage times of the sample fluid is estimated by the value of the flow speed. Under these conditions, when fine particles in a sample of fluid pass the linear polarized laser beams $2p,2s$ and the random polarized beam $2n$ are dispersed into stronger scattered lights in the direction of the plane orthogonal to the electric field oscillation planes of the beams $2p,2s$ mainly including the forward direction and its vicinity, and the random polarized laser beam $2n$ is dispersed in scattered lights in every direction including the forward direction of the beam and its vicinity. The scattered lights thus formed are split by polarized beam dividing means, e.g., a linear polarized beam splitter, then are detected as scattered light outputs by a light detector (not shown), then converted into electric signals, and then supplied to a measuring unit (not shown), where the second step of the method according to the fourth step.

When fine particles pass only either one of the linear polarized laser beams $2p,2s$ and the random polarized laser beam $2n$, detected outputs are not obtained successively at a known time interval (time interval between passage times $\Delta T$) given only by the flow speed (U) and the projection distance (L). Accordingly, if an extraction circuit for extracting a pair of detected outputs (detected light outputs having noise components removed) at a given time interval is provided, the detected outputs which have passed only either one of the beams are excluded as detected outputs not to be measured. The same extracting circuit as described in the method according to the first aspect can be used.

Even if the extracting circuit is provided, when fine particles enter the light scattering regions continuously, two detected outputs of different fine particles are extracted erroneously as those of one and the same fine particle. It cannot be denied that measuring results of the above described process contain some errors and remarkable errors especially when a sample fluid contains many fine particles. In such case, pairs of detected outputs are extracted in the same way as in the method according to the first aspect with reference to FIG. 10.

In place of the the random polarized laser beam $2n$, a laser beam which has other polarization characteristics, e.g., linear polarization characteristics may be used. When the flow speed of a sample fluid is unknown, pairs of detected outputs are identified in the way which will be described below in the method according to a fifth aspect of this invention.

FIFTH ASPECT OF THE INVENTION

Next, the fine particle measuring method according to a fifth aspect of this invention will be described with respect to the differences from the method according to the fourth aspect.

The characteristic of the method according to the fifth aspect is the same as that of the method according to the second aspect. That is, the flow speed of a sample fluid is measured directly by laser beams, then based on the flow speed the volume of passing sample fluid is given, and based on the measured particle diameters and the volume of passing sample fluid, particle diameter distributions are given. Besides, the method according to the fifth aspect is that the laser beam is made up with two linear polarized beams and a third parallel beam, and the flow speed and the volume of a sample fluid may be unknown.

In a first step of the method according to the fifth aspect, two linear polarized beams $2p,2s$, and one parallel laser beam $2n$ are formed. The positional relationships among the beam spots of the laser beams are as shown in FIG. 28(a). As in the method according to the fourth aspect, the two linear polarized beams deviate from each other by a distance (D) in the directions orthogonal to the direction of the beams and the flow direction of a sample fluid, in a range in which the beam spots of the laser beams overlap each other. The third laser beam $2n$ deviates from the two linear polarized laser beams in the range where the two linear polarized laser beams $2p,2s$ overlap each other and in the flow direction of the sample fluid by a distance (L). It is necessary that the distance between the centers of the beam spots $(L^2 + D^2/4)^{\frac{1}{2}}$ is as large as no physical optical interference takes place with each other. The projection distance (L) has to be as large as the time interval between the passage times can be measured.

In a second step, scattered lights formed by fine particles passing the two linear polarized laser beams and the one parallel laser beam are divided into polarized components to be detected by a suitable light detector. The scattered lights include those formed continuously by one and the same fine particle passing successively the two linear polarized beams $2p,2s$ and the one parallel beam $2n$ (FIG. 28(b)) and those formed singly by fine particles passing only the outer peripheral portion of one of the two linear polarized beams. But the method according to the fifth aspect is based on that the flow speed of a sample fluid is unknown, and thus continuously generated scattered lights cannot be identified as to which fine particle they belong to. Then a third and a fourth steps are executed in the same way of those of the method according to the second aspect.

In the third step, the time interval between, e.g. the maximum values of two continuous detected outputs is examined, and based on the given time interval, a pair of detected outputs of one and the same particle is extracted. Here, when the third parallel beam $2n$ is a random polarized beam (p and s polarized beams $2p,2s$ are linear polarized beams), the scattered lights formed by fine particles passing the third parallel beam contain both the p and s polarized components. Accordingly, as shown in FIG. 28(b), the detected light output $G_n$ of the parallel beam $2n$ is detected by the light detector as detected light outputs $G_{np}, G_{ns}$ according to the two polarized components. This will be explained with reference to FIG. 29 by means of an example of the time interval of the detected light outputs given by the light detector for the p polarized light detection.

FIG. 29(a) shows the values of the detected light outputs $G_{pa}-G_{pe}$, $G_{sa}-G_{se}$, $G_{na}-G_{ne}$ generated by fine particles (a)-(e) passing successively the two linear polarized beams $2p,2s$, and the parallel beam $2n$. As described above, the time interval $\Delta T_L$ is expressed in a function of the flow speed (U) of a sample fluid and the distance between the centers of the linear polarized beams $2p,2s$ and the center of the parallel beam $2n$ by $$\Delta T_L = L/U.$$

As shown in FIG. 29(c), pairs of detected light outputs (having noise components removed) of the p polarized component which appear to be of the one and same fine particle appear at the time interval $\Delta T_L$ at three positions. In the detected outputs of the fine particle (e) the pair to the p polarized component is absent (i.e., the fine particle (e) has passed only the linear polarized beam $2s$. The pair of the detected outputs of the fine particle (e) is eliminated from the detection. When it is assumed that the output values $G_{pa}-G_{pc}$ and $G_{na}-G_{nc}$ cannot be identified by the light detector, it is impossible to identify which ones of the above described six output values is $G_{pa}-G_{pc}$ of the linear polarized beam $2p$ and $G_{na}-G_{nc}$ of the parallel beam $2n$. But the occurrences of the these output values are expressed in terms of the time interval $\Delta T$ as shown in FIG. 29(b). That is, even when all the output values are not classified but combined, when the time interval between two successive output values (G) is processed statistically, a sharp peak appears corresponding to the time interval $\Delta T_L$ for one and the same fine particle. Thus computing means, e.g., a computer, can identify the time interval $\Delta T_L$ easily and extract a pair of output values of one and the same fine particle. This is specifically explained in the method according to the second aspect with reference to FIG. 15.

In FIG. 29(a), concerning the fine particle (b), the pair of detected light outputs $(G_{pb}, G_{nb})$ of the the p polarized component appear, but no pair of the s polarized component appears. Then it is necessary to omit the pair from the detection. In order to omit the pair, for example, the following two processes are used.

A first one of the two processes, a pair of detected outputs is extracted based on a peak of occurrences of the time intervals, and then coincidence of the detected outputs generated by fine particle passing the linear polarized beams $2p,2s$ is judged. In the second one of the two processes, a pair of detected outputs of the p polarized component is extracted based on the time interval, while a pair of the s polarized component is extracted based on the time interval, and the extracted results of both pairs are compared to use them as a final extracted results.

In a fifth and a sixth steps, particle diameters of the fine particles are given. The fifth and the sixth steps are the same as the third and the fourth steps of the second modification of the method according to the fourth aspect, and thus their explanation is omitted. In the method according to the fifth aspect, even when the flow speed of a sample fluid is unknown, the flow speed is measured based on a peak of occurrences of a time interval of detected outputs, and based on the given flow speed a pair of detected outputs of one and the same fine particle can be extracted. Then particle diameters of fine particles can be measured.

The method according to the fifth aspect includes the following seventh and the eighth steps in addition to the above described first to the sixth steps. That is, in the seventh step, the volume (V) of the sample fluid which has passed an effective areas of the light scattering regions are given. As described in the method according to the fourth aspect, a light scattering area (S) is decided by the length (A) of a light scattering regions $4p,4s$ and the effective width (W) thereof by the following expression $$S = A \cdot W.$$

On the other hand, the flow speed (U) is given by $$U = L/\Delta T_L,$$

and thus the volume (V) of a sample fluid in the time interval $\Delta T$ is given by $$V = S \cdot U \cdot \Delta T = A \cdot W \cdot L \cdot \Delta T / \Delta T_L.$$

Next, in the eight step, a density of numbers of fine particles according to particle diameters is given. The density is given based on the particle diameters given by the sixth step, and the volume of a sample fluid computed by the seventh step. For example, numbers of fine particles according to particle diameters are added, and the sum is divided by a volume given beforehand to give a particle diameter distribution in the form of a density of numbers of fine particles according to particle diameters.

Particle diameters are computed, for example, in a density of numbers of fine particles according to particle diameters, but similarly to the method according to the second aspect, particle diameters may be given in a density by measuring particle diameters on the horizontal axis or may be given in frequency density distributions by measuring particle diameter divisions or particle diameters on the horizontal axis.

Figure 28:
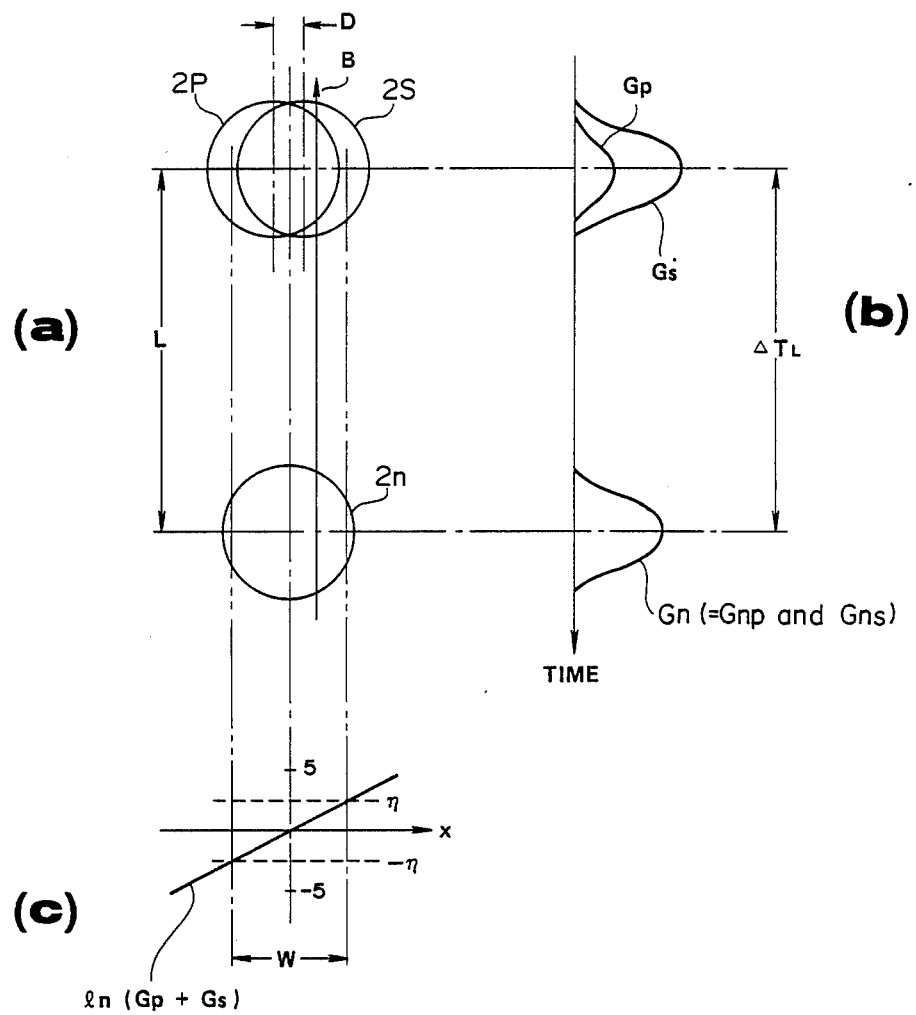
FIG. 28 is explanatory views of the arrangement of beam spots and detected light outputs of the method according to the fifth aspect of this invention, where three beams are used.
Figure 29:
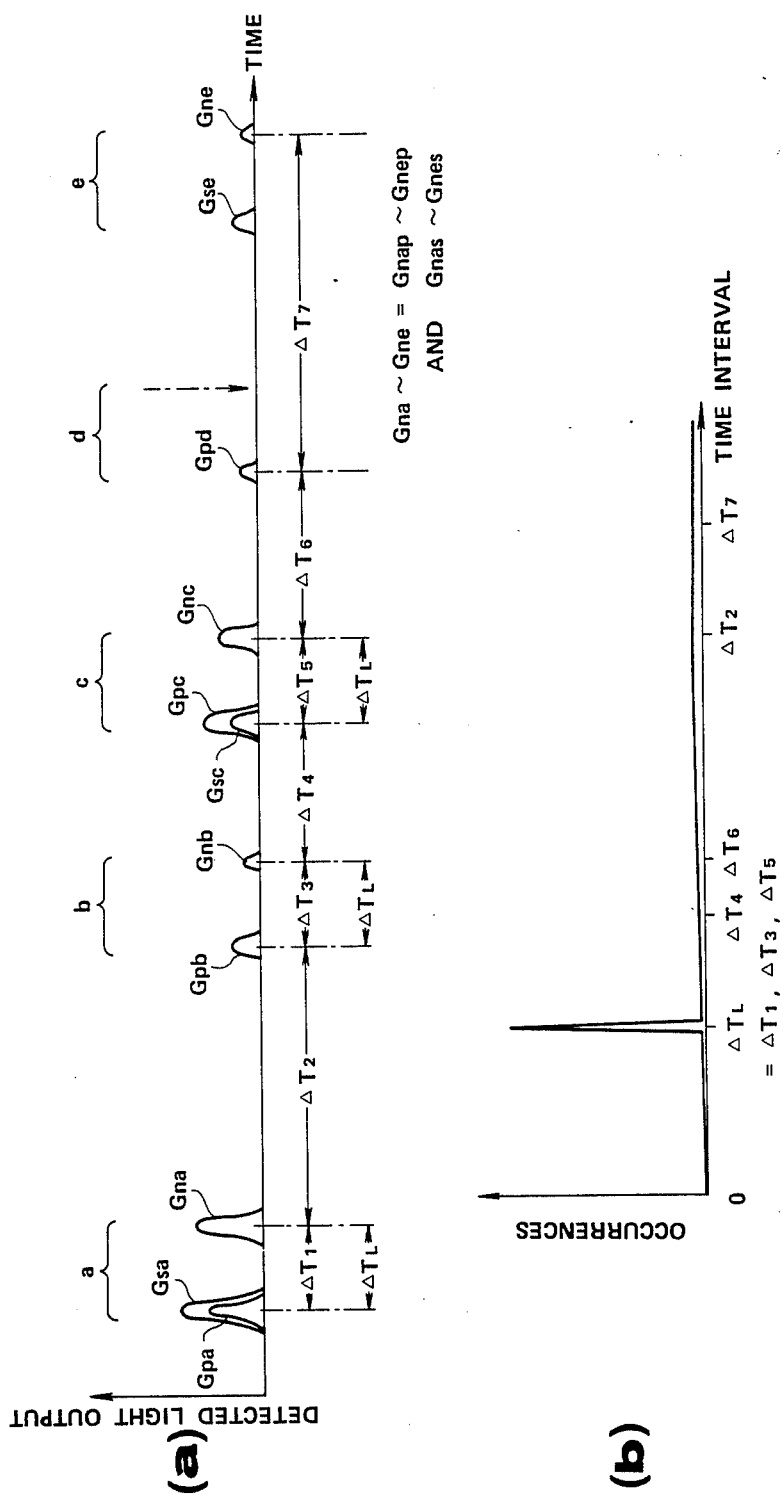
FIG. 29 is explanatory views of extraction of pairs of detected light outputs in the method according to the fifth aspect.
Figure 30:
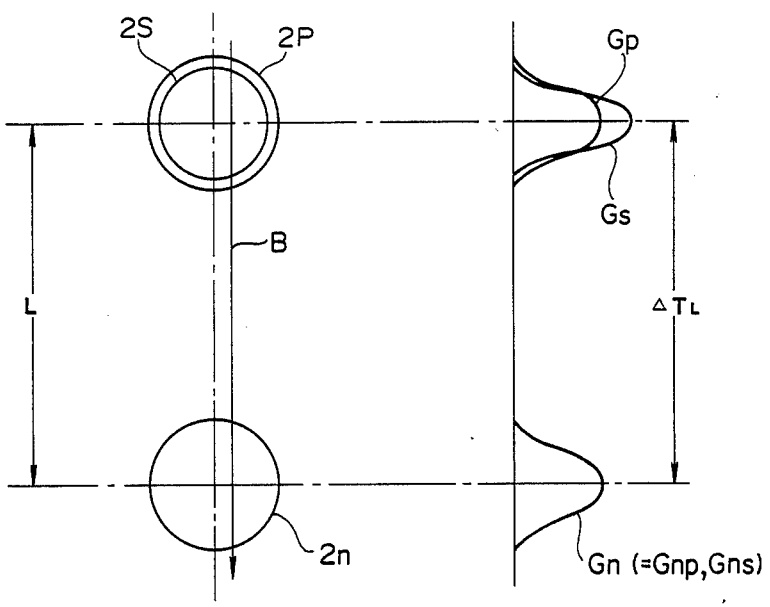
FIG. 30 is an explanatory view of the arrangement of beam spots and detected light outputs of a different case of the method according to the fifth aspect, where three laser beams are used.

The arrangement of the laser beams is not limited to that of FIG. 28 but may be as shown in, e.g., FIG. 30. That is, two laser beams having different intensity distributions from each other are used, and they are so arranged that their beam spots substantially overlap each other. The function of such arrangement is described above, and its explanation is omitted.

SIXTH ASPECT OF THE INVENTION

Figure 31:
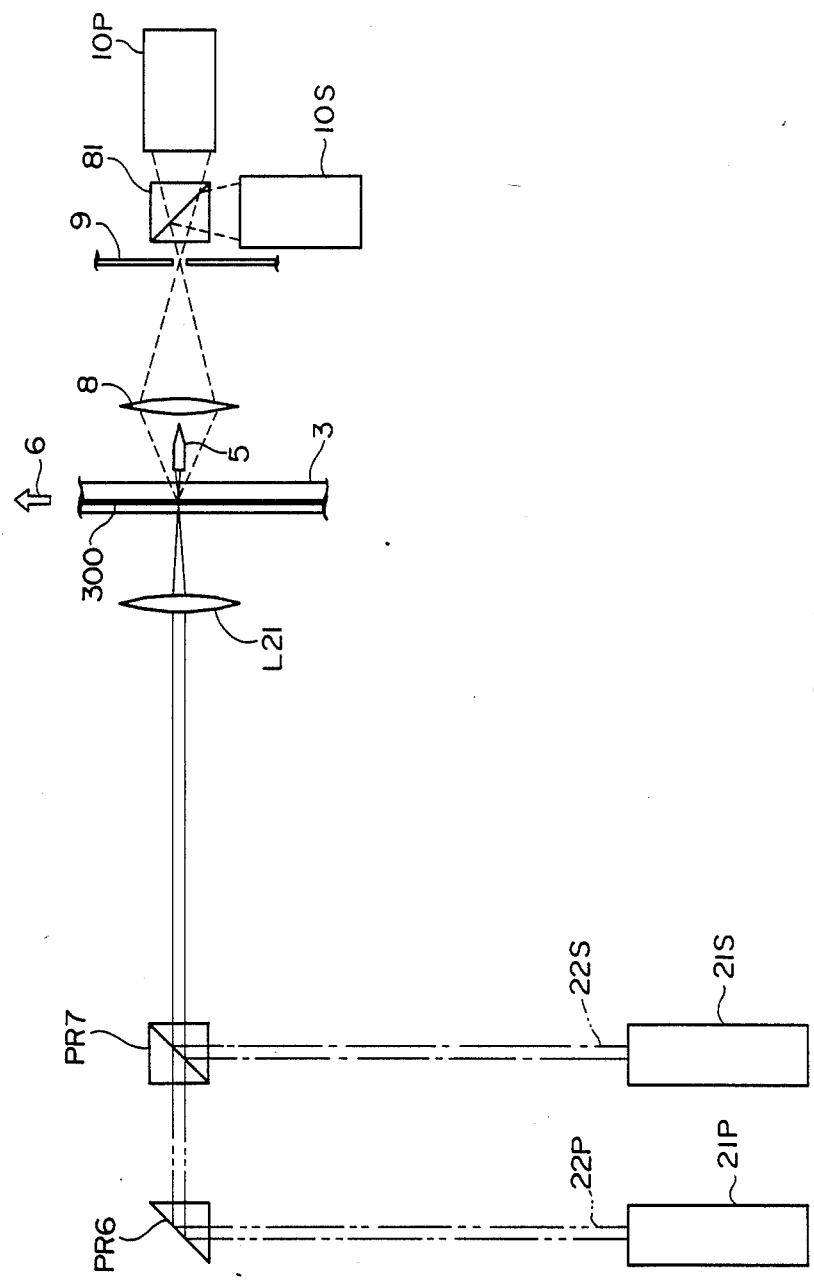
FIG. 31 is a block diagram of the fine particle measuring system according to the fifth aspect of this invention.

Next a fine particle measuring system according to a sixth aspect of this invention will be explained. FIG. 31 is a diagrammatic view of the system according to the sixth aspect of this invention. Two laser beams $22p,22s$ each emitted from two He-Ne laser sources $21p,21s$ are so adjusted by a lens L21 that they form a given beam spot in scattering regions. The linear polarized beam $22p$ is incident on a total reflecting prism PR6 to have its optical path changed and is incident on a linear polarized beam splitter PR7. On the other hand the linear polarized beam $22s$ is directly incident on the linear polarized beam splitter PR7. The planes of the respective linear polarized beams are so adjusted that the linear polarized beam $22p$ passes through the linear polarized beam splitter PR7 but the linear polarized beam $22s$ reflects on the linear polarized beam splitter PR7. This adjustment causes the linear polarized beams $22p,22s$ to overlap each other the beam spot and causes the lens L21 to form the beam spot in a flow passage 300 in a flow passage member 3. The linear polarized beams $22p,22s$ a little deviate in the vertical direction as viewed in FIG. 31 and have the positional relationships shown in FIGS. 22 and 23. In order to increase the intensity distribution of the linear polarized beams $2p,2s$ in the light scattering regions $4p,4s$ gradually inward from the peripheral portions thereof, the laser beam sources $21p,21s$ are Gaussian beam having their intensity distributions polarized in the s direction.

Of the scattered lights dispersed mainly in the forward direction and its vicinity, the component in the light receiving direction is formed into an image in a diaphragm 9 through a light receiving lens 8. The real image in the aperture of the diaphragm 9 is divided into the respective polarized components by a polarized beam splitter 81 which is so arranged that its light receiving plane is orthogonal to a light receiving direction 7. Then the divided components reach light detectors $10p,10s$ for detecting the respective components, where the components are converted into electric signals. The electric signals are supplied to a measuring unit, where their noise components are removed by a given process to be used as detected light outputs in measuring fine particles.

Next the structure and operation of the measuring system according to the sixth aspect will be explained with reference to FIGS. 32 and 33.

The outputs of the two light detectors $10p,10s$ shown also in FIG. 31 are supplied respectively to output measuring means $131p,131s$ and comparators $132p,132s$. The comparators $132p,132s$ have been respectively supplied with a threshold signal $V_{th}$. The comparators $132p,132s$ output respective ON signals when the output values of the light detectors $10p,10s$ are higher than the threshold value $V_{th}$ ($G \geq V_{th}$) and output respective OFF signals when the output values of the light detectors $10p,10s$ are smaller than the threshold value ($G < V_{th}$). The ON signal and the OFF singal are supplied to a coincidence judging means 135 and to the output measuring means $131p,131s$ referred to above. The output measuring means $131p,131s$ measure the outputs from the light detectors $10p,10s$ respectively only when the output measuring means $131p,131s$ are supplied with an ON singal. That is, the output measuring means $131p,131s$ measure those of the outputs (detected light outputs) of the light detectors $10p,10s$ which have their noise components removed by the threshold signal $V_{th}$ from a threshold setting means 133. In the case the output detecting means $131p,131s$ are provided by peak value detector, the peak value detectors supply maximum values of the respective detected light outputs (G) to switches $136p,136s$ respectively. In the case the output measuring means $131p,131s$ are provided by integrators, the integrators supply the integrated values with respect to time of the respective detected light outputs (G) to the switches $136p,136s$.

The coincidence judging means 135 is based on AND logic and gives out an opening signal only when both of the comparators 131p,131s output ON signals thereby to bring switches 136p,136s from their closed states into their open states. A computer 134 computes the values of the outputs (measured outputs) from the output measuring means 131p,131s.

Next, the function and operation of the above described fine particle measuring system according to the sixth aspect of this invention will be explained.

A sample fluid is caused to flow in the flow direction 6 in FIG. 31 by sample fluid feeding means not shown. When the laser beam sources 21p,21s are energized, the linear polarized beams 22p,22s are emitted and are formed into two linear polarized beams 2p,2s by the shown optical system. The two linear polarized beams 2p,2s are radiated to the fine particles in the sample fluid. At this time, of the scattered light dispersed mainly in the forward direction and its vicinity, the component in the light receiving direction is incident on the polarized beam splitter 81 through the light receiving lens 8 and the diaphragm 9. The scattered light incident on the polarized beam splitter 81 are divided into the p and the s components here, and the p and s components are received respectively by the light detectors 10p,10s and converted into respective electric signals (detected outputs). The detected outputs are processed by the circuit of FIG. 32.

Figure 32:
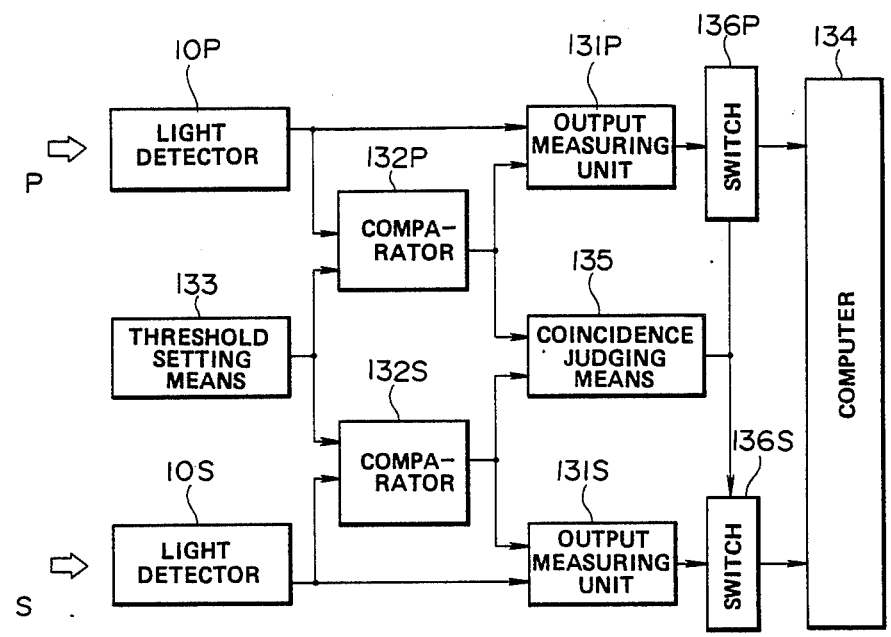
FIG. 32 is a block diagram of the measuring unit of the method according to the fifth aspect.
Figure 33:
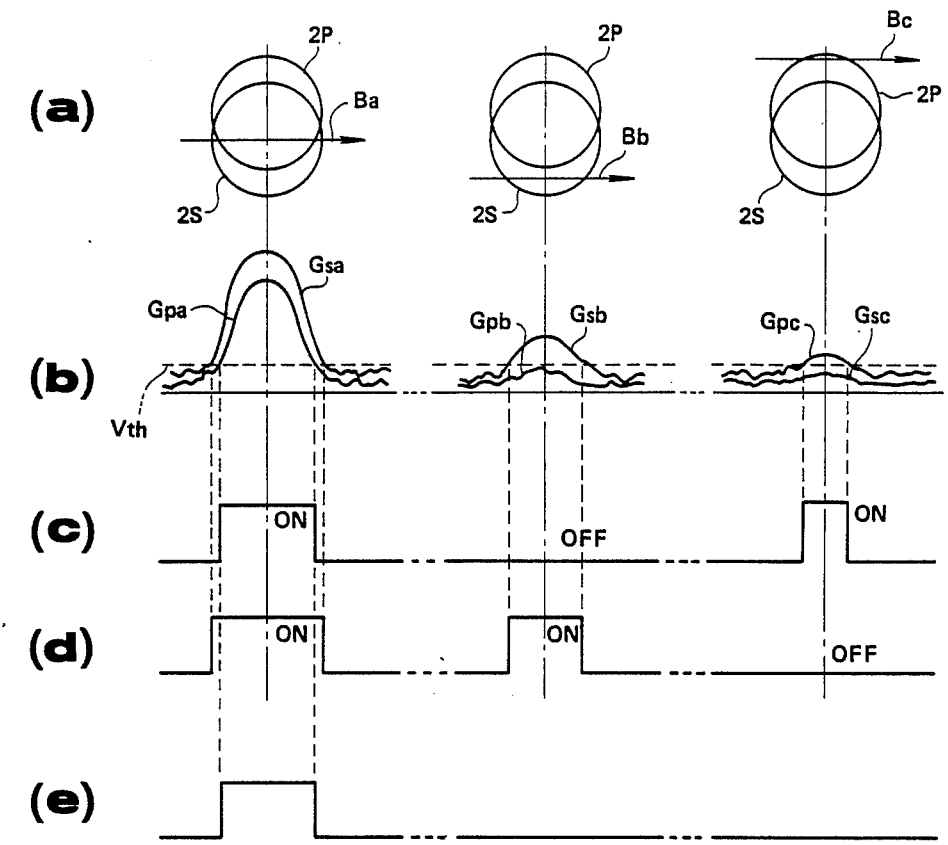
FIG. 33 is explanatory views of the operation of the measuring unit of FIG. 32.

The circuit of FIG. 32 carries out the signal processing of FIG. 33. The linear polarized beams 2p,2s are arranged as shown in FIG. 3(a). Three fine particles (a), (b) and (c) have flow passages (respectively indicated by the arrows $B_a$, $B_b$, $B_c$ in FIG. 33(a)). The light detectors 10p,10s detect the outputs shown in FIG. 33(b). When the fine particles (a)-(c) pass the linear polarized beam 2p, scattered light outputs $G_{pa}-G_{pc}$ are obtained, and when the fine particles (a)-(c) pass the linear polarized beam 2s, the scattered light outputs $G_{sa}-G_{sc}$ are obtained.

Here, when the threshold value of the threshold value setting means 133 is represented by $V_{th}$, $V_{th} > G_{pb}$, $G_{sc}$. Then the ON signal from the comparator 132p is as shown in FIG. 33(c). The ON signal from the comparator 132s is as shown in FIG. 33(d), and thus the opening signal from the coincidence judging means 135 is outputed for only the fine particle (c) as shown in FIG. 33(e). Accordingly measured outputs for the fine particle (a) which has passed both the p and s polarized beams 2p,2s are supplied to the computer 134. As described above, the computer 134 has a program of the process of the particle diameter measurement, and particle diameters of fine particles are given by the computer 134.

Figure 34:
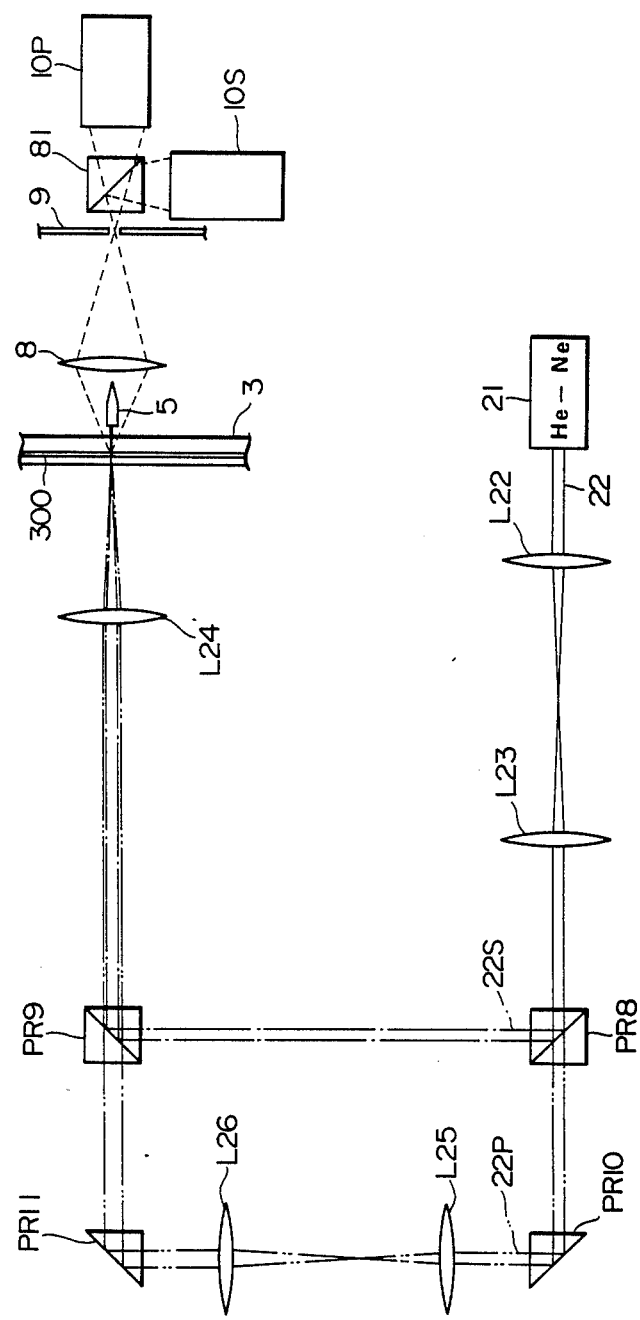
FIG. 34 is a block diagram of another optical system for forming two linear polarized beams of a first modification of the system according to the sixth aspect.

Next, a first modification of the above described embodiment of the system according to the sixth aspect of this invention will be explained with reference to FIG. 34.

The differences of the first modification from the above described embodiment of FIG. 31 are that a single laser beam source is used, and the beam spots of the two linear polarized beams have different intensity distributions from each other. A laser beam 22 emitted from a laser beam source 21 is passed lens L22,L23 to have a given beam size and is divided by a first polarized beam splitter PR8 into a linear polarized beam 22p and a linear polarized beam 22s. The linear polarized beam 22s is totally reflected by a second polarized beam splitter PR9 to be converged by a lens L24 on a flow passage 300.

On the other hand, the linear polarized beam 22p, which has passed the first polarized beam splitter PR8, is totally reflected by a total reflecting prism PR10 and then is incident on a total reflecting prism 11 through lenses L25 and L26. The lenses L25 and L26 are provided for the purpose of adjusting the beam spots so that the linear polarized beam 22p has a large beam spot than the linear polarized beam 22s. The linear polarized beam 22p totally reflected by the total reflecting prims PR11 passes the second polarized beam splitter PR9 and is converged to the flow passage 300 by the lens L24. In this first modification, the positional relationship between the beam spots is as shown in FIG. 24(a). Particle diameters of fine particles are measured by the same process of the method according to the fourth aspect of this invention.

Next, a second modification of the embodiment of the system according to the sixth aspect of this invention will be explained with reference to FIG. 35.

In the second modification, two laser beam sources are provided. One 21ps of the laser beam sources is a linear polarized laser beam source for emitting a linear polarized beam 22p and a linear polarized laser beam 22s. The other 21n of the two laser beam sources is a random polarized laser beam source for a third parallel beam (random polarized beam) 22n. Lenses L31 and L32 are provided for making the beam spot diameter of the linear polarized beam 22p in a light scattering region different from that of the linear polarized beam 22s. Lenses L33 and L34 are provided for causing the position of the beam spot of the parallel beam 22n in the direction of the laser beams. A prism PR14 is for adjusting the optical paths of the linear polarized beams 22p,22s, and the parallel beam 22n, and the beams having their optical paths adjusted by the prism PR14 pass through lenses L35-L37 to reach the flow passage 300 in linear polarized beams 2p,2s, and a parallel beam 2n. The lenses L35-L37 are for so adjusting the beams that they are spaced from one another parallel to one another and sufficiently converged in the flow passage 300.

Figure 12:
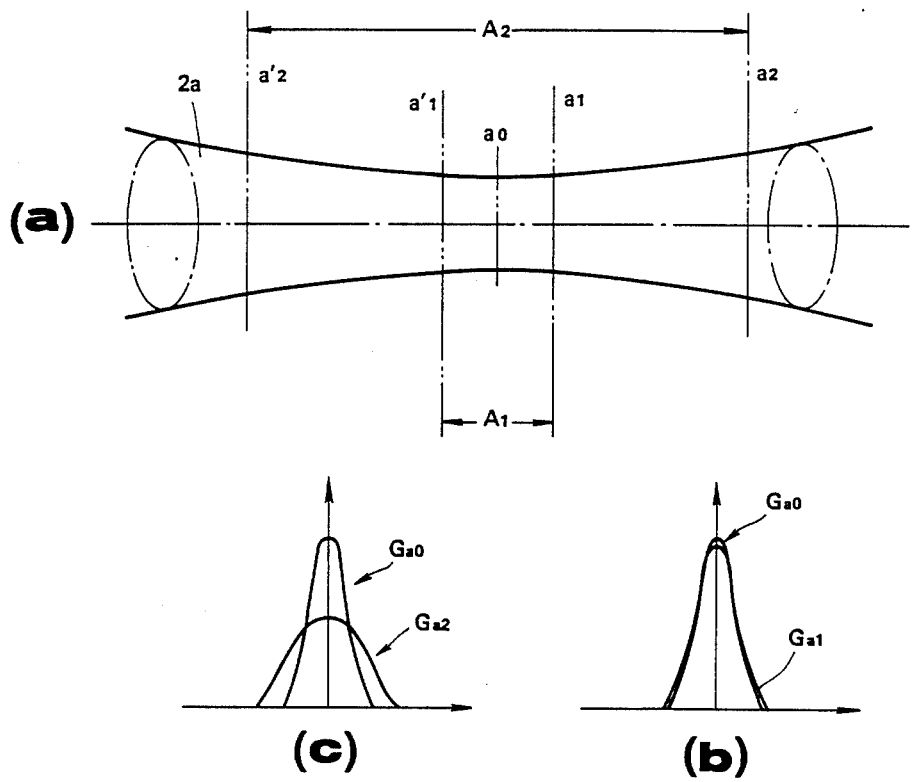
FIG. 12 is an explanatory view of restriction of the scattered light receiving region in the method according to the first aspect.

Scattered lights are received through a light receiving lens 8 by a polarized beam splitter 81 which is so arranged that its light receiving plane is orthogonal to the light receiving direction 7. In the polarized beam splitter 81, the scattered lights are deviced into the p polarized component and the s polarized component to be detected by light detectors 10p,10s. The difference of this second modification of FIG. 34 is that the diaphragm 9 which is provided before the polarized beam splitter 81 in the first modification of FIG. 33, is not provided. Because of this, in the second modification, the effective length of the light scattering region in the direction of the beams is long as shown in FIG. 12. Accordingly the detected outputs of the linear polarized laser beams 2p,2s contain the information in the direction of the laser beams. Consequently, it is impossible to measure fine particle diameters based on only the detected outputs obtained by the scattered lights dispersed by fine particles passing the linear polarized beams 2p,2s. For this reason, scattered light of the parallel process is explained in the method according to the fourth aspect of this invention, and its detailed description is omitted. The third parallel beam is not essentially a random polarized beam, and it may be a linear polarized beam or a beam having other polarization characteristics.

SEVENTH ASPECT OF THE INVENTION

Next a fine particle measuring system according to a seventh aspect of this invention will be explained.

Figure 35:
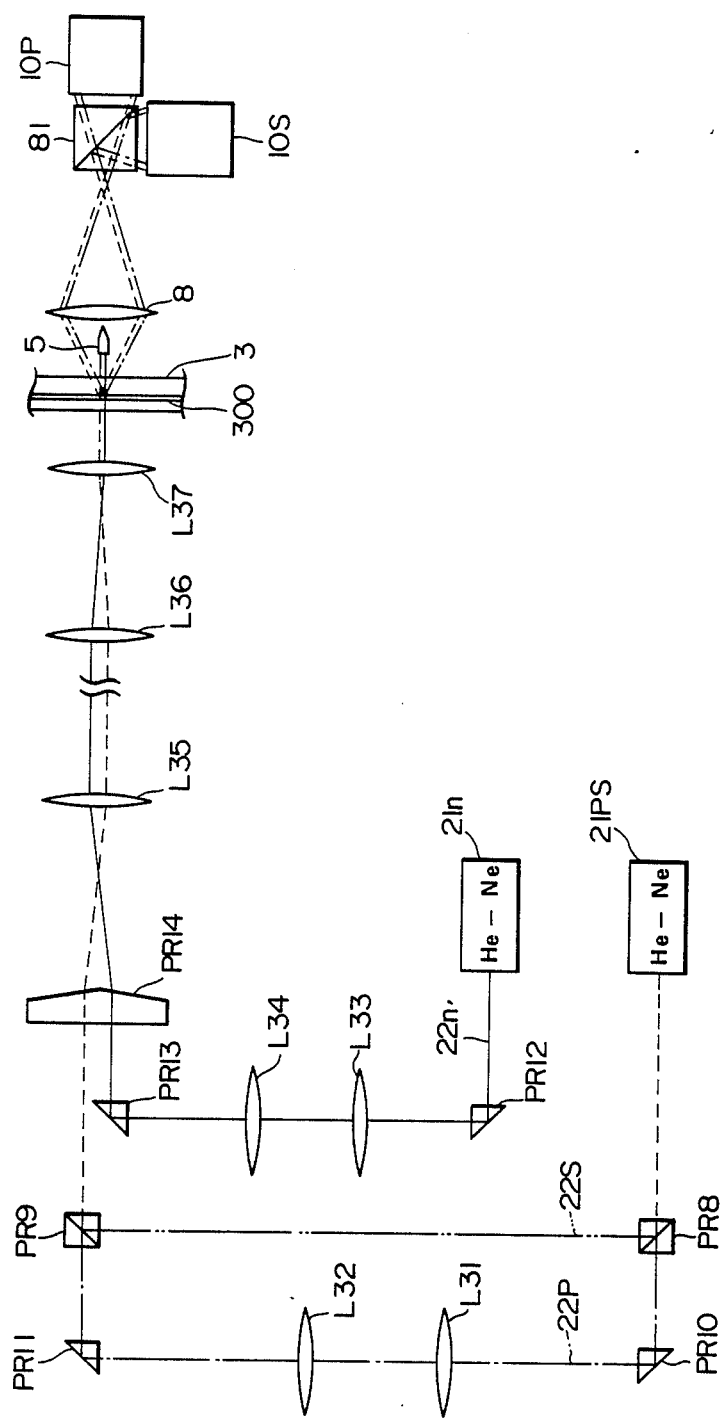
FIG. 35 is an explanatory view of an optical system for forming three laser beams of a second modification of he system according to the fifth aspect.

The same optical system as that of FIG. 35 is used. But the third parallel laser beam $2n$ does not essentially have the position of its laser beam spot deviating in the direction of the laser beams. Accordingly the lenses L33 and L34 may be omitted. This is because in the system according to the seventh aspect the third parallel laser beam is not used in measuring a sample fluid directly based on passage times of fine particles. The circuit for processing detected light outputs is the same as that of FIG. 32 except for that in the system according to this seventh aspect the outputs from the comparators $132p, 132s$ are inputted to the computer. In the fine particle measuring unit of the system according to this seventh aspect, a computer 134 computes the continuing time $\Delta t_{ON}$ of an ON signal for a detected output, and the continuing time $\Delta t_{OFF}$ of an OFF signal for an immediately preceding OFF signal are measured according to the p and the s polarized components and output values (G) according to the p and the s components, and stores three data in a set in the sequential order of their detections.

When the time of the generation of a maximum value of the output value (G) is the midpoint of the continuing time of the ON singal, the time interval $\Delta t$ between the generation of an immediately preceding maximum detected output and that of the current maximum detected output is given by $$\Delta t = \Delta t_{OFF} + (\Delta t_{ON} + \Delta t'_{ON})/2,$$

where $\Delta T'_{ON}$ is the continuing time of an immediately preceding ON signal. The measurement starting and finishing times are processed based on the detected output $G = \Delta t_{ON} = 0$.

The data of respective detected outputs are substituted with (G), and then computing process is carried out subsequently on them to give various particle diameter distributions. The computing process is the same as described above, and its explanation is omitted.

The methods and the systems according to the first to the seventh aspects of this invention described above enable accurate measurement of particle diameters of fine particles, but their effective usage of a sample fluid containing fine particles is low. The method and flow cells according to an eighth to the eleventh aspects of this invention are characterized by improved effective usage of a sample fluid.

EIGHTH ASPECT OF THE INVENTION

A fine particle measuring method according to an eighth aspect of the invention will be explained in good detail.

A laser beam 2 emitted from a laser beam source 1, e.g., a He Ne laser beam source, is reflected by a thirty six plane polygonal mirror 71 and is converged to the aperture of an incidence diaphragm through a lens L41 a scanning width diaphragm 9 and a lens L42. Then the laser beam 2 is formed into parallel scanning beams and are incident in a given spot size on a given light scattering region of a flow passage 300 of a flow passage member (not shown). The laser beam 2 which has passed the flow passage 300 is captured by a beam trap 5. The scattered lights of the laser beam dispersed by the fine particles in the flow passage 300 are received by a light receiving lens 8 and supplied to a light detector 10 through the diaphragm 9.

Figure 36:
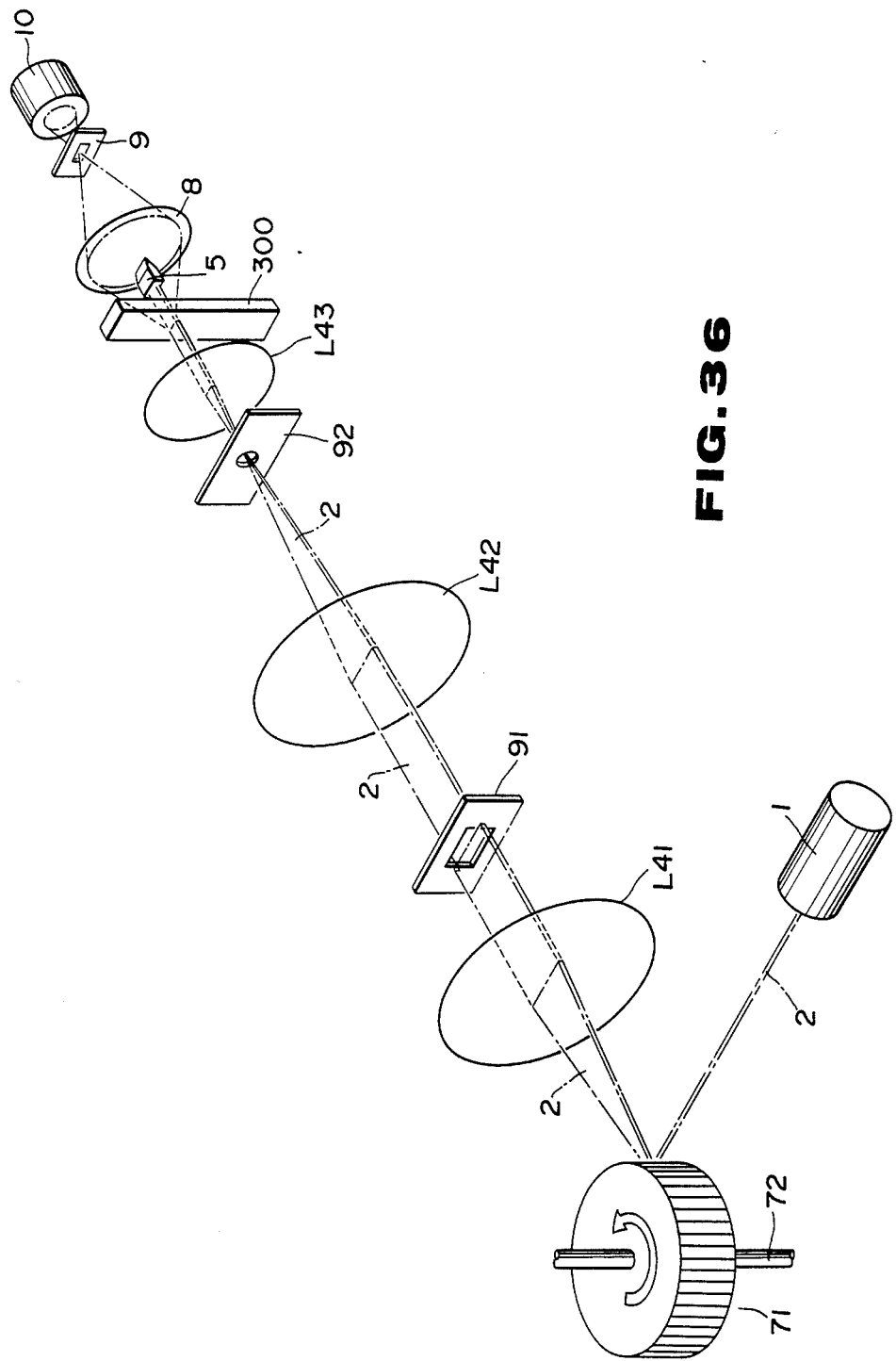
FIG. 36 is a perspective view of a main part of the optical system adaptable to the methods according to the eighth and the eleventh aspects.

The polygonal mirror 71 has a thirty six plane mirror (reflecting mirror) the planes of which are arranged equidistantly to have section perpendicular to the rotary shaft 27 in a regular thirty six angled shape, and the mirror 71 is rotatable on the shaft 72 in the direction indicated by the arrow in FIG. 36, The laser beam 2 is caused to scan by the polygonal mirror 71 in the horizontal direction (in the direction orthogonal to the rotary shaft 72 of the polygonal mirror 71). The scanning width diaphragm 91 has a slit having a little short distance in the scanning direction than the scanning width of the laser beam 2. The slit restricts the range of the laser beam 2 in the scanning direction (scanning width) is limited. The parts of the laser beam 2 on both ends of the scanning range correspond to the parts of the beam reflected against the boundary portions of the thirty six plane mirror of the polygonal mirror 71. This forms the laser beam 2 which does not have a prescribed intensity distribution into a laser beam 2 having a required scanning width, which is caused to scan at a constant scanning speed and in a given direction. The incidence diaphragm 92 is for preventing the so called stray lights thereby to improve the measuring sensitivity. A sample fluid containing fine particles flows through the flow passage 300 defined in the flow passage member. The fine particles pass the laser beam 2 and form scattered lights in every direction. A diaphragm 9 is for restricting the area of the light scattering region.

The method according to the eighth aspect will be explained by means of the optical system used therein.

In a first step of the method, the laser beam 2 is caused to scan at a constant speed and in a given direction so that the laser beam 2 intersects orthogonally to both the flow direction of the sample fluid through the flow passage 300 of the flow passage member and the direction thereof. The scanning speed is set by the rotation speed of the polygonal mirror 71, and the scanning direction is set by the direction of rotation of the polygonal mirror 71. In a second step the radiating area of the laser beam 2 to fine particles is restricted by the scanning direction. The width in the sanning direction (scanning width) is set by the length of the above described scanning direction of the slit of the scanning width diaphragm 91.

The scanning of such laser beam 2 improves the effective usage of a sample fluid is much improved.

Figure 37:
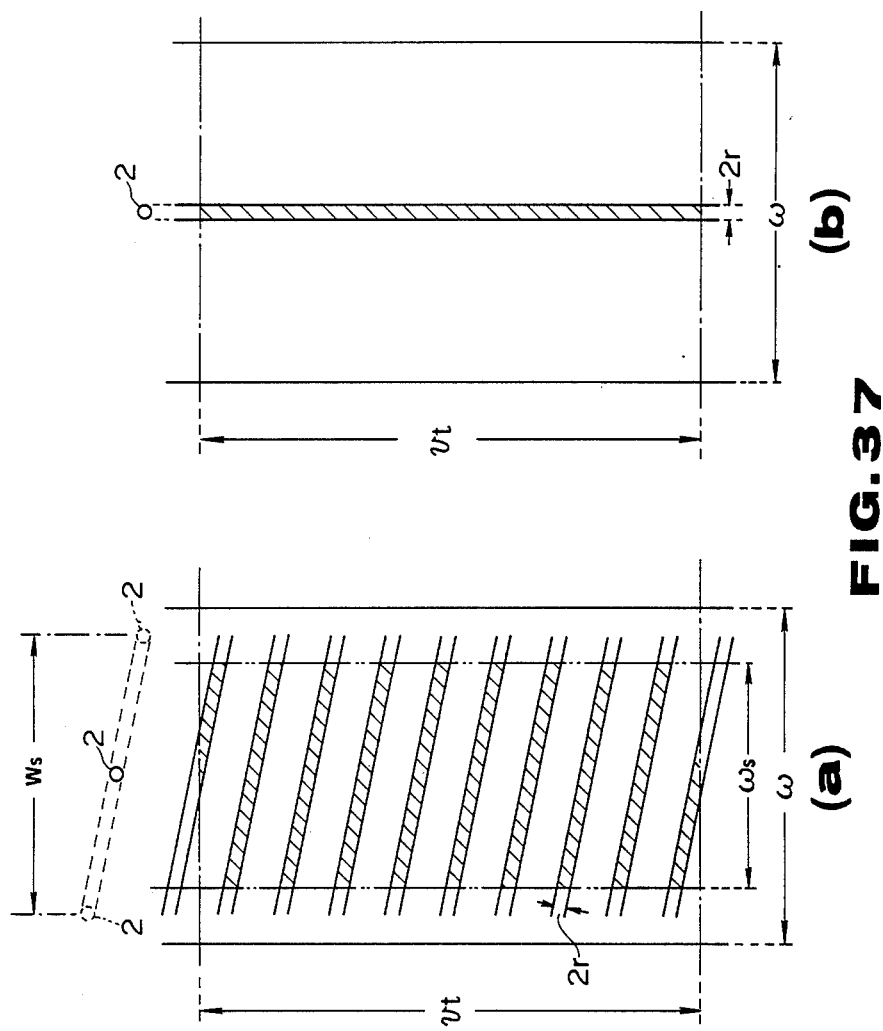
FIG. 37 is explanatory views of the effective usage of a sample fluid in the methods of FIG. 36.

This will be explained diagrammatically with reference to FIG. 37. The measurable minimum spot diameter of the laser beam 2 is represented by $2r$; the width of the flow passage of a sample fluid as viewed in the direction of the laser beam 2, $\omega$; the flow speed of the sample fluid, v; the measuring time, t; the scanning range of the laser beam 3, $W_S$; the restricted scanning width, $\omega_S$; and the times of the scanning in the time, n. Then, according to the eighth aspect, the range of the effective use of a sample fluid is the shaded parts in FIG. 37(a). According to the conventional method in which the laser beam is not caused to scan, however, the area of the effective use of a sample fluid is the shaded part in FIG. 37(b). Specifically in the conventional method, the above described effective usage $\mu$ is $$\mu = 2r \cdot vt / \omega \cdot vt = 2r/\omega.$$

In the expression, when $r = 10\ \mu m$, and $\omega = 0.8\ mm$, $\mu = 2r/\omega = 2 \times 1.0 \times 10^{-2}/0.8 = 2.5 \times 10^{-2}$.

In contrast, specifically according to the eighth aspect of this invention, the effective usage $\mu$ is $\mu = [2r \cdot n \cdot \{W_s^2 + (vt/n)^2\}^{1/2} \omega_s]/(\omega \cdot vt \cdot W_s)$, when $r = 10 \mu m$, $\omega = 0.8$ mm, $W_s = 0.7$ mm, $\omega_s = 0.6$ mm, $n = 10$ times; and $vt = 1.5 \mu = 1.7 \times 10^{-1}$. It is seen that the effective usage of a sample fluid is much improved. The above described calculation is diagrammatically shown, but in practical designing, other various conditions, e.g., an effective area of the light scattering region, have to be considered.

In a third step, the scattered lights formed by fine particles passing the scanning laser beam are detected by the light detector 10. In this case the scattered lights dispersed forward of the direction of the laser beam 2 are detected. But the scattered lights to be detected are not limited to them. The detected scattered lights are converted into electric signals, which are subjected to a required signal processing. That is, those of the electric signals which exceed a given threshold level are used as detected outputs (G), and based on the values of the accepted detected outputs, particle diameters of fine particles are measured. The function (F) for deriving a particle diameter from the output value (G) is empirically given beforehand, and the particle diameter $D_p$ is expressed by $D_p = F(G)$.

At the same time, by counting the occurrences of the detected outputs (G) by a counter circuit or software now shown, numbers of fine particles are given.

Next, in a fifth step, particle diameter distributions of fine particles are given. To this end a separate flow meter is provided in the flow passage member defining the flow passage 300, or a constant volume of a sample fluid is caused to flow by a sample fluid feeding device. A volume of a sample fluid is determined by an indicated value of the flow meter, and in the latter a volume of a sample fluid is determined by a preset value. Based on a volume of a sample fluid thus determined, and a measuring result of particle diameters described above and a counted result of numbers of fine particles, particle diameter distributions of fine particles, e.g., a density of numbers of fine particles according to particle diameters.

Japanese Patent Laid Open Publication No. 262633/1986, for example, describes the art for measuring basically stationary floating fine particles by scanning laser beam. But this art is only for measuring fine particles floating in, e.g., indoor space, with low measuring precision. The art of the Publication is completely different from the method according to the eighth aspect of this invention which is for measuring fine particles in a sample medium (sample fluid) with high precision.

NINTH ASPECT OF THE INVENTION

A method for measuring fine particles according to a ninth aspect of this invention will be explained.

Figure 38:
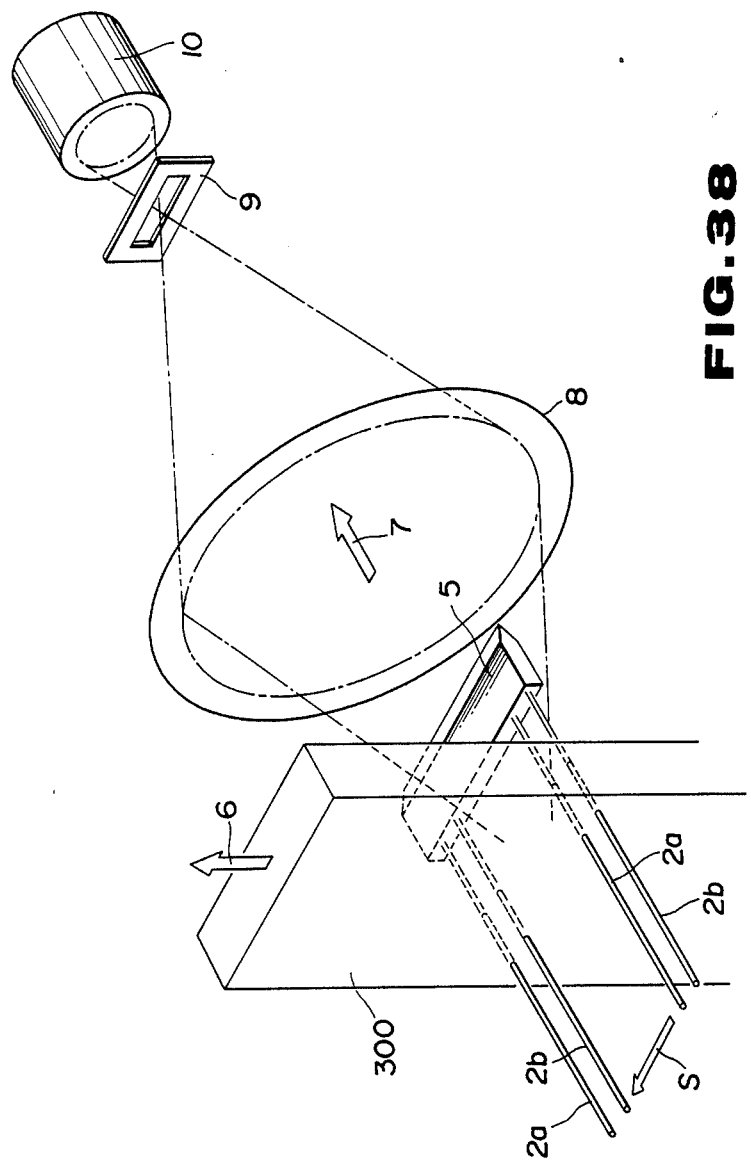
FIG. 38 is a perspective view of the optical system adaptable to the methods according to the ninth, tenth and twelfth aspects.

As shown in FIG. 38, the laser beam used in this method comprises two parallel laser beams $2a, 2b$ to each other. The two parallel beams $2a, 2b$ are spaced from each other by a given distance so that they have no physical optical interference therebetween (but they are not polarized beams having their polarization places orthogonal to each other). The two beams $2a, 2b$ have a substantially the same intensity distribution (preferably completely the same). The spot diameters of the two laser beams $2a, 2b$ are substantially the same (preferably completely the same).

The two laser beams $2a, 2b$ are caused to scan at a constant speed in one direction (indicated by the arrow (S) in FIG. 38) to intersect the flow direction of a sample fluid orthogonally to the direction thereof. A beam trap 5 for capturing the two laser beams $2a, 2b$ are formed to be elongated in the scanning direction.

At the position where the beam spots of the two laser beams $2a, 2b$ become minimum, a flow passage 300 defined by a flow passage member of rectangular section (not shown) is arranged orthogonal to the laser beams $2a, 2b$. A sample fluid flows through the flow passage 300 in the flow direction indicated by the arrow 6. The sample fluid contains fine particles to be detected. Since the laser beams $2a, 2b$ are caused to scan in the direction indicated by the arrow (S), the relative flow direction and the relative flow speed of the sample fluid as viewed in the direction of the laser beams $2a, 2b$ is given as the vector sum of the vector given by the scanning direction and speed of the laser beams $2a, 2b$, and the vector given by the flow direction and flow speed of the sample fluid.

Since this method according to the ninth aspect is based on that the low speed of the sample fluid is known as will be described below, there is provided a flow meter or a quantitative sample fluid feed pump, for example, in the flow passage member.

The fine particles radiated with the laser beams $2a, 2b$ disperse scattered lights in every direction in accordance with the Mie's light scattering theory referred to above. A part of those of the thus scattered lights dispersed forward (in a light receiving direction 7) are formed at the image point of a diaphragm 9 into a real image in the light scattering region through a light receiving lens 8.

The scattered lights are detected as scattered light outputs by a light detector 10 (e.g., a photomultiplier) to be converted into electric signals therein. The noise components of the electric signals are removed by a given threshold level, and the electric signals are prepared as detected light outputs. The detected light outputs are subjected to a given processing by an A D converter and then supplied to a computer or others not shown for the computation of particle diameters.

Figure 39:
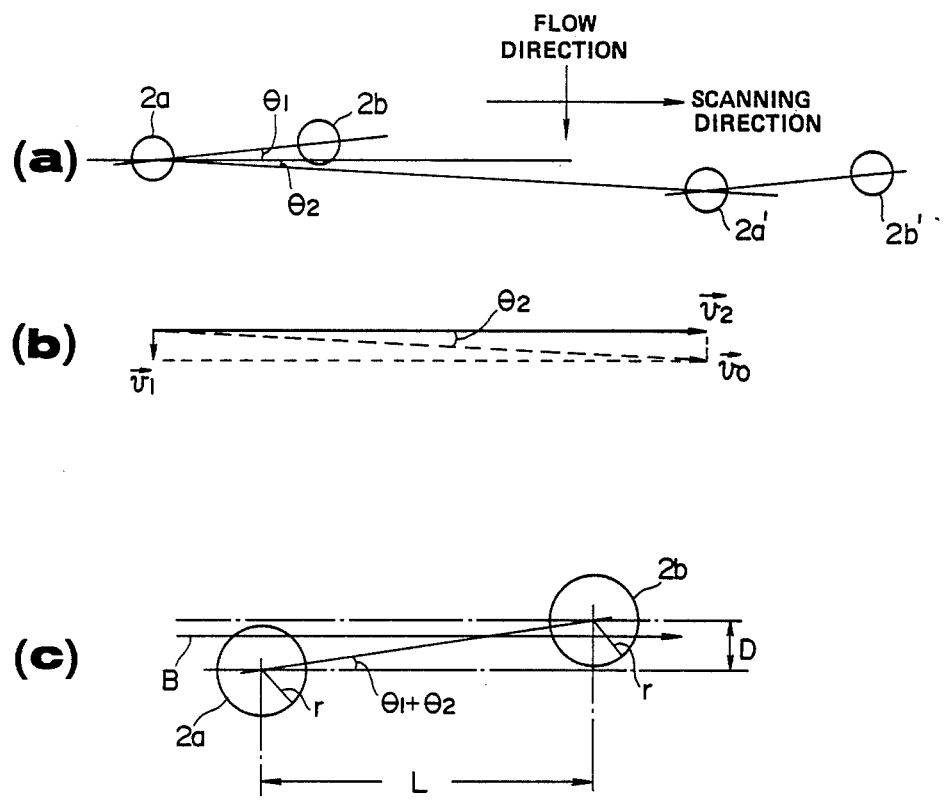
FIG. 39 is explanatory view of the relative flow and its direction in the methods of FIG. 38.

FIG. 39 are explanatory views of the relative flow speed and relative flow direction between the two parallel beams $2a, 2b$. As shown in FIG. 39(a), the parallel beams $2a, 2b$ deviate from each other by an angle $\theta_1$ in the scanning direction, and, as shown in FIG. 39(b), are caused to scan in the direction of a vector $v_2$ and speed of this vector $v_2$. At this time, if the flow direction and flow speed of the sample fluid is a vector $v_1$, the relative flow direction and flow speed of the fine particle in the sample fluid are as shown by vector $v_0$ in FIG. 39(b). Accordingly, as shown in FIG. 39(c), when the direction of the vector $v_0$ given by the sum of the vectors $v_1$ and $v_2$ is measured on the horizontal axis to show the beam spots of the parallel beams $2a, 2b$, the flow line (B) of the fine particles becomes parallel with the horizontal axis. Here, the projection distances (D) and (L) between the centers of the beam spots of the parallel beams $2a, 2b$ have the relationship $$\tan(\theta_1 + \theta_2) = D/L.$$

Thus, according to this method, the parallel beams $2a, 2b$ can deviate from each other orthogonally to the above described relative flow direction and the direction of the parallel beams $2a, 2b$ by a distance (D) in the range in which the beam spots of the parallel beam $2n$ are detected, and based on the detected outputs, fine particle diameters can be measured. This beams $2a, 2b$ overlap each other in the flow direction of the fine particles, and the beam spots of the parallel beams $2a, 2b$ spaced from each other by a distance $(D^2 + L^2)^{\frac{1}{2}}$ between the centers thereof which prevents physical optical interference between the parallel beams $2a, 2b$. Accordingly, the method according to the ninth aspect can much improve the measuring precision of particle diameters compared with that according to the eighth aspect.

Figure 40:
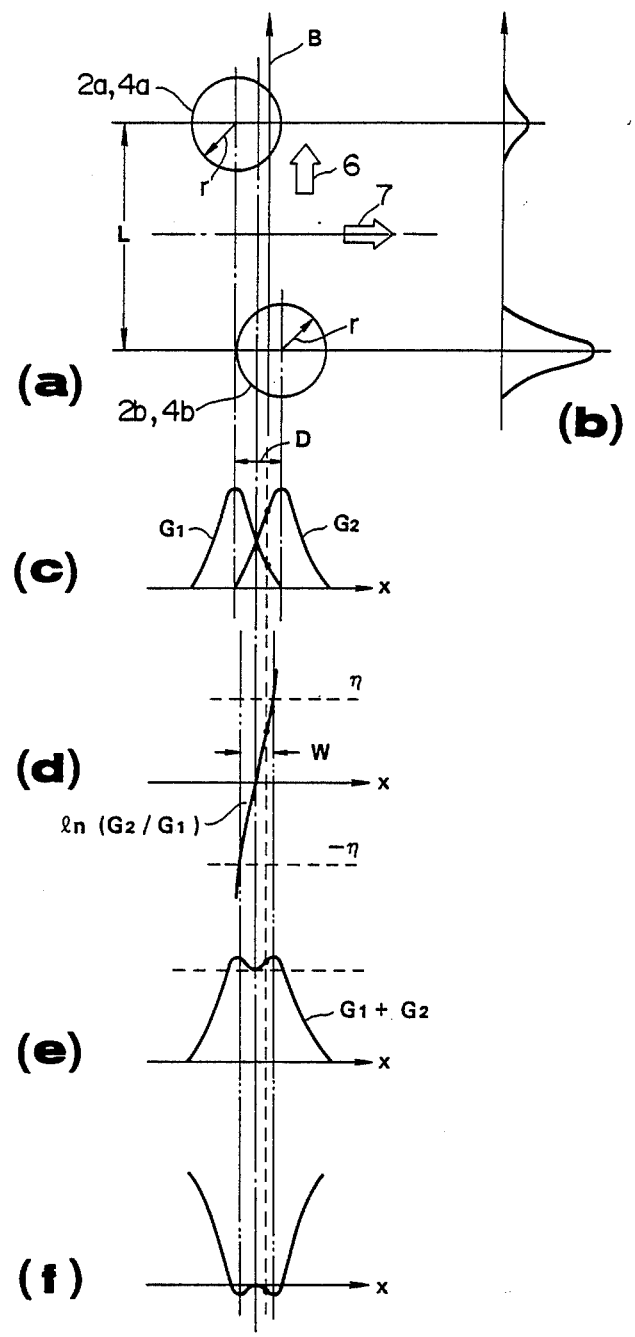
FIG. 40 is explanatory view of the operation of the methods of FIG. 38.

FIG. 40 is explanatory views of the improved measuring precision of the method according to the ninth aspect. FIGS. 40(a)-(f) correspond to FIGS. 7(a)-(f). The difference between FIGS. 7 and 40 is that in FIG. 40 the flow direction of a sample fluid is provided by the relative flow direction $6_{re}$ given by the vector sum as described above. In FIG. 40, the deviation amount between the beam spots is substantially the same as the radius of the beam spots but is not limited to the relative flow direction $6_{re}$. In FIG. 40(a), (D) and (L) represent the deviation amounts in the directions orthogonal to and parallel to the relative flow direction $6_{re}$ respectively. When the flow direction 6 in FIG. 7 is replaced with the relative flow direction $6_{re}$, FIG. 7 becomes identical with FIG. 40. The method according to the ninth aspect can remove errors of measuring particle diameters resulting from disuniform intensity distributions of the laser beam that is an disadvantage of the method according to the eighth aspect. Besides, the effective area of the light scattering regions $4a, 4b$ for the measurement can be made sufficiently larger compared with the method according to the eighth aspect.

Next, the process of the measuring particle diameters of the method according to the ninth aspect will be explained.

In this method according to the ninth aspect, a sample fluid may have a known flow speed or may be stationary (not flowing). Unless the passing speed (passage time) of fine particles is directly measured (by the laser beam), as is done in the method according to a tenth aspect which will be described below, the flow speed of a sample fluid has to be measured separately by a flow meter or others, or the sample fluid has to be caused to flow at a flow speed in a given range by a feed pump (not shown). With a known flow speed of the sample fluid, a prescribed scanning speed of the laser beams $2a, 2b$, and a given distance (L) between the centers of the beam spots of the laser beams $2a, 2b$, the value of a time interval between the passage times of a fine particle is estimated only by the relationship with the relative flow speed.

In a first step of the method according to the ninth aspect, the fine particles in a sample fluid are placed in the above described conditions. In a second step, the fine particles pass the scanning laser beams $2a, 2b$ and disperse scattered light in every direction, such as sidewise, forward, etc. of the laser beams $2a, 2b$. The scattered lights are detected as scattered light outputs by a light detector (not shown) and converted into electric signals to be supplied to a measuring unit (not shown). There the second step is followed by a third step.

When a fine particle passes only one of the laser beams $2a, 2b$, two detected outputs are not obtained successively at the known time interval (the time interval between the passage times $\Delta T_L$), which is given only the relative flow speed (U) of the sample fluid and the projection distance (L) in the relative flow direction $6_{re}$. Such detected outputs can be removed as not to be measured by the extracting circuit, in, e.g., a signal receiving section of the measuring unit. Besides, by making the output pulse width of a counter circuit included in the extracting circuit variable in accordance with the flow speed of a sample fluid and the scanning speed of the laser beams, the third step is applicable to the measurement of fine particles virtually flowing at various relative flow velocities.

In a fourth step, a pair of detected outputs extracted for the measurement by the third step are examined with respect to the output ratio $G_2/G_1$. The fourth step is the same as the third step of the method according to the first aspect.

Next, in a fifth step, a particle diameter $D_p$ is measured. The measurement is based on the output values $G_1, G_2$ of the pair extracted by the fourth step for the measurement. The fifth step is the same as the fourth step of the method according to the first aspect.

Figure 41:
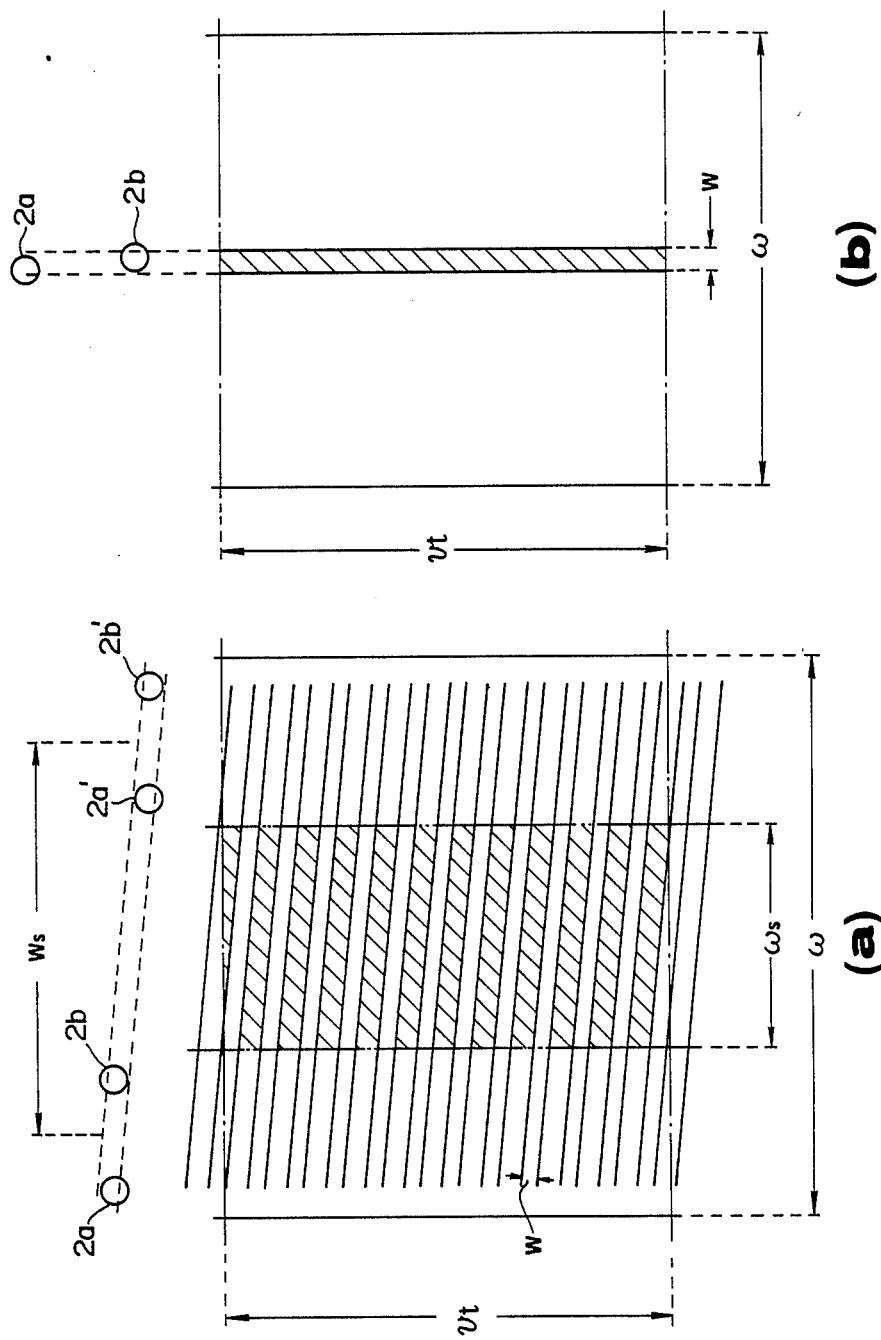
FIG. 41 is explanatory view of the effective usage of a sample fluid in the methods of FIG. 38.

As described above, different from the method according to the eight aspect, in the method according to the ninth aspect, two parallel beams are used, and the beam spots of the laser beams overlap each other at least partially in the relative flow direction, so that the effective width (W) of the light scattering regions can be increased. Besides, in this method according to the ninth aspect, a correction coefficient is determined by the detected outputs of the two laser beams, and based on the correction coefficient, the detected outputs are corrected, and consequently a more precise measuring result can be obtained compared with the method according to the eighth aspect. The important point of the method according to the ninth aspect is that the effective usage of a sample fluid can be much improved as in the method according to the eighth aspect. FIG. 41 is explanatory view of the improvement of the effective usage of a sample fluid. FIGS. 41(a) and (b) correspond to FIGS. 37(a) and (b) respectively. In FIGS. 41(a) and (b) the areas where a sample fluid is effectively is used are shaded.

The above description is based on that the flow speed of a sample fluid is known, but a sample fluid may be stationary. When a sample fluid is not on the move (in the case of a stationary sample fluid), the scanning takes place once, and the relative flow speed and direction are the same as the scanning speed and direction of the laser beams $2a, 2b$.

The laser beams $2a, 2b$ in FIG. 40 have Gaussian distributions and have substantially the same intensity distribution. But the fine particle measuring method according to the ninth aspect of this invention is not limited to such laser beams as described above.

The method according to the ninth aspect is based on that the flow speed of a sample fluid is known, and in the third step thereof, when a current detected light output and a detected light output following the current detected output at a given time interval (a known time interval) are obtained, both are taken as a pair of detected light outputs for one fine particle. As described in the method according to the first aspect, measuring errors can be more decreased by detecting a scattered light (scattered light output) at a given time interval after a given time has passed from the immediately preceding detection of a scattered light.

The method according to the ninth aspect is based on that the length of the light scattering regions 4a,4b are restricted so small by the diaphragm 9 that there is no large differences between the laser beams 2a,2b in the intensity distribution and spot diameter in the effective light scattering regions 4a,4b. In the case, however, that since cause of a large diaphragm 9 or the absence thereof, the effective light scattering regions 4a,4b are elongated, the intensity and spot diameter of the laser beams 2a,2b become unignorably different. In such case, as described in the third and the fourth modifications of the method according to the first aspect, the information of the positions in the direction of the laser beams are obtained in the way described with reference to FIGS. 13 and 14.

TENTH ASPECT OF THE INVENTION

Next, a fine particle measuring method according to a tenth aspect will be explained with respect to the differences from the method according to the ninth aspect.

The characteristic of the method according to the tenth aspect of this invention is that the flow speed of a sample fluid is directly measured by laser beam. In the method according to the ninth aspect, the flow speed of a sample fluid is measured by a separate flow meter, or is set at a constant flow speed by a suitable sample fluid feed means (not shown). In the method according to the tenth aspect, however, the flow speed and volume of a sample fluid may be unknown.

In a first step of this method according to the tenth aspect, two parallel beams are formed, and in a second step the two parallel beam are caused to scan. But the first and the second step are the same as those of the method according to the ninth aspect.

In a third step, scattered lights despersed by fine particles passing the two parallel beams are detected as scattered light outputs by a suitable light detector. The scattered lights are successive formed by one and the same fine particle passing the two parallel beams 2a,2b or are formed singly by one and the same particle passing only one of the two parallel beams. Since the method according to the tenth aspect is based on that the relative flow speed of a sample medium (sample fluid) is unknown, it is impossible to find which fine particle a scattered light belongs to. Accordingly the following fourth and the fifth steps are carried out.

In the fourth step, the time interval between, e.g., the maximum values of two successive detected outputs is given, and based on the given time interval, a pair of detected outputs of one and the same fine particle is extracted. That is, the time interval $\Delta T_L$ between the detected light outputs generated when one and the same fine particle pass successively the two parallel beams are expressed in a function of the relative flow speed (U) of a sample fluid and the distance (L) between the centers of the laser beams 2a,2b in the relative flow direction, $$\Delta T_L = L/U.$$

Then, even if the output values $G_1$, $G_2$ are taken together without being identified as the respective output values obtained by one and the same fine particle passing the two parallel beams, when the time interval $\Delta T$ between two successive output values (G), a peak of the occurrences of the time interval $\Delta T_L$ for one and the same fine particle appears. Accordingly by using computing means, e.g., a computer, the time interval $\Delta T_L$ can be easily identified, and a pair of output values for one and the same fine particle can be extracted.

In a sixth and a seventh steps, particle diameters of fine particles are given. The sixth and the seventh steps are the same as the fourth and the fifth steps of the method according to the ninth aspect, and their explanation is omitted.

As described above, in the method according to the tenth aspect, even the flow speed of a sample medium is unknown, the relative flow speed is measured based on a peak of the occurrences of a time interval between detected light outputs, and based on the peak, a pair of detected outputs for one and the same fine particle can be extracted, so that particle diameters of fine particles can be measured.

Next, a modification of the method according to the tenth aspect will be explained.

This modification includes the following eighth and ninth steps in addition to the first to the seventh steps described above. In the eighth step, the volume (V) of a sample fluid which has passed significantly through an effective area of a light scattering regions. Here, the light scattering area (S) is decided, as described in the method according to the ninth aspect, by the length (A) of the light scattering reigons 4a,4b determined by the diaphragm 9, and the effective width (W) of the light scattering regions 4a,4b and is expressed by $$S = A \cdot W.$$

On the other hand, the relative flow speed (U) is given by, as described above, $$U = L/\Delta T_L.$$

Then the virtual volume (V) of a sample medium at the time interval $\Delta T$ is given by $$\begin{aligned} V &= S \cdot U \cdot \Delta T \\ &= A \cdot W \cdot L \cdot \Delta T / \Delta T_L. \end{aligned}$$

Next, in the ninth step, a density of numbers of particles according to particle diameters as one of particle diameter distributions is given. This is computed based on the particle diameters given by the seventh step, and the volume of the sample medium given by the eighth step. For example. numbers of fine particles according to particle diameters are counted, and the numbers are divided by the volume (V) given above to determine particle diameter distributions in the form of densities of numbers of particles according to particle diameters.

ELEVENTH ASPECT OF THE INVENTION

The system according to a eleventh aspect corresponds to the method according to the eighth aspect and is characterized in that a single laser beam is caused to scan by scanning means, e.g., a polygonal mirror, in the direction to intersect the flow direction of a sample fluid. The system for this method has been explained with reference to FIG. 36, and its explanation is omitted.

TWELFTH ASPECT OF THE INVENTION

Figure 42:
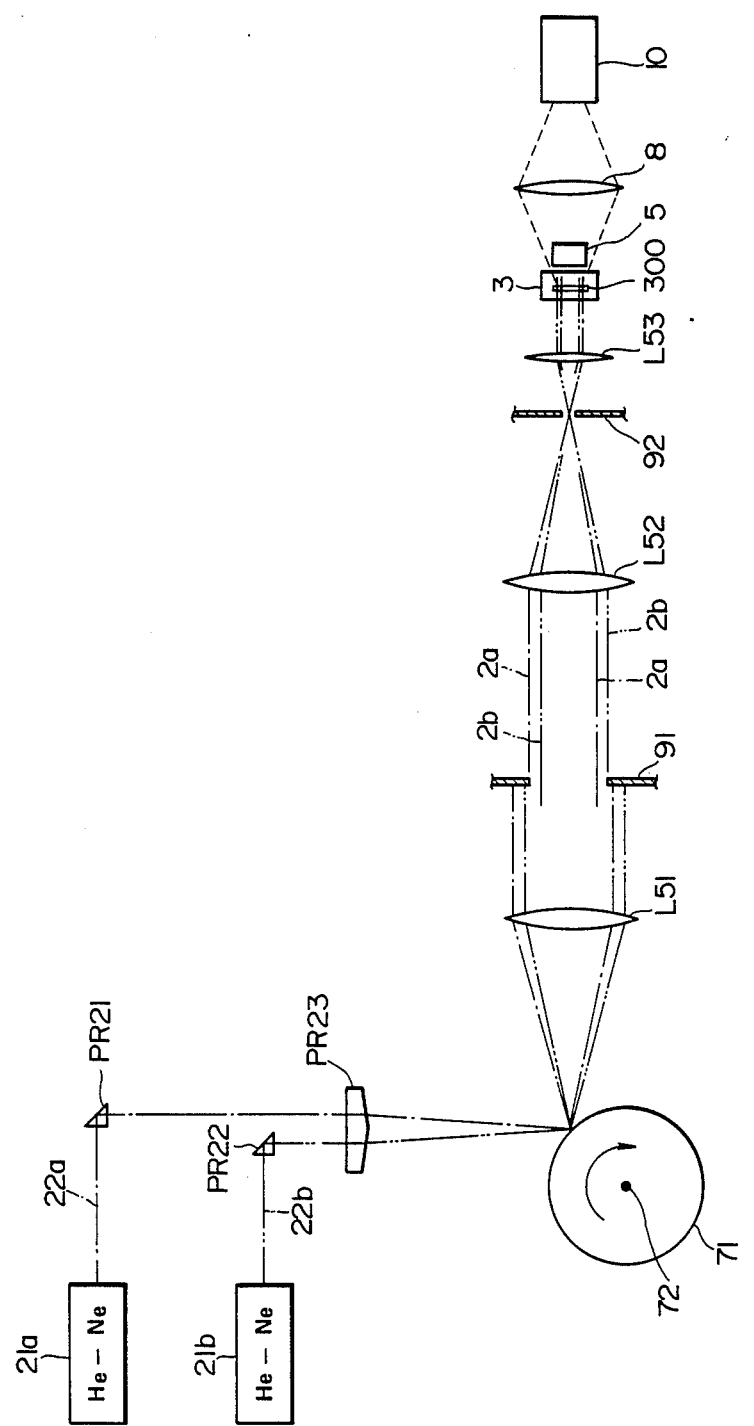
FIG. 42 is diagrammatic view of the optical system for the system according to the twelfth aspect.

A system according to a twelfth aspect corresponds to the methods according to the ninth and the tenth aspects and is characterized in that more than two laser beams are caused to scan by. e.g., a polygonal mirror. FIG. 42 shows a diagrammatic view of the system for one embodiment of the method according to the twelfth aspect. The difference of the system of FIG. 42 from that of FIG. 36 is that the laser beam source comprises two He-Ne laser beam sources 21a,21b, and the laser beams emitted from the sources are totally reflected against total reflecting prisms PR21,PR22, then have their optical paths adjusted by an optical path adjusting prism PR23, and then is incident on a thirty six sided polygonal mirror 71. A flow passage 300 and a beam trap 5 are formed to be elongated in the scanning direction. Scattered lights dispersed by fine particles passing the scanning laser beams (two parallel beams) 2a,2b reach a light detector 10, where the scattered lights are converted into electric signals. The electric signals are supplied to a measuring unit. In the measuring unit after the noise components are removed from the electric signals, the electric signals are used for the measurement of fine particles. The structure and operation of the above described measuring unit are as described with reference to FIGS. 17 and 18.

In the present application, for good understanding of this invention the method and systems according to the first to the twelfth aspects of this invention are explained respectively by means of different embodiments and modifications, but the intensity distributions of the laser beam, the scanning means and method, the optical systems, the measuring units, etc. are adaptable to the methods and systems according to all the aspects of this invention.

The first to the twelfth aspects of this invention relate to novel fine particle measuring methods and systems. The following thirteenth to the fourteenth aspects of this invention relate to flow passage members (flow cells) for use in the fine particle measuring systems of this invention and attains the fourth object of this invention described above.

THIRTEENTH AND FOURTEENTH ASPECTS OF THE INVENTION

Figure 43:
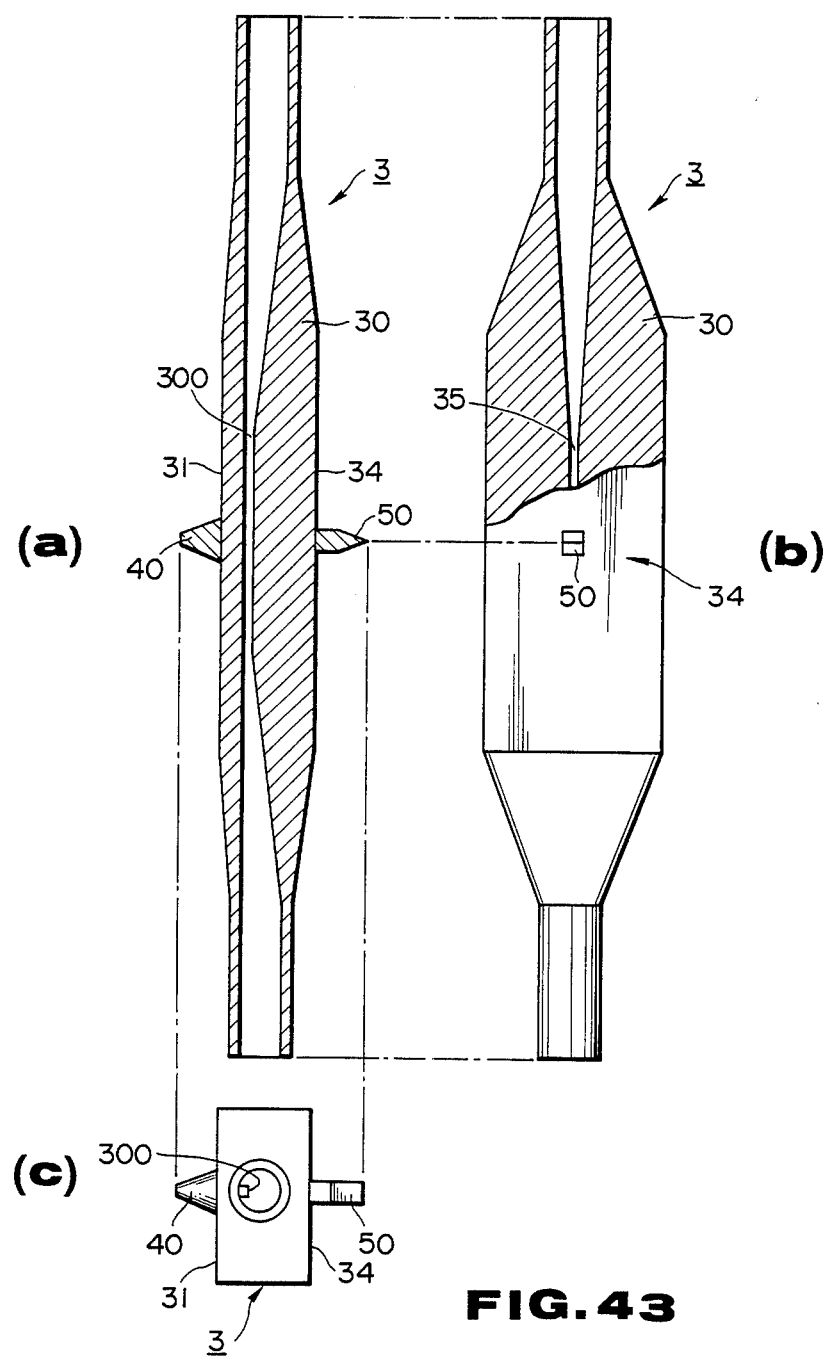
FIG. 43 is a view showing the structure of the flow cell of a first embodiment of the flow cell according to the thirteenth and the fourteenth aspects.
Figure 44:
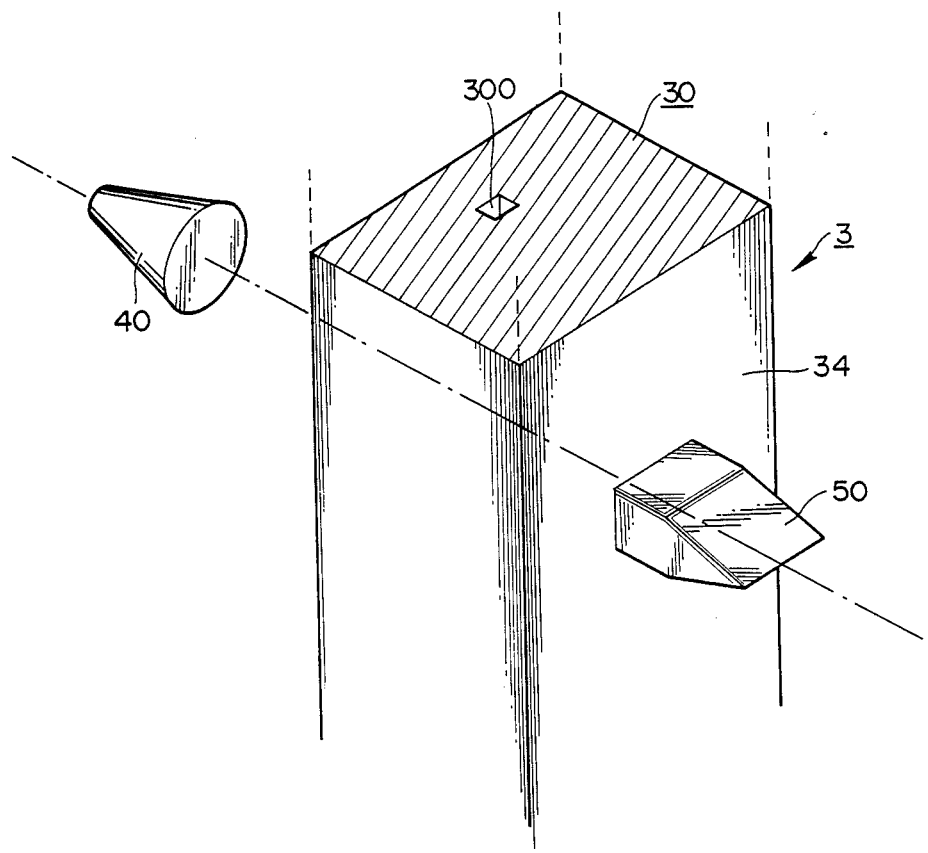
FIG. 44 is a broken perspective view of a main part of the flow cell of FIG. 43.

FIG. 43 shows the structure of a first embodiment of the flow cells according to a thirteenth and a fourteenth aspects of this invention. FIG. 43(a) is a sectional side view, and FIG. 43(b) is a partially broken sectional area view, and FIG. 43(c) is a plan view. FIG. 44 is a broken perspective view of a main part of the first embodiment of the flow cells. As shown in FIGS. 43 and 44, a flow cell 3 comprises, e.g., a tubular member 30 of quartz, an incident block secured to the tubular member 30, and beam trap member 50. The flow cell 3 is for measuring fine particles by dispersing stationary (not scanning) measuring laser beam in forward direction thereof. The beam trap member 50 is secured to a fourth place (a transmission surface for measuring laser beam) of the flow cell 3 which is finished flat and smooth as an observation surface of sacttered lights. A flow passage in the flow cell 3 has square section and has a light scattering portion is in alignment with the incident block 40 and with the beam trap member 50.

FIG. 45 is section views of a main part of the flow cell 3 shown in FIGS. 43 and 44. FIG. 45(a) is longitudinal sectional view, and FIG. 45(b) is a cross sectional view. In FIG. 45, transmission portions for measuring laser beam in the surfaces 31-34 of the tubular member 30 are parallel with one another. The incident block 40 in a frustoconical shape has the top surface finished flat and smooth, which provides an incident plane 41 for a laser beam 2 to be incident on. The flat and smooth surface opposite to the incident plane 41 has a focus aperture plane 42 and is adhered to the first surface of the flow cell 3 through a refractive index adjusting liquid (e.g., an adhesive for the optical use having substantially the same refractive index as the tubular member 30 and the incident block 40). The outside surfaces of the other surfaces of the incident block 40 is coated with a light absorptive film 43, so that the size of the focus aperture surface set in the surface where the incident block 40 is adhered to the first surface 31 of the flow cell 3. The beam trap is secured to the fourth surface 34 of the flow cell 3. The beam trap 50 has a little longer horizontal sides and is secured to the flow cell 3 at the surface 51 which is finished flat and smooth, and is adhered to the fourth surface 34 through a refractive index adjusting liquid. The outside surface of the other surface of the beam trap 50 is coated with a light absorptive film 52. The transmission portions for the measuring laser beam of the tubular member 30, the incident block 40 and the beams trap 50 are made of materials having substantially the same refractive index (e.g, quartz), and the light absorptive films 43,52 can be prepared by mixing an organic material having substantially the same refractive index with a particulate material (e.g., carbon black), and applying the thus prepared mixture to the surfaces. This makes changes of refractive indexes at the surfaces of the adhesion ignorably trivial.

Next, the function of the flow cells according to the thirteenth and the fourteenth aspects will be explained with reference to FIG. 46.

Figure 46:
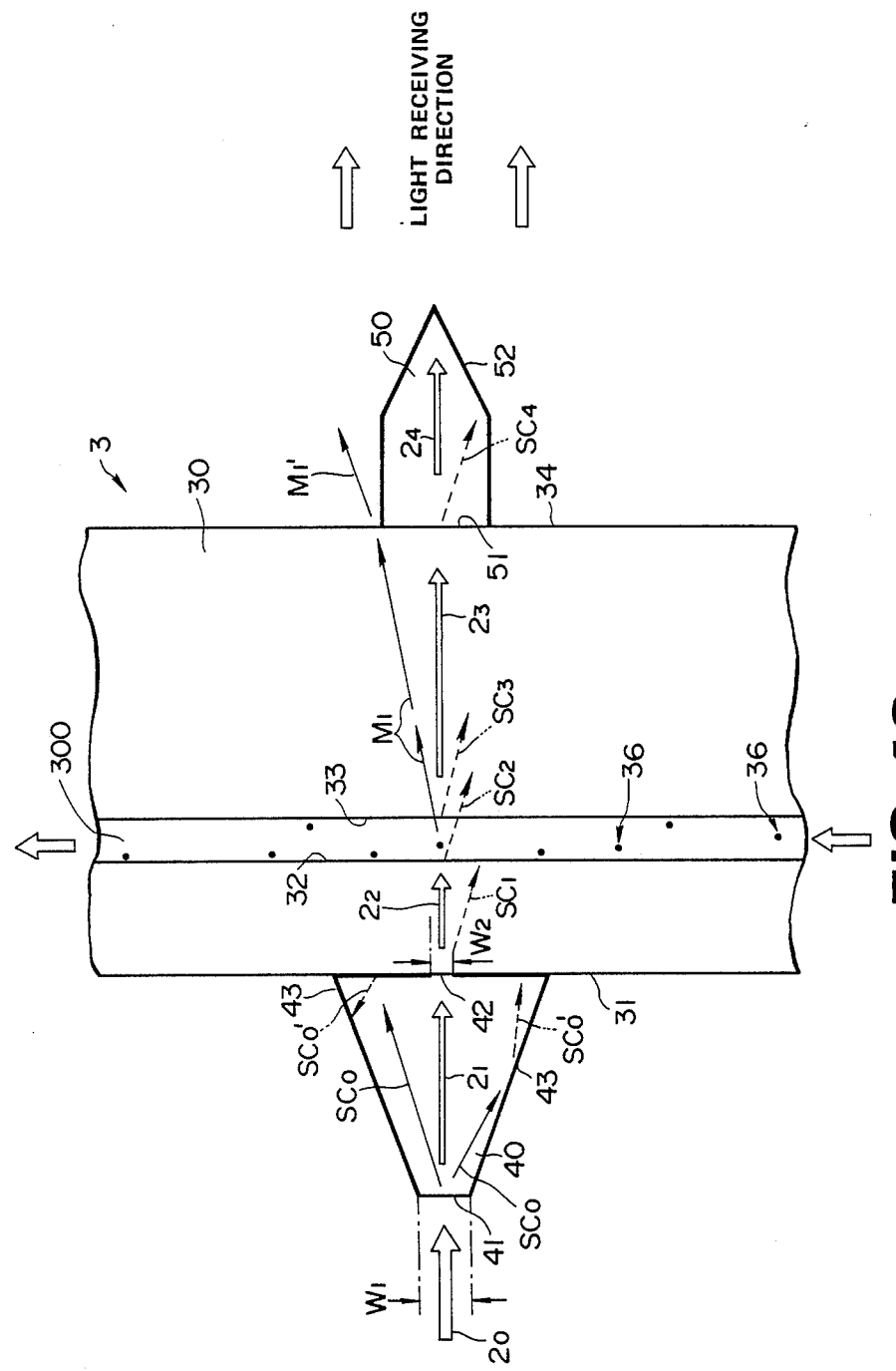
FIG. 46 is an explanatory view of the operation of the flow cell according to the first embodiment of FIGS. 43 to 45.

In FIG. 46, a measuring beam (laser beam) $2_0$ is incident on a plane of incidence 41 and into the incident block 40. At this time, the laser beam $2_0$ is scatered at the plane of incidence 41 of the incident block 40, and scattered lights $SC_0$ are formed in the incident block 41. Most of the scattered light $SC_0$ are incidented on the light absorptive film 43 and absorbed. Thus reflected lights $SC_0'$ become substantially ignorably weak. Then the measuring laser beam $2_1$ is incident on the tubular member 30 through the focus aperture surface 42. By making the focus aperture surface 42 sufficiently small relative to the beam diameter of the laser beam $2_1$, most of the scattered lights $SC_0$ can be absorbed in the incident block 40.

It is considered that when the laser beam $2_1$ is incident on the tubular block 30 from the incident block 40, scattered lights $SC_1$ are formed at the boundary surface between the focus aperture surface 42 and the first surface 31 of the tubular member 30. But the scattered light $SC_1$ are substantially ignorable, because the tubular member 30 and the incident block 40 are made of a material (quartz) of the same refractive index and are adhered through a refractive index adjusting liquid having the same reflective index as their material, and a difference in the refractive index is trivial. Scattered light $SC_2$ and $SC_3$ at the respective boundary surfaces between a sample fluid (e.g., water) and the second surface 32 of the tubular member 30, and between the former and the second surface 33 of the latter are substantially insignificant because of an ignorable small difference between quartz and a sample fluid (e.g., water).

The laser beam $2_3$ in the tubular member 30 is incident on the fourth surface 34 of the tubular member 30 and the surface 51 of the beam trap 50 which is secured to the tubular member into the beam trap 50. The laser beam $2_4$ is absorbed efficiently by the light absorptive film 52 applied to the outside surface of the beam trap member 50. Scattered lights $SC_4$ is ignorably weak at the boundary surface between the fourth surface 34 of the tubular member 30 and the surface 51 because the beam trap 50 and the tubular member 30 are made of a material of the same refractive index (quartz) and adhered through a refractive index adjusting liquid of the same refractive index as the material, and the scattered light $SC_4$ are absorbed by the light absorptive film 52. None of the scattered lights $SC_4$ do not reach a light detector disposed in a light receiving direction.

Scattered lights $M_1$ formed when the laser beam 2 incident on fine particles 36 in the flow passage 300 go outside through the fourth surface 34 finished flat and smooth and are received as measured scattered lights $M_1'$ by the light detector (no shown). Thus the scattered light $M_1'$ is substantially free from the influence of the scattered lights $SC_1$ and $SC_4$ at the first surface 31 and the fourth surface 34 of the tubular member 30, which has been a problem. Furthermore, the influence of reflected lights reciprocating once to several times between the first surface 31 and the fourth surface 34 can be ignorable by adjusting the direction of the laser beam $2_0$ so that the reflected lights may be captured by the beam trap 50 having a little longer sides and an opening (in the secured surface 51). Even in the case that taking into consideration the trapping of the reciprocal reflected lights, the dimensions of the beam trap 50 have an allowance, the incident block 40 and the beam trap 50 are still very compact, and consequently the system as a whole can be miniaturized and its cost can be reduced.

Next, the structure and function of a second embodiment of the flow cell according to the thirteenth and the fourteenth aspects of the invention will be explained with reference to FIG. 47.

FIG. 47(a) is a front view of an incident block 40. FIG. 47(b) is a side sectional view of a main part of a flow cell 3 also for the explanation of the function thereof. FIG. 47(c) is a front view of a beam trap 50. As shown in FIG. 47(a), the incident block 40 is in a generally pyramidal shape, and the outside surface of the incident block is coated with a light absorptive film 43 except for a plane of incidence 41 and a focus aperture surface 42. As shown in FIG. 47(b) the incident block 40 is adhered to a first surface 31 of a tubular member 30 through a refractive index adjusting liquid. As shown in FIG. 47(c), the beam trap 50 is in a pyramidal shape and is coated with a light absorptive film 52 except for a surface 51 thereof which is secured to a fourth surface 34 of the tubular member 30 and is secured to the fourth surface 34 of the tubular member 30 through a refractive index adjusting liquid 30 as shown in FIG. 47(b).

Figure 47:
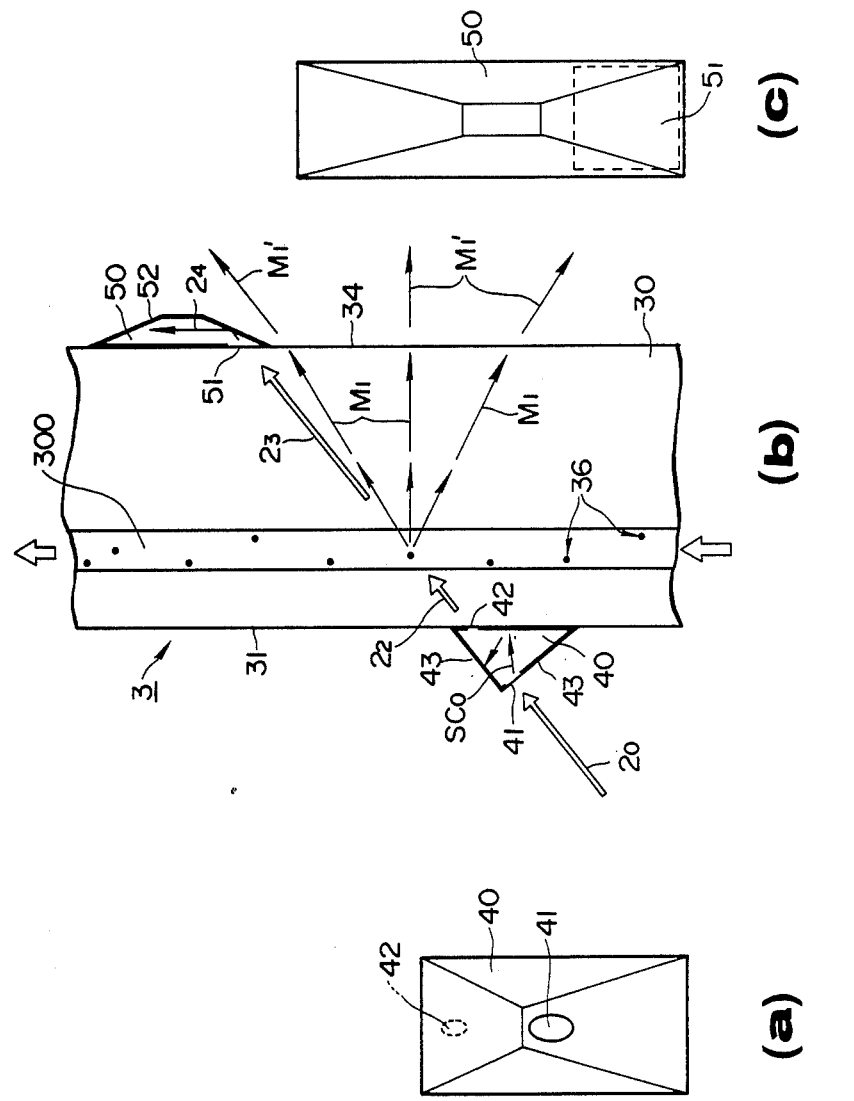
FIG. 47 is explanatory views of main parts of a second embodiment of the flow cell according to the thirteenth and the fourteenth aspects.

As shown in FIG. 47, the flow cell according to this second embodiment is for measuring fine particles by dispersing stationary (not scanning) laser beam in the near forward direction thereof. The plane of incidence of the incident block 40, the focus aperture surface 41 and the secured surface 51 of the beam trap 50 are disposed in the optical path of a measuring laser beam $2_0$, so that the laser beam $2_0$ is incident on the plane of incidence 40 of the incident block 40 orthogonally thereto. The fourth surface of the tubular member 30 on the side of observation is finished smooth and flat.

Next, the function of the flow cell of FIG. 47 will be explained.

When the laser beam $2_0$ is incident on the plane of incidence 41 of the incident block 40, scattered lights $SC_0$ are formed. Most of the scattered lights are absorbed by the light absorbing film 43 of the incident block 40. Almost no scattered light is formed at the boundary surface between the focus aperture surface 42 of the incident block 40 and the first surface 31 of the tubular member 30 because both are adhered through a refractive index adjusting liquid. This contributes to a great reduction of the formation of scattered lights when the laser beam 2 is incident thereon.

The laser beam $2_2$ which has entered a flow passage 300 is incident on fine particles 36, and scattered lights $M_1$ are formed. The scattered lights $M_1$ go out of the tubular member 30 through the surface 34 and received as measured scattered lights $M_1'$ by a light detector. On the other hand, the laser beams $2_3$ which has passed the flow passage 300 enters the beam trap 50 through the fourth surface 34 and the secured surface 51, while the measured laser beam $2_4$ is absorbed efficiently by the light absorptive film 52 on the outside surface of the beam trap 50. At this time the scattered lights formed on the boundary surface between the tubular member 30 and the beam trap 50 is ignorable because a difference in the refractive index between the two is ignorable. The reflecting lights reciprocating between the surfaces of the tubular member 30 move upward and thus do not reach the light detector.

According to the second embodiment, the adverse influence caused by the light scattering on the first and the fourth surfaces of the tubular member 30 can be much reduced, as in the first embodiment. Besides, compared with the conventional flow cell of the near forward light scattering type, the beam trap 50 can be made much more compact.

The flow cell according to the thirteenth and the fourteenth aspects of this invention is not limited to the above described embodiments and covers various modifications.

FIGS. 48 to 50 are explanatory views of the incident block 41 and the beam trap 50. FIG. 48(a) is an enlarged view of the incident block 40 and the beam trap of FIG. 43 and is usable in the forward light scattering type using stationary beam. FIG. 48(b) shows the incident block and the beam trap, which is large sized, usable in the sidewise light scattering type using stationary beam. In the sidewise light scattering type as shown in FIG. 48(b), the scattered lights dispersed sidewise are not detected, and thus the beam trap 50 is coated with a light absorptive film except for a laser beam transmitting area of the bottom surface thereof.

FIG. 49(a) shows the incident block and the beam trap which are usable in the forward light scattering type using horizontally scanning laser beam. The top surface of the incident block 40 provides the plane of incidence 41. The bottom surface of the incident block 40 provides the focus aperture surface 42, which is smaller than the plane of incidence 41. The incident block 40 and the beam trap 50 are formed elongated in the scanning direction so that they can receive the scanning laser beam.

FIG. 49(b) shows the incident block and the beam trap usable in the forward light scattering type using laser beam scanning in the deflected direction by 45. The incident block 40 and the beam trap 50 are formed elongated in the scanning direction. The incident block 40 has the top formed in the plane of incidence 41, and the focus aperture surface opposed to the plane of incidence 41 is made smaller than the plane of incidence 41. When this is used in the sidewise light scattering type, the beam trap 50 may be larger.

FIG. 50(a) shows the incident block and the beam trap usable in the near forward light scattering type using stationary laser beam and is the same as the second embodiment of FIG. 47. FIG. 50(b) shows the incident block and the laser beam usable in the near forward light scattering type using horizontally scanning laser beam. The incident block 40 and the beam trap 50 are made larger toward the scanning direction of the laser beam. The plane of incidence 41 of the incident block 40 is elongated in the scanning direction of the laser beam, and the focus aperture surface 42 is elongated in the scanning direction, as the plane of incidence 41 is, and is made narrower in the direction orthogonal to the scanning direction.

As described above, preferable embodiments of the flow cell according to the thirteenth and the fourteenth aspects of this invention have been explained. In every embodiment, the incident block 40 and the beam trap 50 are secured to the tubular member 30. But the beam trap 50 is not essentially as described above, and only the incident block 40 may be secured to the tubular member 30. Such arrangement still produces sufficient effect. In other words, it is not easy, especially in the forward light scattering type, that the scattered lights on the first surface are trapped, and the scattered lights on the first surface can be much easily trapped compared with those on the first surface.

To be specific, if the incident block 40 is secured to the tubular member 30, the scattered lights formed when the laser beam 2 is incident are absorbed in the incident block 40, and when the laser beam is incident on the tubular member 30 from the incident block 40, no scattered lights are formed because of no difference in the refractive index on the boundary surface between the two. Thus, without the beam trap 50 secured to the fourth surface of the tubular member 30, the noise resulting from the stray lights can be satisfactorily removed.

Figure 1:
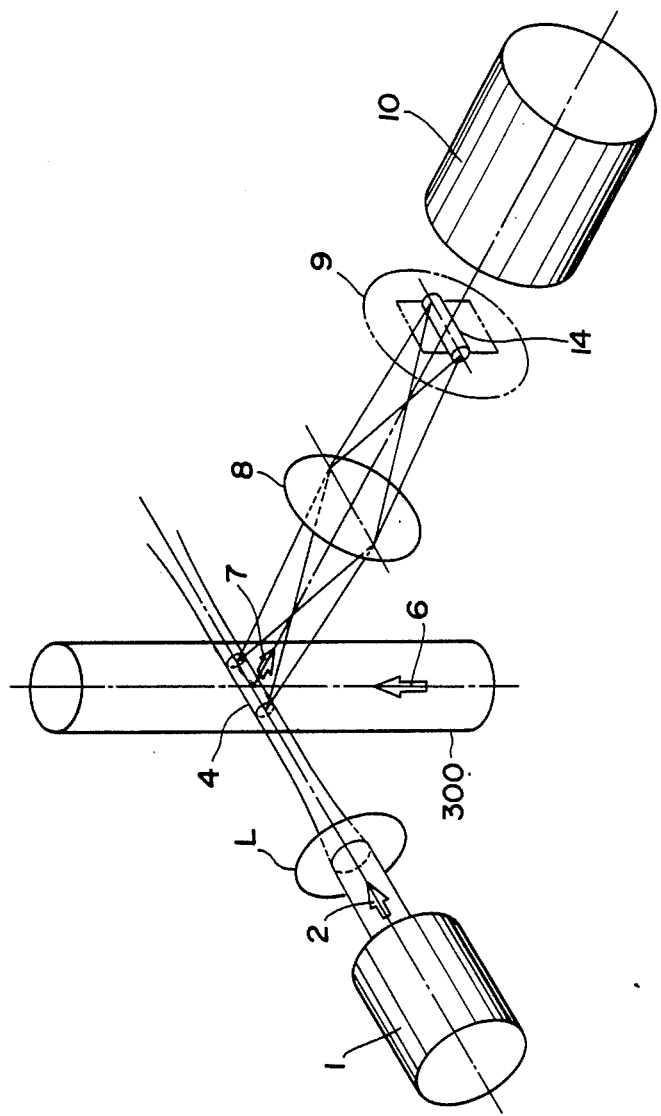
FIG. 1 is a perspective view of one example of the conventional system of the sidewise scattering type.
Figure 2:
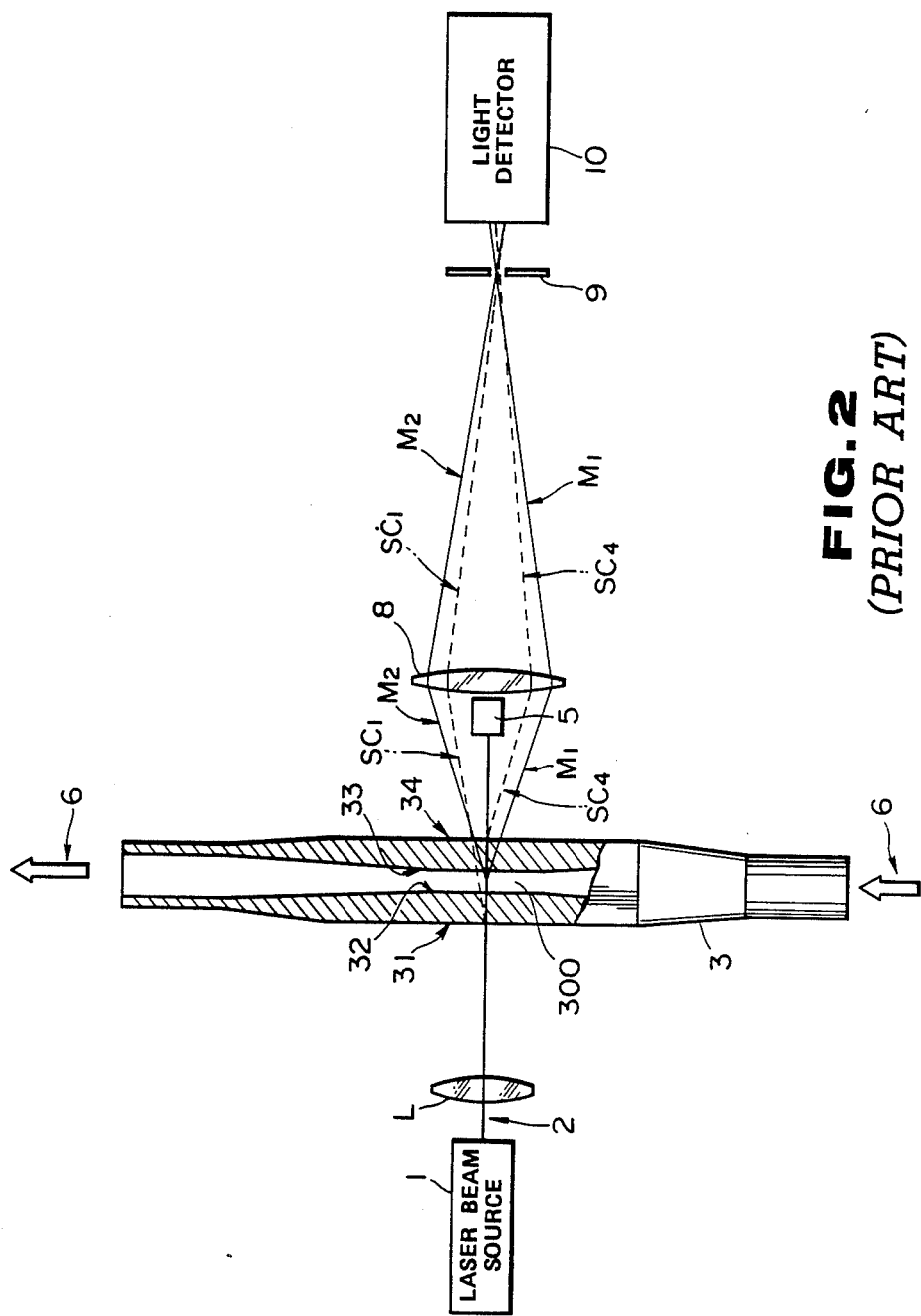
FIG. 2 is an explanatory view of the structure and operation of a conventional flow cell of the forward scattering type.

In the case that the beam trap 50 is not secured to the fourth surface 34 of the tubular member 30, the beam trap e,g., shown in FIG. 2 is necessary, and it is preferable that the beam trap is disposed near the fourth surface of the tubular member as much as possible. Instead, a total reflecting prism is disposed at the position of the beam trap in place of the beam trap so as to reflect the laser beam to be received by a separate beam trap. Besides, the total reflecting prism is secured to the fourth surface of the tubular member 30 through a refractive index adjusting liquid so as to decrease the formation of the scattered lights on the fourth surface 34 of the tubular member 30 which produces an advantageous effect of more decreasing the noise due to the stray lights.

The beam trap secured to the fourth surface of the tubular member 30 may be made of black quartz. The beam trap of black quartz prevents the formation of the scattered light on the fourth surface 34 and can capture the laser beam. Light absorptive trapping materials may be adhered or coated.

I claim:

1. A fine particle measuring method in which laser beam having an intensity gradually increasing over at least the peripheral portion thereof and a portion inner of and near to the peripheral portion inward from the peripheral is radiated to fine particles in a sample fluid flowing in a given direction and at a given flow speed in an direction to intersect a flow direction of said sample fluid, and scattered lights dispersed against the fine particles in light scattering region are detected comprising:
    a first step of forming said laser beam into at least two parallel beams having respective intensity distributions, deviating from each other in a direction orthogonal both to said flow direction of same sample fluid and a direction of the laser beam in a range in which the beam spots of said laser beams overlap each other in said flow direction of said sample fluid, and deviating from each other by a given distance in said flow direction,
    a second step of detecting at least two scattered lights successively formed by one and the same one of said fine particles passing said two parallel beams among the scattered lights formed by said fine particles passing said at least two parallel beams;
    a third step of selecting an area of said light scattering region to be detected based on the value of at least two detected outputs given by the second step; and
    a fourth step of measuring particle diameters of said fine particles based on the value of said at least two detected outputs in the area selected by the third step.

2. The fine particle measuring method according to claim 1, wherein said at least two parallel laser beams are so spaced from each other that at least physical optical interference may not take place therebetween in said light scattering region.

3. The fine particle measuring method according to claim 1, wherein the detection of said at least two scattered lights in the second step is carried out at a time interval in which a given time passes from the detection of a preceding scattered light, or at a time interval after a preset time has passed from the detection of a preceding scattered light.

4. The fine particle measuring method according to claim 1, wherein the value of the detected outputs given by the third step is a maximum value or an integrated value of the detected outputs given by the second step.

5. The fine particle measuring method according to claim 1, wherein a fourth step measures the particle diameters of said fine particles, based on the value of said at least two detected outputs in the area selected by the third step, and a time width of at least one of said at least two detected outputs.

6. The fine particle measuring method according to claim 1, wherein the first step is for forming said laser beam into at least two parallel beams which have different intensity distributions from each other, the beam spots of which substantially overlap each other in said flow direction of said sample fluid, and which deviate from each other by a given distance in said flow direction.

7. The fine particle measuring method according to claim 6, wherein said at least two parallel beams formed by the first step are so spaced from each other that at least physical optical interference may not take place therebetween in said light scattering region.

8. The fine particle measuring method according to claim 6, wherein the detection of said at least two scattered lights in the second step is carried out at a time interval in which a given time passes from the detection of a preceding scattered light, or at a time interval after a preset time has passed from the time of the detection of a preceding scattered light.

9. The fine particle measuring method according to claim 6, wherein the value of the detected outputs given by the third step are a maximum value or an integrated value of the detected outputs given by the second step.

10. The fine particle measuring method according to claim 6, wherein a fourth step measures the particle diameters of said fine particles, based on the value of said at least two detected outputs in the area selected by the third step, and a time width of at least one of said at least two detected outputs.

11. The fine particle measuring method according to claim 1, wherein the first step forms said laser beam into a first and a second parallel laser beams having respective given intensity distributions, deviating from each other in a direction orthogonal both to said flow direction of said sample fluid and a direction of the laser beams in a range in which the beam spots of said laser beams overlap each other in said flow direction of said sample fluid, and deviating from each other by a given distance in said flow direction, and into a third parallel laser beam deviating from said first and second parallel beams by a given distance in a range in which the beam spots of said first and second parallel beams overlap each other in said flow direction,
the second step detects three scattered lights successively formed by one and the same one of said fine particles passing said first to said third laser beams among the scattered lights formed by said fine particles passing said first to said third beams,
the fourth step measures particle diameters of said fine particles, based on a value of said three detected outputs in the area selected by the third step.

12. The fine particle measuring method according to claim 11, wherein the third step selects an area of said light scattering region to be detected, based on at least two values of the three detected outputs given by the second step.

13. The fine particle measuring method according to claim 11, wherein the first step is for forming said laser beam into a first and a second parallel beams which have different intensity distributions from each other, the beam spot of which overlap each other in said flow direction of said sample fluid, and which deviate from each other by a given distance in said flow direction, and a third parallel beam deviating from said first and second parallel beams by a given distance in a range in which the beam spots of said first and second parallel beams overlap each other.

14. The fine particle measuring method according to claim 13, wherein the third step selects an area of said light scattering region to be detected, based on at least two values of the three detected outputs given by the second step.

15. A fine particle measuring method in which laser beam having an intensity gradually increasing over at least the peripheral portion thereof and a portion inner of and near to the peripheral portion inward from the peripheral portion is radiated to fine particles in a sample fluid flowing speed in a direction to intersect a flow direction of said sample fluid, and scattered lights dispersed on the fine particles in a light scattering region are detected comprising:

a first step of forming said laser beam into at least two parallel beams having respective intensity distributions, deviating from each other in a direction orthogonal both to said flow direction of said sample fluid and a direction of said laser beam in a range in which the beam spots of said laser beams overlap each other in said flow direction of said sample fluid, and deviating from each other by a given distance in said flow direction;

a second step of detecting scattered lights dispersed on said fine particles passing said at least two parallel beams;

a third step of measuring a time interval between at least two successive detected outputs of the scattered lights detected by the second step;

a fourth step of extracting a pair of detected outputs of one and the same one of said fine particles, based on the time interval measured by the third step;

a fifth step of selecting an area of said light scattering region to be detected, based on a value of said at least two detected outputs of the pair extracted by the fourth step; and a sixth step of measuring particle diameters of said fine particles, based on the value of said at least two detected outputs in said light scattering region in the area selected by the fifth step.

16. The fine particle measuring method according to claim 15, wherein said at least two parallel laser beams formed by the first step are so spaced from each other that at least physical optical interference may not take place therebetween in said light scattering region.

17. The fine particle measuring method according to claim 15, wherein the time interval between the detected outputs given by the third step is a time interval between the maximum values of the detected outputs given by the second step.

18. The fine particle measuring method according to claim 15, wherein the fourth step extracts a pair of said detected outputs, based on a peak of the occurrences of the time interval measured by the third step.

19. The fine particle measuring method according to claim 15 further comprising, in addition to the first to the sixth step:
a seventh step of computing a volume of said sample fluid passing the area of said light scattering region selected by the fifth step, based on the time interval measured by the third step; and
an eighth step of computing a particle diameter distribution, based on the particle diameters measured by the sixth step, and the volume of said sample fluid computed by the seventh step.

20. The fine particle measuring method according to claim 15, wherein the first step forms said laser beam into at least two parallel beams which have different intensity distributions from each other, the beam spots of which overlap each other in said flow direction of said sample fluid, and which deviate from each other by a given distance in said flow direction of said sample fluid.

21. The fine particle measuring method according to claim 20, wherein said at least two parallel beams are so spaced from each other that at least physical optical interference may not take place therebetween in said light scattering region.

22. The fine particle measuring method according to claim 20, wherein the time interval between the detected outputs given by the third step is a time interval between the maximum values of the detected outputs given by the second step.

23. The fine particle measuring method according to claim 20, wherein the fourth step extracts a pair of said detected outputs, based on a peak of the occurrences of the time interval measured by the third step.

24. The fine particle measuring method according to claim 20 further comprising, in addition to the first to the sixth step:
   a seventh step of computing a volume of said sample fluid passing the area of said light scattering region selected by the fifth step, based on the time interval measured by the third step; and
   an eighth step of computing particle diameter distributions, based on the particle diameters measured by the sixth step, and the volume of said sample fluid given by the seventh step.

25. A fine particle measuring system comprising:
   at least one laser beam source;
   a first optical system for forming a laser beam from said laser beam source into at least two parallel beams which have respective given intensity distributions, which deviate from each other in a direction orthogonal both to a flow direction of a sample fluid and a direction of said laser beam in a range in which the beam spots of said laser beams overlap each other in said flow direction of said sample fluid, and which deviate from each other by a given distance in said flow direction;
   a flow passage for the sample fluid containing fine particles to flow through in a given direction, arranged so that said fine particles intersect said at least two parallel laser beams;
   a second optical system for forming scattered lights formed by said fine particles passing said at least two parallel laser beams into images at a given image point;
   light detecting means for detecting the scattered lights formed into the images by the second optical system to generate detected outputs; and
   measuring means for extracting scattered lights from one and the same one of said fine particle, based on a time interval between at least two detected outputs successively generated, selecting an area of a light scattering region to be detected, based on the ratio between values of said at least two detected outputs, and measuring particle diameters of said fine particles, based on the value of said at least two detected outputs thus extracted and selected.

26. The fine particle measuring system according to claim 25, wherein said at least two parallel beams from the first optical system are so spaced that at least physical optical interference may not take place therebetween in said light scattering region.

27. The fine particle measuring system according to claim 25, wherein the extraction of the scattered lights from one and the same one of said fine particles by said measuring means is carried out at a time interval in which a given time passes from the detection of a preceding scattered light, or at a time interval after a preset time has passed from the detection of a preceding scattered light.

28. The fine particle measuring system according to claim 25, wherein the time interval between the detected outputs processed by said measuring means is a time interval between the maximum values of said detected outputs.

29. The fine particle measuring system according to claim 25, wherein a ratio between the values of said detected outputs processed by said measuring means is a ratio between the maximum values of said detected outputs or that between the integrated values thereof.

30. The fine particle measuring system according to claim 25, wherein said measuring means computes a volume of said sample fluid passing said selected area of the light scattering region, based on the time interval between said at least two detected outputs successively generated, and computing particle diameter distributions, based on said particle diameters and said volume of said sample fluid.

31. The fine particle measuring system according to claim 25, wherein said measuring means removes noise components from said at least two detected outputs to obtain at least two detected light outputs, extracting scattered lights of one and the same one of said fine particles, based on a time interval between said at least two detected light outputs; selecting an area of said light scattering region to be detected, based on the ratio between values of measured outputs based on said at least two detected light outputs, and measuring particle diameters of said fine particles, based on the value of said at least two measured outputs extracted and selected.

32. The fine particle measuring system according to claim 25, wherein the value of said measured outputs is a maximum value of said detected light outputs or an integrated value thereof.

33. The fine particle measuring system according to claim 25, wherein said first optical system forms said laser beam into at least two parallel laser beams which have different intensity distributions from each other, the beam spots of which overlap each other in said flow direction of said sample fluid, and which deviate from each other by a given distance in said flow direction.

34. The fine particle measuring system according to claim 33, wherein said at least two parallel beams from said first optical system are so space from each other that at least physical optical interference may not take place therebetween in said light scattering region.

35. The fine particle measuring system according to claim 33, wherein the extraction of the scattered lights from one and the same one of said fine particles by said measuring means is carried out at a time interval in which a given time passes from the detection of a preceding scattered light, or a time interval after a preset time has passed from the detection of a preceding scattered light.

36. The fine particle measuring system according to claim 33, wherein the time interval of detected output processed by said measuring means is a time interval between the maximum values of said detected outputs.

37. The fine particle measuring system according to claim 33, wherein a ratio between the values of the detected outputs processed by said measuring means is a ratio between the maximum values of said detected outputs, or a ratio between the integrated values thereof.

38. The fine particle measuring system according to claim 33, wherein said measuring means computes a volume of said sample fluid passing said selected area of the light scattering region, based on the time interval between said at least two detected outputs successively generated, and computes particle diameter distributions of said fine particles, based on said particle diameters and said volume of the sample fluid.

39. The fine particle measuring system according to claim 33, wherein said measuring means removes noise components from said at least two detected outputs to obtain at least two detected light outputs, extracting the scattered lights of one and the same one of said fine particles, based on a time interval between said at least two detected light outputs; selecting an area of said light scattering region to be detected, based on a value of measured outputs based on said at least two detected light outputs, and measuring particle diameters of said fine particles, based on the values of said at least two measured outputs extracted and selected.

40. The fine particle measuring system according to claim 33, wherein the value of said measured outputs is a maximum value of said detected light outputs or an integrated value thereof.

41. A fine particle measuring method in which a laser beam having an intensity gradually increasing over at least peripheral portion thereof and a portion near to and inner of the peripheral portion inward from the peripheral portion is radiated to fine particles in a sample fluid flowing in a given direction and a given flow speed in a direction intersecting a flow direction of said sample fluid, and scattered lights form said fine particles in a light scattering region are detected comprising:
 a first step of forming said laser beam into two parallel linear polarized beams having respective given intensity distributions, deviating from each other in a direction substantially orthogonal both to said flow direction and a direction of the laser beam in a range in which the beam spots of said laser beams overlap each other, and having the polarization planes thereof orthogonal to each other;
 a second step of detecting two scattered lights formed simultaneously by said fine particles passing said two linear polarized beams;
 a third step of selecting an area of said light scattering region, based on a value of two detected outputs given by the second step; and
 a fourth step of correcting the value of said two detected outputs by preset procedure in the area selected by the third step, and, based on a result of the correction, measuring particle diameters of said fine particles.

42. The fine particle measuring method according to claim 41, wherein the value of the detected outputs used in the third step is a maximum value or an integrated value of the detected outputs obtained by the second step.

43. The fine particle measuring method according to claim 41, wherein the fourth step measures particle diameters of said fine particles, based on the value of said two detected outputs in the area selected by the third step, and a time width of at least one of said two detected outputs.

44. The fine particle measuring method according to claim 41, wherein the first step forms the laser beam into two parallel linear polarized beams which have different intensity distributions from each other, the beam spots of which overlap each other, and the polarization planes of which are substantially orthogonal to each other.

45. The fine particle measuring method according to claim 44, wherein the value of the detected outputs used in the third step is a maximum value or an integrated value of the detected outputs obtained by the second step.

46. The fine particle measuring method according to claim 44, wherein the fourth step measures particle diameters of said fine particles, based on the value of said two detected outputs in the area selected by the third step, and a time width of at least one of said two detected outputs.

47. The fine particle measuring method according to claim 41, wherein the first step of forming said laser beam into a first and a second parallel linear polarized beams having respective given intensity distributions, deviating from each other in a direction substantially orthogonal both to said flow direction and said direction of said laser beam in a range in which the beam spots of said laser beams overlap, and into a third parallel beam which deviates from said first and said second linear polarized beams by a given distance in said flow direction in a range in which the beam spots of said first and the second linear polarized beams overlap each other, and the beam spot of which deviates from the positions of the beam spots of said first and second linear polarized beams by a given distance in said direction of the laser beam,
 the second step detects three scattered lights successively formed by one and the same one of said fine particles passing said first and second linear polarized beams and said third parallel beam among scattered lights formed by said fine particles passing said first and second linear polarized beams and said third parallel beam, and
 the third step selects an area of said light scattering region to be detected, based on at least two values of the three detected outputs detected by the second step, and
 the fourth step measures particle diameters of said fine particles, based on the values of said three detected outputs in the area selected by the third step.

48. The fine particle measuring method according to claim 47, wherein the first step forms the laser beam into a first and a second parallel linear polarized beams which have different intensity distributions from each other, the beam spots of which overlap each other, and which have polarization planes substantially orthogonal to each other, and into a third parallel beam which deviates from said first and second linear polarized beams by a given distance in a range in which the beam spots of said first and second linear polarized beams overlap each other, and the beam spot of which deviates from the positions of the beam spots of said first and second linear polarized beams by a given distance in said direction of the laser beam.

49. The fine particle measuring method in which laser beam having an intensity gradually increasing over at least peripheral portion thereof and a portion near to and inner of the peripheral portion inward from the peripheral portion is radiated to fine particles in a sample fluid flowing in a given direction in a direction to intersect a flow direction of said sample fluid, and scattered lights form said fine particles in a light scattering region are detected comprising:
 a first step of forming said laser beam into a first and a second linear polarized beams, being parallel each other, having respective given intensity distributions, deviating from each other in a direction substantially orthogonal both to said flow direction and said direction of said laser beam in a range in which the beam spots of said laser beams overlap each other, and which have polarization planes substantially orthogonal to each other, and into a third parallel beam which deviates from said first and a second linear polarized beams by a given distance in said flow direction in a range in which the beam spots of said first and the second linear polarized beams overlap each other a second step of detecting a first to a third scattered lights formed by said fine particles passing said first and second linear polarized beams, and said third parallel beam a third step of measuring a time interval between a detected output of at least one of said first and said second scattered lights, and a detected output of said third scattered light;

a fourth step of extracting a pair of detected outputs of one and the same one of said fine particles, based on a time interval measured by the third step;

a fifth step of selecting an area of said light scattering region to be detected, based on a value of the pair of detected outputs of said first and second scattered lights detected substantially simultaneously by the second step;

a sixth step of measuring particle diameters of said fine particles, based on the value of said detected outputs of said first and second scattered lights in the area of said light scattering region selected by the fifth step;

a seventh step of computing a volume of said sample fluid passing the area of said light scattering region selected by the fifth step, based on the time interval measured by the third step; and an eighth step of computing particle diameter distributions, based on the particle diameters measured by the sixth step, and the volume of said sample fluid computed by the seventh step.

50. The fine particle measuring method according to claim 49, wherein said third parallel beam formed in the first step is so spaced from said first and second linear polarized beams that at least physical optical interference may not take place therebetween in said light scattering region.

51. The fine particle measuring method according to claim 49, wherein the time interval between the detected outputs is a time interval between the maximum values of the detected outputs generated by the second step.

52. The fine particle measuring method according to claim 49, wherein the fourth step extracts a pair of detected outputs, based on a peak of the occurrences of the time interval measured by the third step.

53. The fine particle measuring method according to claim 49, wherein the first step forms the laser beam into a first and a second parallel beams which have respective different intensity distributions from each other, the beam spots of which overlap each other, and which have their polarization planes orthogonal to each other, and into a third parallel beam deviating from said first and second linear polarized beams by a given distance in said flow direction in a range in which the beam spots of said first and the second linear polarized beams overlap each other.

54. The fine particle measuring method according to claim 53, wherein the third parallel beam formed in the first step is so spaced from said first and second linear polarized beams that at least physical optical interference may not take place in said light scattering region.

55. The fine particle measuring method according to claim 53, wherein the time interval between the detected outputs generated by the third step is a time interval between the maximum values of the detected outputs obtained by the second step.

56. The fine particle measuring method according to claim 53, wherein the fourth step extracts a pair of detected outputs, based on a peak of the occurrences of the time interval measured by the third step.

57. A fine particle measuring system comprising:

at least one laser beam source;

a first optical system for forming the laser beam from said laser beam source into parallel two linear polarized beams having respective given intensity distributions, deviating from each other in a direction orthogonal both to a flow direction of a sample fluid and a direction of said laser beam, and having their polarization planes orthogonal to each other;

a flow passage for a sample fluid containing fine particles to flow in a given direction arranged to intersect said two linear polarized beams;

a second optical system for forming scattered lights of said two polarized beams into images on a given image point;

polarizing and dividing means for dividing the scattered lights formed in the images by the second optical system according to the polarization planes;

light detecting means for detecting two respective divided scattered lights and generating detected outputs and;

measuring means for selecting an area of a light scattering region to be detected, based on a value of said two detected outputs detected substantially simultaneously, and measuring particle diameters of said fine particles, based on the value of said selected two detected outputs in said selected area.

58. The fine particle measuring system according to claim 57, wherein a ratio of the values of the detected outputs processed by said measuring means is a ratio between the maximum values of said detected outputs or a ratio between the integrated values thereof.

59. The fine particle measuring system according to claim 57, wherein said first optical system forms said laser beam into two parallel linear polarized beams which have different intensity distributions from each other, the beam spots of which overlap each other, and which have their polarization planes orthogonal to each other.

60. The fine particle measuring system according to claim 59, wherein a ratio between the values of the detected outputs processed by said measuring means is a ratio between the maximum values of said detected outputs or that between the integrated values thereof.

61. A fine particle measuring system comprising:

at least one laser beam source;

a first optical system for forming the laser beam into a first and a second linear polarized beams, being parallel each other, having respective given intensity distributions, deviating from each other in a direction orthogonal both to a flow direction of a sample fluid and a direction of the laser beam in a range in which the beam spots of said first and second linear polarized beams overlap each other, and having their polarization planes substantially orthogonal to each other, and into a third parallel beam deviating from said first and second linear polarized beams by a given distance in said flow direction;

a flow passage for a sample fluid containing fine particles to flow through, arranged to intersect said first and second linear polarized beams, and said third parallel beam;

a second optical system for forming scattered lights of said first and second linear polarized beams, and said third parallel beam against said fine particles into images on a given image point;

polarizing and dividing means for dividing the scattered lights formed in the images by the second optical system according to the polarization planes;

light detecting means for detecting the scattered lights divided according to the polarization planes and generating detected outputs;

extracting means for extracting a pair of detected outputs of one and the same one of said fine particles, based on a peak of the occurrences of a time interval between two successively detected outputs;

measuring means for selecting an area of a light scattering region to be detected, based on a value of at least two of said extracted pair of detected outputs generated by one and the same one of said fine particles passing said first and second linear polarized beams, and said third parallel beam, measuring particle diameters of said fine particles, based on the selected value of said two outputs, computing a volume of said sample fluid passing said selected area of the light scattering region, based on a time interval between at least one of the detected outputs of said first and second scattered lights, and the detected output of the third scattered light, an computing particle diameter distributions of said fine particles, based on said particle diameters and said volume of said sample fluid.

62. The fine particle measuring system according to claim 61, wherein the time interval between the detected output processed by said measuring means is a time interval between the maximum values of said detected outputs.

63. The fine particle measuring system according to claim 61, wherein said first optical system forms the laser beam into a first and second parallel linear polarized beams which have different intensity distributions from each other, the beam spots of which overlap each other, and have their polarization planes substantially orthogonal to each other, and into a third parallel beam deviating from said first and second linear polarized beams by a given distance in said flow direction in a range in which the beam spots of said first and second linear polarized beams overlap each other.

64. The fine particles measuring system according to claim 63, wherein the time interval between the detected outputs processed by said measuring means is a time interval between the maximum values of said detected outputs.

65. A fine particle measuring method in which laser beam having an intensity gradually increasing over at least the peripheral portion thereof and a portion inner of and near to the peripheral portion from the peripheral portion is radiated to fine particles contained in a sample fluid flowing in a given direction and at a given flow speed, and scattered lights against said fine particles in a light scattering region are detected comprising:

a first step causing said laser beam to scan at a given speed and in a given direction so that said laser beam intersect said flow direction of said sample fluid orthogonally to a direction of said laser beam;

a second step of restricting a radiation area of said laser beam to fine particles in said sample fluid by scanning direction of said laser beam;

a third step of detecting scattered lights formed by said fine particles passing said laser beam;

a fourth step of measuring particle diameters of said fine particles, based on the detected outputs given by the third step and a fifth step of measuring particle diameter distributions of said fine particles, based on a relative flow velocity of said sample fluid given as a vector sum of a scanning velocity of said laser beam and a flow velocity of said sample fluid.

66. A fine particle measuring method in which a laser beam having an intensity gradually increasing over at least the peripheral portion thereof and a portion inner of and near to the peripheral portion inward from the peripheral portion is radiated to fine particles in a sample medium, and scattered lights against said fine particles in a light scattering region are detected comprising:

a first step of forming the laser beam into at least two parallel beams having respective intensity distributions;

a second step of causing said at least two parallel beams to scan at a given speed and in a given direction so that said at least two parallel beams may pass said fine particles;

a third step of detecting at least two scattered lights formed by one and the same one of said fine particles passing said at least two parallel beams among scattered lights formed by said fine particles passing said at least two parallel beams;

a fourth step selecting an area of said light scattering region to be detected, based on a ratio between the values of at least two detected outputs generated by the third step; and a fifth step of measuring particle diameters of said fine particles, based on the value of said at least two detected outputs in said area selected by the fourth step.

67. The fine particle measuring method according to claim 66, wherein when said sample medium is a sample fluid flowing in a given direction and at a given flow speed, said at least two parallel beams used in the first step have their beam spots at least partially overlapping each other in a relative flow direction given by a vector sum of a flow direction of said sample fluid and a scanning direction of said laser beam and deviate from each other by a given distance in said relative flow direction, and when said sample medium does not flow, said at least two parallel beams have at least partially overlap each other in a relative flow direction given by a scanning direction of said laser beam and deviate from each other by a given distance in said relative flow direction, the third step detects at least two scattered lights at a time interval in which a given time passes from the detection of a preceding scattered light, or at a time interval after a preset time has passed from the detection of a preceding scattered light.

68. The fine particle measuring method according to claim 66, wherein the fifth step measures particle diameters of said fine particles, based on the values of said at least two detected outputs in the area selected by the fourth step, and a time width of one of said at least two detected outputs.

69. The fine particle measuring method according to claim 66, wherein the first step forms the laser beam into a first and a second parallel beams which have respective given intensity distributions, the beam spots of which at least partially overlap each other in said relative flow direction, and a third parallel beam deviating from said first and second parallel beams by a given distance in said relative flow direction in a range in which the beam spots of said first and second parallel beams overlap each other, the third step detects three scattered lights successively formed by one and the same one of said fine particles passing said first to third beam among scattered lights formed by said fine particles passing said first to said third beams; and the fifth step measures particle diameters of said fine particles, based on a value of said three detected outputs in the area selected by the fourth step.

70. A fine particle measuring method in which a laser beam having an intensity gradually increasing over at least the peripheral portion and a portion inner of and near to the peripheral portion inward from the peripheral portion is radiated to fine particles contained in a sample medium, and scattered lights against said fine particles in a light scattering region are detected comprising:

a first step of forming the laser beam into at least two parallel beams having respective intensity distributions and deviating from each other by a given distance in a direction orthogonal to a direction of said laser beam;

a second step of causing said at least two parallel beams to that when said sample medium is a sample fluid flowing in a given direction, the beam spots of said at least two parallel beams at least partially overlap each other in a relative flow direction given by a vector sum of a flow direction of said sample fluid and a scanning direction of said laser beam, and when said sample medium does not flow, the beam spots of said at least two parallel beams at least partially overlay each other in a relative flow direction given by a scanning direction of said laser beam;

a third step of detecting scattered lights formed by said fine particles passing said at least two parallel beams;

a fourth step of measuring a time interval between at least two successively generated detected outputs of the scattered lights detected by the third step;

a fifth step of extracting a pair of detected outputs of one and the same of said fine particles, based on a time interval measured by the fourth step;

a six step of selecting an area of said light scattering region to be detected, based on a ratio between the values of at least two detected outputs of said pair extracted by the fifth step; and a seventh step of measuring particle diameters of said fine particles, based on the value of said at least two detected outputs of said light scattering region in an area selected by the sixth step.

71. The fine particle measuring method according to claim 70, wherein the fifth step extracts said pair of detected outputs, based on a peak of the occurrences of the time interval measured by the fourth step.

72. The fine particle measuring method according to claim 70 further comprising, in addition to said first to the seventh steps:

an eighth step of computing a volume of said sample fluid passing the area of said light scattering region selected by the sixth step, based on the time interval measured by the fourth step; and a ninth step of computing particle diameter distributions, based on the particle diameters measured by the seventh step, and the volume of said sample fluid computed by the eighth step.

73. A fine particle measuring system comprising:

a laser beam source;

a first optical system for forming the laser beam from said laser beam source into a laser beam having an intensity gradually increasing over the peripheral portion thereof and a portion inner of and near to the peripheral portion inward from the peripheral portion;

a flow passage for a sample fluid containing fine particles to be measured to flow in a given direction and at a given flow velocity, arranged to intersect said laser beam;

scanning means for causing said laser beam to scan at a given speed and in a given direction so that said laser beam intersects a flow direction of said sample fluid orthogonally to a direction of said laser beam;

radiating area restricting means for restricting the radiating area of said laser beam to fine particles in said sample fluid by a scanning direction of said laser beam;

light detecting means for detecting scattered lights formed by said fine particles passing said laser beam; and fine particle measuring means for measuring particle diameters of said fine particles, based on a value of the detected outputs given by said light detecting means, and computing particle diameter distributions of said fine particles, based on a relative flow velocity of said sample fluid given as a vector sum of a scanning velocity of said laser beam and a flow velocity of said sample fluid, and a measuring result of particle diameters of said fine particles.

74. A fine particle measuring system comprising:

at least one laser beam source;

a first optical system for forming the laser beam from said laser beam source into at least two parallel beams having respective given intensity distributions, and deviating from each other by a given distance in a direction orthogonal to a direction of said laser beam;

a sample reserving member for containing a sample medium containing fine particles to be measured in its flowing condition or stationary condition, arranged to intersect said at least two parallel beams;

scanning means for causing said at least two parallel beams to that when said sample medium is a sample fluid flowing in a given direction, the beam spots of said at least parallel beams at least partially overlap each other in a relative flow direction given by a vector sum of a flow direction of said sample fluid and a scanning direction of said laser beam, and when said sample medium does not flow, the beam spots of said at least two parellel beams at least partially overlap each other in a relative flow direction given by a scanning direction of said laser beam;

a second optical system for forming scattered lights of said at least two parallel beams against said fine particles into images at a given image point;

light detecting means for detecting the scattered lights formed in the images by the second step and generating detected outputs; and measuring means for extracting scattered lights against one and the same one of said fine particles, based on a time interval between at least two of said detected outputs successively generated, selecting an area of light scattering region to be detected based on the values of said at least two detected output, and measuring particle diameters of said fine particles, based on the values of said at least two detected outputs thus extracted and selected.

75. The fine particles measuring system according to claim 74, wherein said measuring means extracts scattered lights against one and the same one of said fine particles at a time interval in which a given time passes from the detection of a preceding scattered light, or at a time interval after a preset time has passed from the detection of a preceding scattered light.

76. The fine particle measuring system according to claim 74, wherein said measuring means extracts scattered lights of one and the same one of said fine particles so as to extract a pair of detected outputs, based on a peak of the occurrences of the time interval between said detected outputs.

77. The fine particle measuring system according to claim 74, wherein said measuring means computes a volume of said sample fluid passing the selected area of the light scattering region and computes particle diameter distributions of said fine particles, based on said particle diameters and the volume of said sample fluid.

78. A flow cell for use in a fine particle measuring system in which a measuring laser beam is radiated to a fluid to form scattered lights, and the scattered lights are observed to measure fine particles in said fluid, and which is so arranged that said fluid passing through a flow-passage in the flow cell may pass said measuring beam comprising:
   a tubular member having a flow passage therein for said fluid to pass through and having a flat region over a given area, which is transparent to said measuring beam, provided at least on the outside surface thereof on the side of observation of scattered lights of said measuring beam;
   an incident block secured to said tubular member at a position of incidence of said measuring beam, and having the surface thereof except for a plane of incidence of said measuring beam opposite to said plane of incidence made sufficiently light absorptive; and
   said incident block is secured to said tubular member through a refractive index adjusting liquid.

79. A flow cell for use in a fine particle measuring system in which a measuring laser beam is radiated to a fluid to form scattered lights, and the scattered lights are observed to measure fine particles in said fluid, and which is so arranged that said fluid passing through a flow passage in the flow cell may pass said measuring beam comprising:
   a tubular member having a flow passage therein for said fluid to pass through and having a flat region over a given area, which is transparent to said measuring beam, provided at least on the outside surface thereof on the side of observation of scattered lights of said measuring beam;
   an incident block secured to said tubular member at a position of incidence of said measuring beam, and having the surface thereof except for a plane of incidence of said measuring beam and a transmission area for said measuring beam opposite to said plane of incidence made sufficiently light absorptive; and
   said incident block is elongated in a scanning direction of said measuring beam.

80. A flow cell for use in a fine particle measuring system in which measuring laser beam is radiated to a fluid to obtain scattered lights, and the scattered lights are observed to measure fine particles in said fluid, and which is so arranged that said fluid passing through a flow passage in the flow cell may pass said measuring beam comprising;
   a tubular member having a flow passage therein for said fluid to pass through and having a flat region over a given area, which is transparent to said measuring beam provided at least on the outside surface thereof on the side of observation of scattered lights of said measuring beam;
   an incident block secured to said tubular member at a position of incidence of said measuring beam, and having the surface thereof except for a plane of incidence of said measuring beam and a transmission area for said measuring beam opposite to said plane of incidence made sufficiently light absorptive; and
   a beam trap member secured to said tubular member at a position where said measuring beam passing said tubular member exits the same, and having a light receiving area for receiving the part of said measuring beam passing said tubular member made sufficiently light absorptive.

81. The flow cell for use in a fine particle measuring system according to claim 80, wherein said incident block and said beam trap member are secured to said tubular member through a refractive index adjusting liquid.

82. The flow cell for use in a fine particle measuring system according to claim 80, wherein said plane of incidence of said incident block is flat substantially orthogonal to said measuring beam, and the outside surface of said incident block, except for an incidence area of said plane of incidence and a transmission area for said measuring beam opposite to said plane of incidence, is coated with a light absorptive film.

83. The flow cell for use in a fine particle measuring system according to claim 80, wherein the outside surface of said beam trap except for the adhering surface thereof to said tubular member is coated with a light absorptive film.

84. The flow cell for use in a fine particle measuring system according to claim 83, wherein said adhering surface of said beam trap member, except for a transmission area for said measuring beam, is coated with a light absorptive film.

85. The flow cell for use in fine particle measuring system according to claim 80, wherein said beam trap member is made of black quartz.

86. The flow cell for use in a fine particle measuring system according to claim 80, wherein said incident block and said beam trap member are elongated in a scanning direction of said measuring beam.

87. A flow cell for use in a fine particle measuring system in which a measuring laser beam is radiated to a fluid to form scattered lights, and the scattered lights are observed to measure fine particles in said fluid, and which is so arranged that said fluid passing through a flow passage in the flow cell may pass said measuring beam comprising:

a tubular member having a flow passage therein for said fluid to pass through and having a flat region over a given area, which is transparent to said measuring beam, provided at least on the outside surface thereof on the side of observation of scatter lights of said measuring beam; and an incident block secured on the outside surface of said tubular member at a position of incidence of said measuring beam, and having the surface thereof except for a plane of incidence of said measuring beam and a transmission area for said measuring beam opposite to said plane of incidence made sufficiently light absorptive.

88. A flow cell for use in a fine particle measuring system according to claim 87 wherein said incident block is secured on the outside surface of said tubular member with optical contact therebetween.

89. The flow cell for use in a fine particle measuring system according to claim 88, wherein said incident block is secured to said tubular member through a refractive index adjusting liquid.

90. The flow cell for use in a fine particle measuring system according to claim 88, wherein said incident block is elongated in a scanning direction of said measuring beam.

91. The flow cell for use in a fine particle measuring system according to claim 87, wherein said incident block is secured to said tubular member through a refractive index adjusting liquid.

92. The flow cell for use in a fine particle measuring sysrem according to claim 87, wherein said plane of incidence of said incident block is flat substantially orthogonal to said measuring beam, and the outside surface of said incident block, except for an incidence area of said plane of incidence and a transmission area for said measuring beam opposite to said plane of incidence, is coated with a light absorptive film.

93. The flow cell for use in fine particle measuring system according to claim 92, wherein said incident block is secured to said tubular member through a refractive index adjusting liquid.

94. The flow cell for use in fine particle measuring system according to claim 87, wherein said incident block is elongated in a scanning direction of said measuring beam.

* * * * *